United States Patent
Bury et al.

(10) Patent No.: US 9,604,963 B2
(45) Date of Patent: Mar. 28, 2017

(54) AMINO-QUINOLINES AS KINASE INHIBITORS

(75) Inventors: Michael Jonathan Bury, Collegeville, PA (US); Linda N. Casillas, Collegeville, PA (US); Adam Kenneth Charnley, Collegeville, PA (US); Pamela A. Haile, Collegeville, PA (US); Robert W. Marquis, Jr., Collegeville, PA (US); John F. Mehlmann, Collegeville, PA (US); Joseph J. Romano, Collegeville, PA (US); Robert R. Singhaus, Jr., Collegeville, PA (US); Gren Z. Wang, Collegeville, PA (US)

(73) Assignee: GlaxoSmithKline Intellectual Property Development Limited, Brentford, Middlesex (GB)

( * ) Notice: Subject to any disclaimer, the term of this patent is extended or adjusted under 35 U.S.C. 154(b) by 0 days.

(21) Appl. No.: 14/002,147

(22) PCT Filed: Mar. 2, 2012

(86) PCT No.: PCT/US2012/027439
§ 371 (c)(1),
(2), (4) Date: Aug. 29, 2013

(87) PCT Pub. No.: WO2012/122011
PCT Pub. Date: Sep. 13, 2012

(65) Prior Publication Data
US 2013/0345258 A1 Dec. 26, 2013

Related U.S. Application Data

(60) Provisional application No. 61/449,843, filed on Mar. 7, 2011, provisional application No. 61/449,574, filed on Mar. 4, 2011.

(51) Int. Cl.
| | |
|---|---|
| *C07D 405/12* | (2006.01) |
| *C07D 401/12* | (2006.01) |
| *A61K 31/4709* | (2006.01) |
| *C07D 405/14* | (2006.01) |
| *C07D 417/12* | (2006.01) |
| *C07D 215/44* | (2006.01) |
| *C07D 417/14* | (2006.01) |
| *C07D 471/04* | (2006.01) |

(52) U.S. Cl.
CPC ........ *C07D 401/12* (2013.01); *A61K 31/4709* (2013.01); *C07D 215/44* (2013.01); *C07D 405/12* (2013.01); *C07D 405/14* (2013.01); *C07D 417/12* (2013.01); *C07D 417/14* (2013.01); *C07D 471/04* (2013.01)

(58) Field of Classification Search
CPC .. C07D 401/12; C07D 405/12; C07D 405/14; C07D 215/44; C07D 417/12; C07D 417/14; C07D 471/04; A61K 31/4709

USPC ........................................... 546/160; 514/312
See application file for complete search history.

(56) References Cited

U.S. PATENT DOCUMENTS

| | | | |
|---|---|---|---|
| 4,916,135 A | 4/1990 | Effland et al. | 514/254 |
| 5,457,105 A | 10/1995 | Barker | 514/234.5 |
| 5,576,322 A | 11/1996 | Takase et al. | |
| 5,710,158 A | 1/1998 | Myers et al. | |
| 5,747,498 A | 5/1998 | Schnur et al. | |
| 5,801,180 A | 9/1998 | Takase et al. | |
| 6,046,206 A | 4/2000 | Pamukcu et al. | 514/259 |
| 6,548,508 B2 | 4/2003 | Westbrook et al. | |
| 6,589,758 B1 | 7/2003 | Zhu | |
| 6,743,799 B2 | 6/2004 | Westbrook et al. | |
| 6,809,097 B1 * | 10/2004 | Thomas et al. | 514/235.2 |
| 7,282,504 B2 | 10/2007 | Armistead et al. | |
| 7,452,887 B2 | 11/2008 | Dickson, Jr. et al. | 514/253.06 |
| 7,566,786 B2 * | 7/2009 | Baldwin et al. | 546/159 |
| 7,569,577 B2 | 8/2009 | Hennequin et al. | 514/266.22 |
| 7,572,915 B2 * | 8/2009 | Barker et al. | 546/159 |
| 7,618,975 B2 | 11/2009 | Cai et al. | |
| 7,709,479 B1 | 5/2010 | Mortlock et al. | |
| 7,939,546 B2 | 5/2011 | Phiasivongsa et al. | 514/313 |
| 8,258,145 B2 | 9/2012 | Cai et al. | 514/266.21 |

(Continued)

FOREIGN PATENT DOCUMENTS

| | | |
|---|---|---|
| CN | 101362719 A | 2/2009 |
| EP | 0 973 746 B1 | 9/2003 |

(Continued)

OTHER PUBLICATIONS

Robinett, Bioorg & Med Chem Lett, vol. 17, 5886-5896, 2007.*
Tigno-Aranjuez, Genes & Development, vol. 24, 2666-2677, 2010.*
Argast, et al. Molec. & Cell. Biochem., (Kluwer Academic Pubs) 268(1-2): 129-140 (2005).
PCT International Preliminary Report on Patentability & PCT Written Opinion of the International Searching Authority, PCT/US13/59600, Jan. 29, 2014.
PCT International Preliminary Report on Patentability & PCT Written Opinion of the International Searching Authority, PCT/US13/59619, Jan. 29, 2014.

(Continued)

*Primary Examiner* — D M Seaman
(74) *Attorney, Agent, or Firm* — Kathryn A. Lutomski; Edward R. Gimmi; William R. Majarian

(57) ABSTRACT

Disclosed are compounds having the formula:

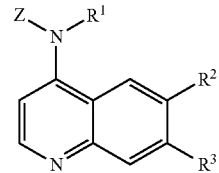

wherein $R^1$, $R^2$, $R^3$ and Z are as defined herein, and methods of making and using the same.

7 Claims, 4 Drawing Sheets

(56) References Cited

U.S. PATENT DOCUMENTS

| | | |
|---|---|---|
| 9,216,965 B2 | 12/2015 | Casillas et al. |
| 2002/0026052 A1 | 2/2002 | Boschelli et al. ............ 546/122 |
| 2002/0147214 A1 | 10/2002 | Cockerill et al. ............ 514/311 |
| 2003/0087919 A1 | 5/2003 | Nagarathnam et al. |
| 2003/0105129 A1 | 6/2003 | Mortlock et al. ............ 514/313 |
| 2003/0125344 A1 | 7/2003 | Nagarathnam et al. |
| 2003/0212276 A1 | 11/2003 | Boschelli et al. ............ 546/153 |
| 2003/0216417 A1 | 11/2003 | Cumming ................. 514/266.4 |
| 2003/0220357 A1 | 11/2003 | Bankston et al. |
| 2004/0242604 A1 | 12/2004 | Bhattacharya et al. ... 514/266.4 |
| 2005/0070561 A1 | 3/2005 | Jung et al. |
| 2005/0137395 A1 | 6/2005 | Hong et al. .................. 540/575 |
| 2005/0267101 A1 | 12/2005 | Randle ......................... 514/221 |
| 2006/0025327 A1 | 2/2006 | Sanchez et al. ................. 514/2 |
| 2006/0116357 A1 | 6/2006 | Heron et al. |
| 2006/0167035 A1 | 7/2006 | Schwede et al. ............ 514/291 |
| 2007/0021446 A1 | 1/2007 | Ehlert et al. ............... 514/266.2 |
| 2007/0299092 A1 | 12/2007 | Floyd Jr et al. ........... 514/266.1 |
| 2008/0032996 A1 | 2/2008 | Mitsuya et al. |
| 2008/0045568 A1 | 2/2008 | Deng et al. .................. 514/312 |
| 2008/0064878 A1 | 3/2008 | Aoki et al. ................. 546/277.4 |
| 2008/0161305 A1 | 7/2008 | Forsyth et al. ............ 514/235.2 |
| 2008/0221132 A1 | 9/2008 | Cai et al. |
| 2008/0227811 A1 | 9/2008 | Chen ............................ 514/312 |
| 2008/0227812 A1 | 9/2008 | Chen ............................ 514/313 |
| 2008/0234267 A1 | 9/2008 | Lackey ...................... 514/235.2 |
| 2008/0269404 A1 | 10/2008 | Paul et al. .................... 524/558 |
| 2008/0312273 A1 | 12/2008 | Hennequin .................. 514/311 |
| 2008/0318971 A1 | 12/2008 | Hewes ..................... 514/252.18 |
| 2009/0099106 A1 | 4/2009 | Phiasivongsa et al. ........ 514/43 |
| 2009/0215770 A1 | 8/2009 | Jung et al. |
| 2009/0226443 A1 | 9/2009 | Filvaroff et al. |
| 2009/0270450 A1 | 10/2009 | Dakin et al. .................. 514/313 |
| 2010/0069412 A1 | 3/2010 | Heron et al. |
| 2010/0135999 A1 | 6/2010 | Nazare et al. ............. 424/133.1 |
| 2011/0053935 A1 | 3/2011 | Folkes et al. |
| 2011/0237629 A1 | 9/2011 | Meibom et al. ............. 514/340 |
| 2011/0256092 A1 | 10/2011 | Phiasivongsa et al. ..... 424/85.2 |
| 2011/0262436 A1 | 10/2011 | Bender et al. |
| 2012/0041024 A1 | 2/2012 | Charnley et al. ............ 514/313 |
| 2012/0053183 A1 | 3/2012 | Russu et al. |
| 2012/0070413 A1 | 3/2012 | Kim et al. ................... 424/85.4 |
| 2012/0122923 A1 | 5/2012 | Cosledan et al. ............ 514/313 |
| 2012/0165321 A1 | 6/2012 | Adams et al. ............. 514/223.2 |
| 2012/0219522 A1 | 8/2012 | Xi ................................ 424/85.4 |
| 2013/0018039 A1 | 1/2013 | Bodmer et al. .......... 514/210.21 |
| 2013/0023532 A1 | 1/2013 | Casillas et al. ............ 514/234.2 |
| 2013/0023534 A1 | 1/2013 | Casillas et al. ............ 514/236.5 |
| 2013/0053375 A1 | 2/2013 | Bury et al. ................. 514/228.2 |
| 2013/0345258 A1 | 12/2013 | Bury et al. ................. 514/228.2 |
| 2014/0100234 A1 | 4/2014 | Knight et al. ........... 514/252.04 |
| 2014/0155396 A1 | 6/2014 | Bannen et al. ............. 514/234.5 |
| 2014/0256949 A1 | 9/2014 | Casillas et al. |

FOREIGN PATENT DOCUMENTS

| | | |
|---|---|---|
| EP | 2 072 502 A1 | 6/2009 |
| GB | 2 345 486 A | 7/2000 |
| WO | WO 96/09294 A1 | 3/1996 |
| WO | WO 98/05647 A1 | 2/1998 |
| WO | WO 99/35146 A1 | 7/1999 |
| WO | WO 02/068394 A1 | 9/2002 |
| WO | WO 02/092571 A1 | 11/2002 |
| WO | WO 03/018022 A1 | 3/2003 |
| WO | WO 03/026666 A1 | 4/2003 |
| WO | WO 2004/037814 A1 | 5/2004 |
| WO | WO 2007/045987 A1 | 4/2007 |
| WO | WO 2008/033748 A2 | 3/2008 |
| WO | WO 2008/033749 A2 | 3/2008 |
| WO | WO 2008/119771 A2 | 10/2008 |
| WO | WO 2009/080200 A1 | 7/2009 |
| WO | WO 2011/011522 A2 | 1/2011 |
| WO | WO 2011/112588 A2 | 9/2011 |
| WO | WO 2011/120025 A1 | 9/2011 |
| WO | WO 2011/120026 A1 | 9/2011 |
| WO | WO 2011/123609 A1 | 10/2011 |
| WO | WO 2011/140442 A1 | 11/2011 |
| WO | WO 2012/021580 A1 | 2/2012 |
| WO | WO 2012/122011 A2 | 9/2012 |
| WO | WO 2013/025958 A1 | 2/2013 |
| WO | WO 2014/043437 A1 | 3/2014 |
| WO | WO 2014/043446 A1 | 3/2014 |
| WO | WO 2014/128622 A1 | 8/2014 |

OTHER PUBLICATIONS

EP Supplementary Search Report for PCT/US11/030103, dated Sep. 23, 2013.
EP Supplementary Search Report for PCT/US11/030104, dated Sep. 17, 2013.
EP Supplementary Search Report for PCT/US11/35521, dated Oct. 23, 2013.
EP Supplementary Search Report for PCT/US11/47183, dated Dec. 17, 2013.
Robinett, et al. Bioorg. Med. Chem. Lett., 17: 5886-5893 (2007). doi: 10.1016/j.bmcl.2007.07.104.
Cavasotto, et al. Bioorg. & Med. Chem. Lett., 16: 1969-1974 (2006).
Kumar, et al. J. Clin. Oncol., 26: 1742-1751 (2008).
Manon, et al. J. Molec. Biol., 365: 160-174 (2007).
PCT International Preliminary Report on Patentability & PCT Written Opinion of the International Searching Authority, PCT/US11/35521 (Aug. 9, 2011).
PCT International Preliminary Report on Patentability & PCT Written Opinion of the International Searching Authority, PCT/US11/47183 (Dec. 30, 2011).
PCT International Preliminary Report on Patentability & PCT Written Opinion of the International Searching Authority, PCT/US12/51247 (Oct. 23, 2012).
PCT International Preliminary Report on Patentability & PCT Written Opinion of the International Searching Authority, PCT/US12/27439, Jun. 7, 2012.
Poster: B. J. Votta, et al., Keystone Symposia on Innate Immunity, Keystone, CO (Mar. 7, 2012).
Poster: C.R. Hanning, AAI Annual Meeting, Pittsburgh PA (May 4, 2014).
Pending Claims of U.S. Appl. No. 13/696,603 (Jan. 22, 2015).
Pending Claims of U.S. Appl. No. 14/283,352 (Jan. 22, 2015).
Pending Claims of U.S. Appl. No. 14/239,193 (Jan. 22, 2015).
Pending Claims of U.S. Appl. No. 14/396,559 (Jan. 22, 2015).
Pending Claims of U.S. Appl. No. 14/397,218 (Jan. 22, 2015).
Sheth, et al. Archives of Biochem. & Biophysics, 503:191-201 (2010).
Poster (WORD): B. J. Votta, et al., Keystone Symposia on Innate Immunity, Keystone, CO (Mar. 7, 2012).
Poster (WORD): C.R. Hanning, AAI Annual Meeting, Pittsburgh PA (May 4, 2014).
Amendment, U.S. Appl. No. 14/762,905, filed on Jul. 23, 2015.
Arostegui, et al., *Arthritis & Rheumatism*, 56(11):3805-3813 (2007).
Biancheri, et al., *Digestive and Liver Disease, Abstract*, 45S:S71 (2013).
Body-Malapel, et al., *Laboratory Investigation*, 88:318-327 (2008).
Carreno, et al., *Acta Ophthalmologica, Abstract*, 2014.
Corridoni, et al., *PNAS*, 110(42):16999-17004 (2013).
Denou, et al., *EMBO Molecular Medicine*, 7(3):259-274 (2015).
Dharancy, et al., *Gastroenterology*, 138:1546-1556 (2010).
Du, et al., *Kidney International*, 84:265-276 (2013).
Ermann, et al., *PNAS*, E2559-E2566 (2014).
Ferrero-Miliani, et al., *Clinical and Experimental Immunology*, 147:227-235 (2006).
Foley, et al., *Pediatric Rheumatology*, 11 (Suppl. 1):A3 (2013).
Geddes, et al., *Infection and Immunity*, 78(12):5107-5115 (2010).
Goh, et al., *The Journal of Immunology*, 191:2691-2699 (2013).
Goncalves, et al., *The Scandanavian Journal of Immunology*, 73:428-435 (2011).
Hedegaard, et al., *Plos One*, 6(5):e20253 (2011).
Heinhuis, et al., *Ann Rheum Dis*, 69:1866-1872 (2009).

(56) References Cited

OTHER PUBLICATIONS

Hysi, et al., *Human Molecular Genetics*, 14(7):935-941 (2005).
Ikeda, et al., *Arthritis Research & Therapy*, 16:R89 (2014).
Jamontt, et al., *Journal of Immunology*, 190:2948-2958 (2013).
Jun, et al., *Journal of Leukocyte Biology*, 94:927-932 (2013).
Kruger, et al., *European Society for Organ Transplantation*, 20:600-607 (2007).
Kvarnhammar, et al., *Plos One*, 8(7):e68701 (2013).
Liu, et al., *Journal of Biological Sciences*, 11(5):525-535 (2015).
McGovern, et al., *Human Molecular Genetics*, 14(10):1245-1250 (2005).
Murias, et al., *Pediatric Rheumatology*, 12(Suppl. 1):P293 (2014).
Nachbur, et al., *Nature Communications*, 6:6442 (2015).
Natarajan, et al., *Journal of Neuroimmunology*, 265:51-60 (2013).
Oh, et al., *Plos Pathogens*, 9(5):e1003351 (2013).
Ospelt, et al., *Arthritis & Rheumatism*, 60(2):355-363 (2009).
Paim-Marque, et al., *Pediatric Rheumatology*, 12(Suppl. 1):P272 (2014).
Penack, et al., *The Journal of Experimental Medicine*, 206(10):2101-2110 (2009).
Peng, et al., *International Immunopharmacology*, 13:440-445 (2012).
Pillai, et al., *Seminars in Ophthalmology*, 28(5-6):327-332 (2013).
Plantinga, et al., *Rheumatology*, 52:806-814 (2013).
Rebane, et al., *The Journal of Allergy & Clinical Immunology*, 129:1297-1306 (2012).
Rosenzweig, et al., *Arthritis & Rheumatism*, 62(4):1051-1059 (2010).
Rosenzweig, et al., *Inflammation Research*, 60:705-714 2011).
Rosenzweig, et al., *Investigative Ophthalmology & Visual Science*, 50(4):1746-1753 (2009).
Rosenzweig, et al., *Investigative Ophthalmology & Visual Science*, 50(4):1739-1745 (2009).
Saha, et al., *Cell Host & Microbe*, 5:137-150 (2009).
Sfriso, et al., *Autoimmunity Reviews*, 12:44-51 (2012).
Shaw, et al., *Immunity*, 34:75-84 (2011).
Shigeoka, et al., *The Journal of Immunology*, 184:2297-2304 (2010).
Uehara, et al., *Diagnostic Pathology*, 4(23):1746 (2009).
Vieira, et al., *The Journal of Immunology*,188:5116-5122 (2012).
Walsh, et al., *Cytokine & Growth Factor Reviews*, 24:91-104 (2013).
Wiken, et al., *The Journal of Clinical Immunology*, 29:78-89 (2009).
Yu, et al., *Plos One*, 6(8):e23855 (2011).
Zhou, et al., *Diabetes & Metabolism*, 38:538-543 (2012).
Amendment, U.S. Appl. No. 14/762,905, filed Jul. 23, 2015.
Amendment, U.S. Appl. No. 14/397,218, filed Nov. 17, 2015.
Amendment, U.S. Appl. No. 14/239,193, filed Nov. 30, 2015.
Amendment, U.S. Appl. No. 14/933,201, filed Nov. 19, 2015.
Amendment, U.S. Appl. No. 14/934,395, filed Nov. 19, 2015.
Cai, et al. Journal of Medicinal Chemistry, 53(5): 2000-2009 (2010).
Foley, et al. Pediatric Rheumatology, 2013, 11(Suppl.): A3 (published Nov. 8, 2013; presented 7th Congress of ISSAID, Lusanne, Switzerland May 22-26, 2013).

* cited by examiner

AMINO-QUINOLINES AS KINASE INHIBITORS

This application is a 371 of International Application No. PCT/US2012/027439, filed 2 Mar. 2012, which claims the benefit of U.S. Provisional Application Nos. 61/449,843, filed 7 Mar. 2011 and 61/449,574, filed 4 Mar. 2011, which are incorporated herein in their entireties.

BACKGROUND OF THE INVENTION

Field of the Invention

The present invention relates to 4-amino-quinolines that inhibit RIP2 kinase and methods of making and using the same. Specifically, the present invention relates to substituted 4-amino-quinolines as RIP2 kinase inhibitors.

Background of the Invention

Receptor interacting protein-2 (RIP2) kinase, which is also referred to as CARD3, RICK, CARDIAK, or RIPK2, is a TKL family serine/threonine protein kinase involved in innate immune signaling. RIP2 kinase is composed of an N-terminal kinase domain and a C-terminal caspase-recruitment domain (CARD) linked via an intermediate (IM) region ((1998) *J. Biol. Chem.* 273, 12296-12300; (1998) *Current Biology* 8, 885-889; and (1998) *J. Biol. Chem.* 273, 16968-16975). The CARD domain of RIP2 kinase mediates interaction with other CARD-containing proteins, such as NOD1 and NOD2 ((2000) *J. Biol. Chem.* 275, 27823-27831 and (2001) *EMBO reports* 2, 736-742). NOD1 and NOD2 are cytoplasmic receptors which play a key role in innate immune surveillance. They recognize both gram positive and gram negative bacterial pathogens and are activated by specific peptidoglycan motifs, diaminopimelic acid (i.e., DAP) and muramyl dipeptide (MDP), respectively ((2007) *J Immunol* 178, 2380-2386).

Following activation, RIP2 kinase associates with NOD 1 or NOD2 and appears to function principally as a molecular scaffold to bring together other kinases (TAK1, IKKα/β/γ) involved in NF-κB and mitogen-activated protein kinase activation ((2006) *Nature Reviews Immunology* 6, 9-20). RIP2 kinase undergoes a K63-linked polyubiquitination on lysine-209 which facilitates TAK1 recruitment ((2008) *EMBO Journal* 27, 373-383). This post-translational modification is required for signaling as mutation of this residue prevents NOD1/2 mediated NF-kB activation. RIP2 kinase also undergoes autophosphorylation on serine-176, and possibly other residues ((2006) *Cellular Signalling* 18, 2223-2229). Studies using kinase dead mutants (K47A) and non-selective small molecule inhibitors have demonstrated that RIP2 kinase activity is important for regulating the stability of RIP2 kinase expression and signaling ((2007) *Biochem J* 404, 179-190 and (2009) *J. Biol. Chem.* 284, 19183-19188).

Dysregulation of RIP2-dependent signaling has been linked to autoinflammatory diseases. Gain-of-function mutations in the NACHT-domain of NOD2 cause Blau Syndrome, early-onset sarcoidosis, a pediatric granulomateous disease characterized by uveitis, dermatitis, and arthritis ((2001) *Nature Genetics* 29, 19-20; (2005) *Journal of Rheumatology* 32, 373-375; (2005) *Current Rheumatology Reports* 7, 427-433; (2005) *Blood* 105, 1195-1197; (2005) *European Journal of Human Genetics* 13, 742-747; (2006) *American Journal of Ophthalmology* 142, 1089-1092; (2006) *Arthritis & Rheumatism* 54, 3337-3344; (2009) *Arthritis & Rheumatism* 60, 1797-1803; and (2010) *Rheumatology* 49, 194-196). Mutations in the LRR-domain of NOD2 have been strongly linked to susceptibility to Crohn's Disease ((2002) *Am. J. Hum. Genet.* 70, 845-857; (2004) *European Journal of Human Genetics* 12, 206-212; (2008) *Mucosa/Immunology* (2008) 1 (Suppl 1), S5-S9. 1, S5-S9; (2008) *Inflammatory Bowel Diseases* 14, 295-302; (2008) *Experimental Dermatology* 17, 1057-1058; (2008) *British Medical Bulletin* 87, 17-30; (2009) *Inflammatory Bowel Diseases* 15, 1145-1154 and (2009) *Microbes and Infection* 11, 912-918). Mutations in NOD1 have been associated with asthma ((2005) *Hum. Mol. Genet.* 14, 935-941) and early-onset and extra-intestinal inflammatory bowel disease ((2005) *Hum. Mol. Genet.* 14, 1245-1250). Genetic and functional studies have also suggested a role for RIP2-dependent signaling in a variety of other granulomateous disorders, such as sarcoidosis ((2009) *Journal of Clinical Immunology* 29, 78-89 and (2006) *Sarcoidosis Vasculitis and Diffuse Lung Diseases* 23, 23-29) and Wegner's Granulomatosis ((2009) *Diagnostic Pathology* 4, 23).

A potent, selective, small molecule inhibitor of RIP2 kinase activity would block RIP2-dependent pro-inflammatory signaling and thereby provide a therapeutic benefit in autoinflammatory diseases characterized by increased and/or dysregulated RIP2 kinase activity.

SUMMARY OF THE INVENTION

The invention is directed to 6,7-disubstituted-4-amino-quinolines. Specifically, the invention is directed to a compound according to Formula (I):

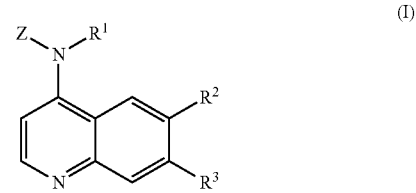

(I)

wherein:

$R^1$ is H, —$SO_2(C_1$-$C_4$alkyl), —$CO(C_1$-$C_4$alkyl), or ($C_1$-$C_4$alkyl);

$R^2$ is —$SOR^a$ or —$SO_2R^a$, wherein $R^a$ is an optionally substituted ($C_1$-$C_6$)alkyl, ($C_3$-$C_7$)cycloalkyl, 4-7 membered heterocycloalkyl, aryl, or heteroaryl group, wherein:

said ($C_1$-$C_6$)alkyl is optionally substituted by one or two groups each independently selected from the group consisting of cyano, hydroxyl, ($C_1$-$C_6$)alkoxy, ($C_1$-$C_6$)alkoxy($C_2$-$C_6$)alkoxy, —$CO_2H$, —$CO_2(C_1$-$C_4$)alkyl, —$SO_2(C_1$-$C_4$ alkyl), —$CONH_2$, —$CONH(C_1$-$C_4$ alkyl), —$NHC(=O)$ ($C_1$-$C_4$ alkyl), —$CON(C_1$-$C_4$ alkyl)($C_1$-$C_4$ alkyl), —$N(C_1$-$C_4$ alkyl)($C(=O)(C_1$-$C_4$ alkyl)), —$SO_2NH_2$, —$SO_2NH(C_1$-$C_4$ alkyl), —$NHSO_2(C_1$-$C_4$ alkyl), —$SO_2N(C_1$-$C_4$ alkyl)($C_1$-$C_4$ alkyl), —$N(C_1$-$C_4$ alkyl)($SO_2(C_1$-$C_4$ alkyl)), amino, ($C_1$-$C_4$ alkyl)amino-, ($C_1$-$C_4$ alkyl)($C_1$-$C_4$ alkyl)amino-, $C_3$-$C_7$cycloalkyl, phenyl, 5-6 membered heteroaryl, 9-10 membered heteroaryl, 4-7 membered heterocycloalkyl and (phenyl)($C_1$-$C_4$ alkyl)amino-, wherein said $C_3$-$C_7$cycloalkyl, phenyl, (phenyl)($C_1$-$C_4$ alkyl)amino-, 5-6 membered heteroaryl, 9-10 membered heteroaryl or 4-7 membered heterocycloalkyl is optionally substituted by 1-3 groups each independently selected from the group consisting of halogen, —$CF_3$, ($C_1$-$C_4$)alkyl, hydroxy($C_1$-$C_4$)alkyl and ($C_1$-$C_4$)alkoxy, said ($C_3$-$C_7$)cycloalkyl or 4-7 membered heterocycloalkyl is optionally substituted by 1-3 groups each independently selected from the group consisting of halogen, —$CF_3$, hydroxyl, amino, (C₁-C₄ alkyl)amino-, (C₁-C₄ alkyl)(C₁-C₄ alkyl)amino-, (C₁-C₄)alkyl, phenyl(C₁-C₄)alkyl-, hydroxy(C₁-C₄)alkyl-, oxo, (C₁-C₄)alkoxy, and (C₁-C₄)alkoxy(C₂-C₄)alkoxy-, and said aryl or heteroaryl is optionally substituted by 1-3 groups each independently selected from the group consisting of halogen, —CF₃, hydroxyl, amino, (C₁-C₄)alkyl, phenyl(C₁-C₄)alkyl-, hydroxy(C₁-C₄)alkyl- and (C₁-C₄)alkoxy, and wherein said heteroaryl is a 5-6 membered heteroaryl or a 9-10 membered heteroaryl, and any of said 4-7 membered heterocycloalkyl contains one heteroatom selected from the group consisting of N, O and S, any of said 5-6 membered heteroaryl contains one heteroatom selected from the group consisting of N, O and S and optionally further containing one or two nitrogen atoms, and any of said 9-10 membered heteroaryl contains one heteroatom selected from the group consisting of N, O and S and optionally further containing 1, 2 or 3 nitrogen atoms;

R³ is halogen, hydroxy, (C₁-C₄)alkyl-, (C₁-C₄)alkoxy-, halo(C₁-C₄)alkyl-, halo(C₁-C₄)alkoxy-, (C₁-C₄)alkoxy(C₁-C₆)alkyl-, halo (C₁-C₄)alkoxy(C₁-C₆)alkyl-, (C₁-C₄)alkoxy(C₂-C₆)alkoxy-, halo(C₁-C₄)alkoxy(C₂-C₆)alkoxy-, hydroxy(C₁-C₄)alkyl-, hydroxy(C₂-C₆)alkoxy-, cyano(C₁-C₄)alkyl-, cyano(C₂-C₆)alkoxy-, or (C₃-C₆)cycloalkoxy-, wherein the halo(C₁-C₄)alkyl-, halo(C₁-C₄)alkoxy-, halo(C₁-C₄)alkoxy(C₁-C₆)alkyl-, or halo(C₁-C₄)alkoxy(C₂-C₆)alkoxy-contains 2 or 3 halo atoms and wherein the (C₃-C₆)cycloalkyl moiety of the (C₃-C₆)cycloalkoxy-group, is optionally substituted by a group selected from the group consisting of cyano, halo, hydroxyl, (C₁-C₆)alkoxy and (C₁-C₄)alkoxy(C₂-C₆)alkoxy;

Z is phenyl or aryl(C₁-C₄)alkyl-, substituted by R⁴, R⁵, R⁶ and R⁷, wherein:

R⁴ is H, halogen, cyano, (C₁-C₄)alkyl, halo(C₁-C₄)alkyl, (C₁-C₄)alkoxy, phenoxy, phenyl(C₁-C₄)alkoxy, hydroxyl, hydroxy(C₁-C₄)alkyl-, or aminocarbonyl, wherein the phenyl moiety of said phenoxy or phenyl(C₁-C₄)alkoxy- is optionally substituted by 1-3 substituents each independently selected from the group consisting of halogen, —CF₃, (C₁-C₄)alkyl and (C₁-C₄)alkoxy; and each of R⁵, R⁶ and R⁷ is independently selected from the group consisting of H, hydroxyl, halogen, —CF₃, hydroxy(C₁-C₄)alkyl, (C₁-C₄)alkyl and (C₁-C₄)alkoxy; or Z is phenyl substituted by R⁸, R⁹ and R¹⁰, wherein:

R⁸ and R⁹ are located on adjacent atoms and taken together with the atoms to which they are attached form a 5-membered heterocyclic group containing 1, 2 or 3 heteroatoms each independently selected from the group consisting of N, O and S, which 5-membered heterocyclic group is substituted by R¹¹;

wherein one of R¹⁰ or R¹¹ is H, halogen, cyano, (C₁-C₄) alkyl, halo(C₁-C₄)alkyl, (C₁-C₄)alkoxy, phenoxy, phenyl(C₁-C₄)alkoxy, hydroxyl, hydroxy(C₁-C₄)alkyl-, or aminocarbonyl, where the phenyl moiety of said phenoxy or phenyl(C₁-C₄)alkoxy is optionally substituted by 1-3 substituents each independently selected from the group consisting of halogen, —CF₃, (C₁-C₄)alkyl and (C₁-C₄)alkoxy; and the other of R¹⁰ or R¹¹ is H, hydroxyl, halogen, halo(C₁-C₄)alkyl, hydroxy(C₁-C₄)alkyl, (C₁-C₄)alkyl or (C₁-C₄)alkoxy; or Z is pyrazolyl, having the formula:

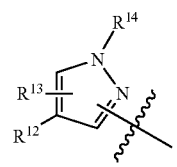

wherein:
R¹² is methyl or trifluoromethyl (—CH₃ or —CF₃);
R¹³ is H, methyl, hydroxymethyl, or trifluoromethyl (—CH₃, —CH₂OH or —CF₃);
R¹⁴ is H or (C₁-C₃)alkyl; or
R¹² and R¹³, taken together with the atoms to which they are attached, form a 6 membered carbocyclic ring or heterocyclic ring substituted by R¹⁵ and R¹⁶, wherein the heterocyclic ring contains 1 nitrogen atom;
wherein R¹⁵ and R¹⁶ are each independently selected from the group consisting of H, halogen, cyano, (C₁-C₄)alkyl, halo(C₁-C₄)alkyl, (C₁-C₄)alkoxy, phenoxy, phenyl(C₁-C₄) alkoxy, hydroxyl, hydroxy(C₁-C₄)alkyl-, and aminocarbonyl, wherein the phenyl moiety of said phenoxy or phenyl (C₁-C₄)alkoxy is optionally substituted by 1-3 substituents each independently selected from the group consisting of halogen, —CF₃, (C₁-C₄)alkyl and (C₁-C₄)alkoxy;

provided that the compound is not N-(4-chloro-2-fluorophenyl)-7-methoxy-6-[(2-methoxyethyl)sulfinyl]-4-quinolinamine or 3-[[7-bromo-6-(methylsulfonyl)-4-quinolinyl]amino]-4-methyl-phenol;

or a salt, particularly a pharmaceutically acceptable salt, thereof.

The compounds according to Formula (I), or salts, particularly pharmaceutically acceptable salts, thereof, are inhibitors of RIP2 kinase.

Accordingly, the present invention is also directed to a method of inhibiting RIP2 kinase which method comprises contacting a cell with a compound according to Formula (I), or a salt, particularly a pharmaceutically acceptable salt, thereof.

The invention is further directed to a method of treating a RIP2 kinase-mediated disease or disorder which comprises administering a therapeutically effective amount of a compound according to Formula (I), or a salt, particularly a pharmaceutically acceptable salt thereof, to a patient (a human or other mammal, particularly, a human) in need thereof. Examples of RIP2 kinase-mediated diseases or disorders include uveitis, Crohn's disease, ulcerative colitis, early-onset and extra-intestinal inflammatory bowel disease and granulomateous disorders, such as sarcoidosis, Blau syndrome, early-onset sarcoidosis and Wegner's Granulomatosis.

The present invention is further directed to a pharmaceutical composition comprising a compound according to Formula (I), or a salt, particularly a pharmaceutically acceptable salt, thereof and a pharmaceutically acceptable excipient. Particularly, this invention is directed to a pharmaceutical composition for the treatment of a RIP2 kinase-mediated disease or disorder, where the composition comprises a compound according to Formula (I), or a salt, particularly a pharmaceutically acceptable salt, thereof and a pharmaceutically acceptable excipient.

DETAILED DESCRIPTION OF THE INVENTION

Figure 1:
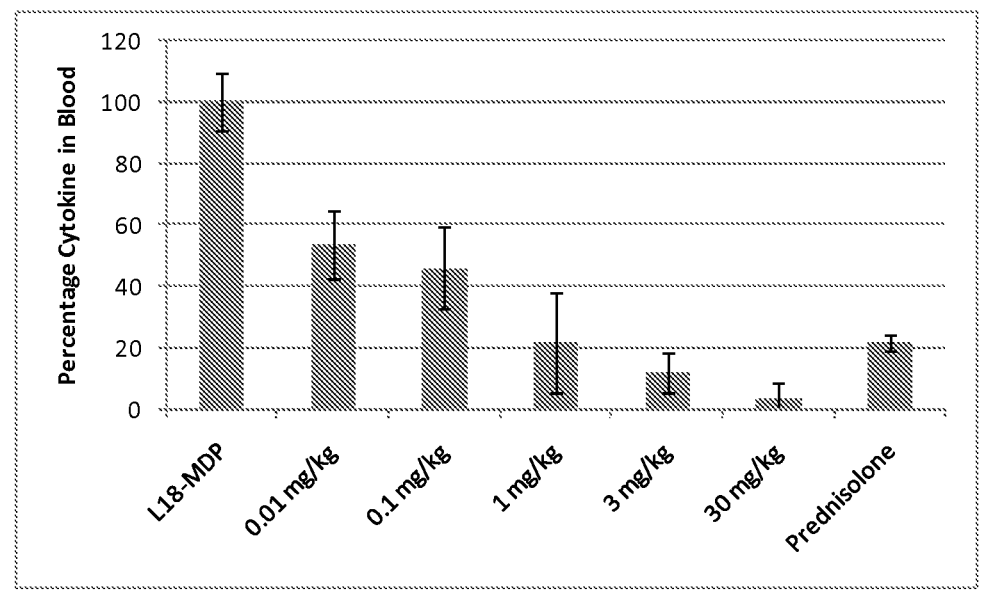
FIG. 1 shows the combined cytokine response in rat whole blood samples obtained after pre-dosing rats with the compound of Example 1, followed by dosing with L18-MDP.

The alternative definitions for the various groups and substituent groups of Formula (I) provided throughout the specification are intended to particularly describe each compound species disclosed herein, individually, as well as groups of one or more compound species. The scope of this invention includes any combination of these group and substituent group definitions. The compounds of the invention are only those which are contemplated to be "chemically stable" as will be appreciated by those skilled in the art.

It will also be appreciated by those skilled in the art that when Z is pyrazolyl, the compounds of this invention may exist as pyrazole isomers represented by Formula (I-A) and Formula (I-B):

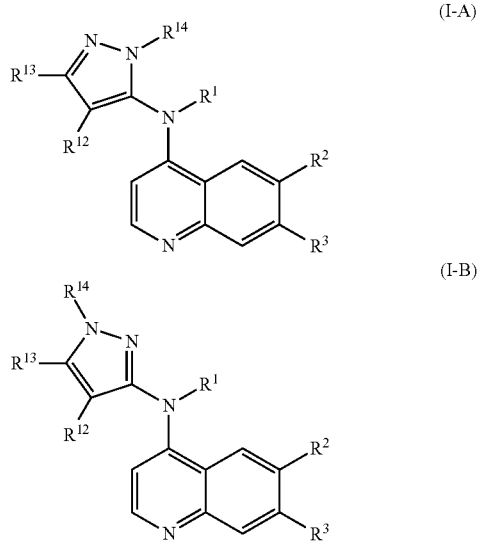

When $R^{14}$ is H, the compounds of this invention may exist as tautomers (I-A) and (I-B) and may be represented as Formula (I-C).

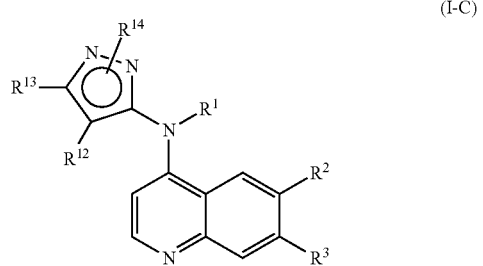

When $R^{14}$ is $(C_1\text{-}C_3)$alkyl, the compounds of this invention, may exist as either one of the regioisomers represented by Formula (I-A) or Formula (I-B), or as a mixture thereof.

In addition, it will be appreciated by those skilled in the art that the compounds of this invention, depending on further substitution, may exist in other tautomeric forms. All tautomeric forms of the compounds described herein are intended to be encompassed within the scope of the present invention. It is to be understood that any reference to a named compound of this invention is intended to encompass all tautomers of the named compound and any mixtures of tautomers of the named compound.

As used herein, the term "alkyl" represents a saturated, straight or branched hydrocarbon moiety. Exemplary alkyls include, but are not limited to methyl (Me), ethyl (Et), n-propyl, isopropyl, n-butyl, s-butyl, isobutyl, t-butyl and pentyl. The term "$C_1\text{-}C_4$ alkyl" refers to an alkyl group or moiety containing from 1 to 4 carbon atoms.

When the term "alkyl" is used in combination with other substituent groups, such as "haloalkyl" or "hydroxyalkyl" or "arylalkyl", the term "alkyl" is intended to encompass a divalent straight or branched-chain hydrocarbon radical. For example, "arylalkyl" is intended to mean the radical-alkylaryl, wherein the alkyl moiety thereof is a divalent straight or branched-chain carbon radical and the aryl moiety thereof is as defined herein, and is represented by the bonding arrangement present in a benzyl group (—$CH_2$-phenyl); "halo($C_1\text{-}C_4$)alkyl" or "($C_1\text{-}C_4$)haloalkyl" is intended to mean a radical having one or more halogen atoms, which may be the same or different, at one or more carbon atoms of an alkyl moiety containing from 1 to 4 carbon atoms, which a is straight or branched-chain carbon radical, and is represented by a trifluoromethyl group (—$CF_3$).

As used herein, the term "cycloalkyl" refers to a non-aromatic, saturated, cyclic hydrocarbon ring. The term "($C_3$-$C_8$)cycloalkyl" refers to a non-aromatic cyclic hydrocarbon ring having from three to eight ring carbon atoms. Exemplary "($C_3$-$C_8$)cycloalkyl" groups useful in the present invention include cyclopropyl, cyclobutyl, cyclopentyl, cyclohexyl, cycloheptyl, and cyclooctyl.

"Alkoxy" refers to a group containing an alkyl radical attached through an oxygen linking atom. The term "($C_1$-$C_4$)alkoxy" refers to a straight- or branched-chain hydrocarbon radical having at least 1 and up to 4 carbon atoms attached through an oxygen linking atom. Exemplary "($C_1$-$C_4$)alkoxy" groups useful in the present invention include, but are not limited to, methoxy, ethoxy, n-propoxy, isopropoxy, n-butoxy, s-butoxy, isobutoxy, and t-butoxy.

"Aryl" represents a group or moiety comprising an aromatic, monovalent monocyclic or bicyclic hydrocarbon radical containing from 6 to 10 carbon ring atoms, which may be fused one or more cycloalkyl rings.

Generally, in the compounds of this invention, aryl is phenyl.

Heterocyclic groups may be heteroaryl or heterocycloalkyl groups.

"Heterocycloalkyl" represents a group or moiety comprising a non-aromatic, monovalent monocyclic or bicyclic radical, which is saturated or partially unsaturated, containing 3 to 10 ring atoms, unless otherwise specified, which includes 1 to 4 heteroatoms selected from nitrogen, oxygen and sulfur. Illustrative examples of heterocycloalkyls include, but are not limited to, azetidinyl, oxetanyl, pyrrolidyl (or pyrrolidinyl), piperidinyl, piperazinyl, morpholinyl, tetrahydro-2H-1,4-thiazinyl, tetrahydrofuryl (or tetrahydrofuranyl), dihydrofuryl, oxazolinyl, thiazolinyl, pyrazolinyl, tetrahydropyranyl, dihydropyranyl, 1,3-dioxolanyl, 1,3-dioxanyl, 1,4-dioxanyl, 1,3-oxathiolanyl, 1,3-oxathianyl, 1,3-dithianyl, azabicylo[3.2.1]octyl, azabicylo[3.3.1]nonyl, azabicylo[4.3.0]nonyl, oxabicylo[2.2.1]heptyl and 1,5,9-triazacyclododecyl.

In some of the compounds of this invention, heterocycloalkyl groups include 4-membered heterocycloalkyl groups containing one heteroatom, such as oxetanyl, thietanyl and azetidinyl.

In other compounds of this invention, heterocycloalkyl groups include 5-membered heterocycloalkyl groups containing one heteroatom selected from nitrogen, oxygen and sulfur and optionally containing one or two an additional nitrogen atoms, or optionally containing one additional oxygen or sulfur atom, such as pyrrolidyl (or pyrrolidinyl), tetrahydrofuryl (or tetrahydrofuranyl), tetrahydrothienyl, dihydrofuryl, oxazolinyl, thiazolinyl, imidazolinyl, pyrazolinyl, 1,3-dioxolanyl, and 1,3-oxathiolan-2-on-yl.

In other compounds of this invention, heterocycloalkyl groups are 6-membered heterocycloalkyl groups containing one heteroatom selected from nitrogen, oxygen and sulfur and optionally containing one or two an additional nitrogen atoms or one additional oxygen or sulfur atom, such as piperidyl (or piperidinyl), piperazinyl, morpholinyl, thiomorpholinyl, 1,1 dioxoido-thiomorpholin-4-yl, tetrahydropyranyl, dihydropyranyl, tetrahydro-2H-1,4-thiazinyl, 1,4-dioxanyl, 1,3-oxathianyl, and 1,3-dithianyl.

"Heteroaryl" represents a group or moiety comprising an aromatic monovalent monocyclic or bicyclic radical, containing 5 to 10 ring atoms, including 1 to 4 heteroatoms selected from nitrogen, oxygen and sulfur. This term also encompasses bicyclic heterocyclic-aryl compounds containing an aryl ring moiety fused to a heterocycloalkyl ring moiety, containing 5 to 10 ring atoms, including 1 to 4 heteroatoms selected from nitrogen, oxygen and sulfur. Illustrative examples of heteroaryls include, but are not limited to, thienyl, pyrrolyl, imidazolyl, pyrazolyl, furyl (or furanyl), isothiazolyl, isoxazolyl, oxazolyl, oxadiazolyl, thiazolyl, pyridyl (or pyridinyl), pyrazinyl, pyrimidinyl, pyridazinyl, triazinyl, tetrazinyl, triazolyl, tetrazolyl, benzo[b]thienyl, isobenzofuryl, 2,3-dihydrobenzofuryl, chromenyl, chromanyl, indolizinyl, isoindolyl, indolyl, indazolyl, purinyl, isoquinolyl, quinolyl, phthalazinyl, naphthridinyl, quinzolinyl, benzothiazolyl, benzimidazolyl, tetrahydroquinolinyl, cinnolinyl, pteridinyl, and isothiazolyl.

In some embodiments, the heteroaryl groups present in the compounds of this invention are 5-membered and/or 6-membered monocyclic heteroaryl groups. Selected 5-membered heteroaryl groups contain one nitrogen, oxygen or sulfur ring heteroatom, and optionally contain 1, 2 or 3 additional nitrogen ring atoms. Selected 6-membered heteroaryl groups contain 1, 2, 3 or 4 nitrogen ring heteroatoms. Selected 5- or 6-membered heteroaryl groups include thienyl, pyrrolyl, imidazolyl, pyrazolyl, furyl (furanyl), isothiazolyl, isoxazolyl, oxazolyl, oxadiazolyl, thiazolyl, triazolyl and tetrazolyl or pyridyl, pyrazinyl, pyrimidinyl, pyridazinyl and triazinyl.

In other embodiments, the heteroaryl groups present in the compounds of this invention are 9-membered or 10-membered monocyclic heteroaryl groups. Selected 9-10 membered heteroaryl groups contain one nitrogen, oxygen or sulfur ring heteroatom, and optionally contain 1, 2, 3 or 4 additional nitrogen ring atoms.

In some of the compounds of this invention, heteroaryl groups include 9-membered heteroaryl groups include benzothienyl, benzofuranyl, indolyl, indolinyl, isoindolyl, isoindolinyl, indazolyl, indolizinyl, isobenzofuryl, 2,3-dihydrobenzofuryl, benzoxazolyl, benzthiazolyl, benzimidazolyl, benzoxadiazolyl, benzthiadiazolyl, benzotriazolyl, 1,3-benzoxathiol-2-on-yl (2-oxo-1,3-benzoxathiolyl), purinyl and imidazopyridinyl.

In some of the compounds of this invention, heteroaryl groups include 10-membered heteroaryl groups include chromenyl, chromanyl, quinolyl, isoquinolyl, phthalazinyl, naphthridinyl, quinazolinyl, quinoxalinyl, 4H-quinolizinyl, tetrahydroquinolinyl, cinnolinyl, and pteridinyl.

It is to be understood that the terms heterocycle, heterocyclic, heteroaryl, heterocycloalkyl, are intended to encompass stable heterocyclic groups where a ring nitrogen heteroatom is optionally oxidized (e.g., heterocyclic groups containing an N-oxide, such as pyridine-N-oxide) or where a ring sulfur heteroatom is optionally oxidized (e.g., heterocyclic groups containing sulfones or sulfoxide moieties, such as tetrahydrothienyl-1-oxide (a tetrahydrothienyl sulfoxide) or tetrahydrothienyl-1,1-dioxide (a tetrahydrothienyl sulfone)).

"Oxo" represents a double-bonded oxygen moiety; for example, if attached directly to a carbon atom forms a carbonyl moiety (C=O). The terms "halogen" and "halo" represent chloro, fluoro, bromo or iodo substituents. "Hydroxy" or "hydroxyl" is intended to mean the radical —OH.

As used herein, the terms "compound(s) of the invention" or "compound(s) of this invention" mean a compound of Formula (I), as defined above, in any form, i.e., any salt or non-salt form (e.g., as a free acid or base form, or as a salt, particularly a pharmaceutically acceptable salt thereof) and any physical form thereof (e.g., including non-solid forms (e.g., liquid or semi-solid forms), and solid forms (e.g., amorphous or crystalline forms, specific polymorphic forms, solvate forms, including hydrate forms (e.g., mono-, di- and hemi-hydrates)), and mixtures of various forms.

As used herein, the term "optionally substituted" means unsubstituted groups or rings (e.g., cycloalkyl, heterocycloalkyl, and heteroaryl rings) and groups or rings substituted with one or more specified substituents.

The invention is further directed to a compound according to Formula (I), wherein:

W is H, —SO$_2$(C$_1$-C$_4$alkyl), —CO(C$_1$-C$_4$alkyl), or (C$_1$-C$_4$alkyl);

R$^2$ is —SOR$^a$ or —SO$_2$R$^a$, wherein R$^a$ is an optionally substituted (C$_1$-C$_6$)alkyl, (C$_3$-C$_7$)cycloalkyl, 4-7 membered heterocycloalkyl, aryl, or heteroaryl, wherein:

said (C$_1$-C$_6$)alkyl is optionally substituted by one or two groups each independently selected from the group consisting of cyano, hydroxyl, (C$_1$-C$_6$)alkoxy, (C$_1$-C$_6$)alkoxy(C$_2$-C$_6$)alkoxy, —CO$_2$H, —CO$_2$(C$_1$-C$_4$)alkyl, —SO$_2$(C$_1$-C$_4$ alkyl), —CONH$_2$, —CONH(C$_1$-C$_4$ alkyl), —CON(C$_1$-C$_4$ alkyl)(C$_1$-C$_4$ alkyl), —SO$_2$NH$_2$, —SO$_2$NH(C$_1$-C$_4$ alkyl), —SO$_2$N(C$_1$-C$_4$ alkyl)(C$_1$-C$_4$ alkyl), amino, (C$_1$-C$_4$ alkyl)amino-, (C$_1$-C$_4$ alkyl)(C$_1$-C$_4$ alkyl)amino-, C$_3$-C$_7$cycloalkyl, phenyl, 5-6 membered heteroaryl, 9-10 membered heteroaryl, 4-7 membered heterocycloalkyl and (phenyl)(C$_1$-C$_4$ alkyl)amino-, wherein said C$_3$-C$_7$cycloalkyl, phenyl, (phenyl)(C$_1$-C$_4$ alkyl)amino-, 5-6 membered heteroaryl, 9-10 membered heteroaryl or 4-7 membered heterocycloalkyl is optionally substituted by 1-3 groups each independently selected from the group consisting of halogen, —CF$_3$, (C$_1$-C$_4$)alkyl, hydroxy(C$_1$-C$_4$)alkyl and (C$_1$-C$_4$)alkoxy, said (C$_3$-C$_7$)cycloalkyl or 4-7 membered heterocycloalkyl is optionally substituted by 1-3 groups each independently selected from the group consisting of halogen, —CF$_3$, hydroxyl, amino, (C$_1$-C$_4$)alkyl, phenyl(C$_1$-C$_4$)alkyl-, hydroxy(C$_1$-C$_4$)alkyl-, oxo and (C$_1$-C$_4$)alkoxy, and said aryl or heteroaryl is optionally substituted by 1-3 groups each independently selected from the group consisting of halogen, —CF$_3$, hydroxyl, amino, (C$_1$-C$_4$)alkyl, phenyl(C$_1$-C$_4$)alkyl-, hydroxy(C$_1$-C$_4$)alkyl- and (C$_1$-C$_4$)alkoxy, and wherein said heteroaryl is a 5-6 membered heteroaryl or a 9-10 membered heteroaryl, and any of said 4-7 membered heterocycloalkyl contains one heteroatom selected from the group consisting of N, O and S, any of said 5-6 membered heteroaryl contains one heteroatom selected from the group consisting of N, O and S and optionally further containing one or two nitrogen atoms, and any of said 9-10 membered heteroaryl contains one heteroatom selected from the group consisting of N, O and S and optionally further containing 1, 2 or 3 nitrogen atoms;

R$^3$ is halogen, hydroxy, (C$_1$-C$_4$)alkyl-, (C$_1$-C$_4$)alkoxy-, halo(C$_1$-C$_4$)alkyl-, halo(C$_1$-C$_4$)alkoxy-, (C$_1$-C$_4$)alkoxy(C$_1$-C$_6$)alkyl-, halo (C$_1$-C$_4$)alkoxy(C$_1$-C$_6$)alkyl-, (C$_1$-C$_4$)alkoxy(C$_2$-C$_6$)alkoxy-, halo(C$_1$-C$_4$)alkoxy(C$_2$-C$_6$)alkoxy-, hydroxy(C$_1$-C$_4$)alkyl-, hydroxy(C$_2$-C$_6$)alkoxy-, cyano(C$_1$-C$_4$)alkyl-, cyano(C$_2$-C$_6$)alkoxy-, or (C$_3$-C$_6$)cycloalkoxy-, wherein the halo(C$_1$-C$_4$)alkyl-, halo(C$_1$-C$_4$)alkoxy-, halo (C$_1$-C$_4$)alkoxy(C$_1$-C$_6$)alkyl-, or halo(C$_1$-C$_4$)alkoxy(C$_2$-C$_6$) alkoxy- contains 2 or 3 halo atoms and wherein the (C$_3$-C$_6$) cycloalkyl moiety of the (C$_3$-C$_6$)cycloalkoxy- group, is optionally substituted by a group selected from the group consisting of cyano, halo, hydroxyl, (C$_1$-C$_6$)alkoxy and (C$_1$-C$_4$)alkoxy(C$_2$-C$_6$)alkoxy;

Z is phenyl or aryl(C$_1$-C$_4$)alkyl-, substituted by R$^4$, R$^5$, R$^6$ and R$^7$, wherein:

R$^4$ is H, halogen, cyano, (C$_1$-C$_4$)alkyl, halo(C$_1$-C$_4$)alkyl, (C$_1$-C$_4$)alkoxy, phenoxy, phenyl(C$_1$-C$_4$)alkoxy, hydroxyl, hydroxy(C$_1$-C$_4$)alkyl-, or aminocarbonyl, wherein the phenyl moiety of said phenoxy or phenyl(C$_1$-C$_4$)alkoxy- is optionally substituted by 1-3 substituents each independently selected from the group consisting of halogen, —CF$_3$, (C$_1$-C$_4$)alkyl and (C$_1$-C$_4$)alkoxy; and each of R$^5$, R$^6$ and R$^7$ is independently selected from the group consisting of H, hydroxyl, halogen, —CF$_3$, hydroxy (C$_1$-C$_4$)alkyl, (C$_1$-C$_4$)alkyl and (C$_1$-C$_4$)alkoxy; or Z is phenyl substituted by R$^8$, R$^9$ and R$^{10}$, wherein:

R$^8$ and R$^9$ are located on adjacent atoms and taken together with the atoms to which they are attached form a 5-membered heterocyclic group containing 1, 2 or 3 heteroatoms each independently selected from the group consisting of N, O and S, which 5-membered heterocyclic group is substituted by R$^{11}$;

wherein one of R$^{10}$ or R$^{11}$ is H, halogen, cyano, (C$_1$-C$_4$) alkyl, halo(C$_1$-C$_4$)alkyl, (C$_1$-C$_4$)alkoxy, phenoxy, phenyl (C$_1$-C$_4$)alkoxy, hydroxyl, hydroxy(C$_1$-C$_4$)alkyl-, or aminocarbonyl, where the phenyl moiety of said phenoxy or phenyl(C$_1$-C$_4$)alkoxy is optionally substituted by 1-3 substituents each independently selected from the group consisting of halogen, —CF$_3$, (C$_1$-C$_4$)alkyl and (C$_1$-C$_4$)alkoxy; and the other of R$^{10}$ or R$^{11}$ is H, hydroxyl, halogen, —CF$_3$, hydroxy(C$_1$-C$_4$)alkyl, (C$_1$-C$_4$)alkyl or (C$_1$-C$_4$)alkoxy; or Z is pyrazolyl, having the formula:

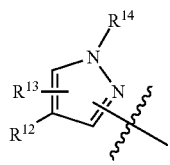

wherein:

R$^{12}$ is methyl or trifluoromethyl (—CH$_3$ or —CF$_3$);

R$^{13}$ is H, methyl or trifluoromethyl (—CH$_3$ or —CF$_3$);

R$^{14}$ is H or (C$_1$-C$_3$)alkyl; or

R$^{12}$ and R$^{13}$, taken together with the atoms to which they are attached, form a 6 membered carbocyclic ring or heterocyclic ring substituted by R$^{15}$ and R$^{16}$, wherein the heterocyclic ring contains 1 nitrogen atom;

wherein R$^{15}$ and R$^{16}$ are each independently selected from the group consisting of H, halogen, cyano, (C$_1$-C$_4$)alkyl, halo(C$_1$-C$_4$)alkyl, (C$_1$-C$_4$)alkoxy, phenoxy, phenyl(C$_1$-C$_4$) alkoxy, hydroxyl, hydroxy(C$_1$-C$_4$)alkyl-, and aminocarbonyl, wherein the phenyl moiety of said phenoxy or phenyl (C$_1$-C$_4$)alkoxy is optionally substituted by 1-3 substituents each independently selected from the group consisting of halogen, —CF$_3$, (C$_1$-C$_4$)alkyl and (C$_1$-C$_4$)alkoxy;

provided that the compound is not N-(4-chloro-2-fluorophenyl)-7-methoxy-6-[(2-methoxyethyl)sulfinyl]-4-quinolinamine or 3-[[7-bromo-6-(methylsulfonyl)-4-quinolinyl] amino]-4-methyl-phenol (See WO 98/13350 and Bioorg. Med. Chem. Lett. (2007), 17(21), 5886-5893);

or a salt, particularly a pharmaceutically acceptable salt, thereof.

In one embodiment of this invention, R$^1$ is H. In other embodiments, R$^1$ is —SO$_2$(C$_1$-C$_4$alkyl) or —CO(C$_1$-C$_4$alkyl); specifically, —SO$_2$CH$_3$ or —COCH$_3$. In other embodiments, R$^1$ is (C$_1$-C$_2$)alkyl; specifically, —CH$_3$. In specific embodiments, R$^1$ is H or —CH$_3$; generally, R$^1$ is H.

In another embodiment, R$^2$ is —SOR$^a$. In yet another embodiment, R$^2$ is —SO$_2$R$^a$.

In a further embodiment, R$^a$ is (C$_1$-C$_6$)alkyl, C$_3$-C$_6$cycloalkyl, 4-6-membered heterocycloalkyl, 5-6-membered heteroaryl or phenyl;

wherein said (C$_1$-C$_6$)alkyl is optionally substituted by for 2 substituents each independently selected from the group consisting of hydroxyl, (C$_1$-C$_4$)alkoxy, (C$_1$-C$_4$)alkoxy(C$_2$-C$_4$)alkoxy-, amino, (C$_1$-C$_4$ alkyl)amino-, (C$_1$-C$_4$ alkyl)(C$_1$-C$_4$ alkyl)amino-, (phenyl)(C$_1$-C$_4$ alkyl)amino-, —CO$_2$(C$_1$-C$_4$)alkyl, —CONH$_2$, —SO$_2$(C$_1$-C$_4$)alkyl, and a C$_3$-C$_6$cycloalkyl, phenyl, 4-6-membered heterocycloalkyl, 5-6-membered heteroaryl, or 9-10-membered heteroaryl, where said C$_3$-C$_6$cycloalkyl, phenyl, 4-6-membered heterocycloalkyl, 5-6-membered heteroaryl, or 9-10-membered heteroaryl is optionally substituted by 1-3 groups each independently selected from the group consisting of halogen, —CF$_3$, hydroxyl, amino, (C$_1$-C$_4$)alkyl, phenyl(C$_1$-C$_4$) alkyl-, hydroxy(C$_1$-C$_4$)alkyl- and (C$_1$-C$_4$)alkoxy; and wherein said C$_3$-C$_6$cycloalkyl, 4-6-membered heterocycloalkyl, 5-6-membered heteroaryl or phenyl is optionally substituted by 1-3 groups each independently selected from the group consisting of halogen, —CF$_3$, hydroxyl, amino, (C$_1$-C$_4$)alkyl, phenyl(C$_1$-C$_4$)alkyl-, hydroxy(C$_1$-C$_4$)alkyl- and (C$_1$-C$_4$)alkoxy.

In a further embodiment, R$^a$ is (C$_1$-C$_6$)alkyl, wherein said (C$_1$-C$_6$)alkyl is optionally substituted by for 2 substituents each independently selected from the group consisting of hydroxyl, (C$_1$-C$_4$)alkoxy, (C$_1$-C$_4$)alkoxy(C$_2$-C$_4$)alkoxy-, amino, (C$_1$-C$_4$ alkyl)amino-, (C$_1$-C$_4$ alkyl)(C$_1$-C$_4$ alkyl) amino-, (phenyl)(C$_1$-C$_4$ alkyl)amino-, —CO$_2$(C$_1$-C$_4$)alkyl, —CONH$_2$, —SO$_2$(C$_1$-C$_4$)alkyl, and a C$_3$-C$_6$cycloalkyl, phenyl, 4-6-membered heterocycloalkyl, 5-6-membered heteroaryl, or 9-10-membered heteroaryl, where said C$_3$-C$_6$cycloalkyl, phenyl, 4-6-membered heterocycloalkyl, 5-6-membered heteroaryl, or 9-10-membered heteroaryl is optionally substituted by 1-3 groups each independently selected from the group consisting of halogen, —CF$_3$, hydroxyl, amino, $(C_1-C_4)$alkyl, phenyl$(C_1-C_4)$alkyl-, hydroxy$(C_1-C_4)$alkyl- and $(C_1-C_4)$alkoxy.

In a further embodiment, $R^a$ is $C_3-C_6$cycloalkyl, 4-6-membered heterocycloalkyl, 5-6-membered heteroaryl or phenyl, wherein said $C_3-C_6$cycloalkyl, 4-6-membered heterocycloalkyl, 5-6-membered heteroaryl or phenyl is optionally substituted by 1-3 groups each independently selected from the group consisting of halogen, —$CF_3$, hydroxyl, amino, $(C_1-C_4)$alkyl, phenyl$(C_1-C_4)$alkyl-, hydroxy$(C_1-C_4)$alkyl- and $(C_1-C_4)$alkoxy.

When $R^a$ is a heterocycloalkyl or heteroaryl group, it is to be understood that the heterocycloalkyl or heteroaryl group is bonded to the sulfur atom of the —$SOR^a$ or —$SO_2R^a$ moiety by a ring carbon atom.

In a still further embodiment, $R^a$ is $(C_1-C_4)$alkyl, wherein said $(C_1-C_4)$alkyl is optionally substituted by for 2 substituents each independently selected from the group consisting of hydroxyl, $(C_1-C_2)$alkoxy, $(C_1-C_2)$alkoxy$(C_2-C_3)$alkoxy-, amino, $(C_1-C_3$ alkyl)amino-, $(C_1-C_3$ alkyl)$(C_1-C_2$ alkyl)amino-, $C_3-C_6$cycloalkyl (optionally substituted by $(C_1-C_4)$alkyl or hydroxy$(C_1-C_4)$alkyl), 4-6-membered heterocycloalkyl (optionally substituted by $(C_1-C_4)$alkyl), 5-6-membered heteroaryl (optionally substituted by $(C_1-C_4)$alkyl), phenyl, or 9-10-membered heteroaryl.

In a still further embodiment, $R^a$ is $C_3-C_6$cycloalkyl, 4-6-membered heterocycloalkyl, 5-6-membered heteroaryl or phenyl, wherein:

said $C_3-C_6$cycloalkyl is optionally substituted by for 2 substituents each independently selected from the group consisting of hydroxyl, $(C_1-C_4)$alkyl, $(C_1-C_2)$alkoxy, $(C_1-C_2)$alkoxy$(C_2-C_3)$alkoxy-, amino, $(C_1-C_3$ alkyl)amino-, and $(C_1-C_3$ alkyl)$(C_1-C_2$ alkyl)amino-, said 4-6-membered heterocycloalkyl is optionally substituted by 1 or 2 groups independently selected from the group consisting of $(C_1-C_4)$alkyl or benzyl, wherein the 4-6 membered heterocycloalkyl contains one heteroatom selected from the group consisting of N, O and S, said 5-6-membered heteroaryl is optionally substituted by $(C_1-C_4)$alkyl or hydroxy$(C_1-C_4)$alkyl, wherein the 5-6 membered heteroaryl contains one heteroatom selected from the group consisting of N, O and S or contains one nitrogen atom and a second one heteroatom selected from the group consisting of N, O and S optionally contains additional heteroatom nitrogen atom, and said phenyl is optionally substituted by amino.

In a still further embodiment, $R^a$ is $(C_1-C_4)$alkyl wherein said $(C_1-C_4)$alkyl is optionally substituted by for 2 substituents each independently selected from the group consisting of hydroxyl, $(C_1-C_2)$alkoxy, $(C_1-C_2)$alkoxy$(C_2-C_3)$alkoxy-, amino, $(C_1-C_3$ alkyl)amino-, $(C_1-C_3$ alkyl)$(C_1-C_2$ alkyl)amino-, $C_3-C_6$cycloalkyl (optionally substituted by $(C_1-C_4)$alkyl or hydroxy$(C_1-C_4)$alkyl), 4-6-membered heterocycloalkyl (optionally substituted by $(C_1-C_4)$alkyl), 5-6-membered heteroaryl (optionally substituted by $(C_1-C_4)$alkyl), phenyl, and 9-10-membered heteroaryl.

In a still further embodiment, $R^a$ is $(C_1-C_4)$alkyl wherein said $(C_1-C_4)$alkyl is optionally substituted by a substituent selected from the group consisting of hydroxyl, $(C_1-C_2)$alkoxy, $(C_1-C_2)$alkoxy$(C_2-C_3)$alkoxy-, amino, $(C_1-C_3$ alkyl)amino-, and $(C_1-C_3$ alkyl)$(C_1-C_2$ alkyl)amino-.

In a still further embodiment, $R^a$ is $C_3-C_6$cycloalkyl wherein said $C_3-C_6$cycloalkyl is optionally substituted by for 2 substituents each independently selected from the group consisting of hydroxyl, $(C_1-C_4)$alkyl, $(C_1-C_2)$alkoxy, $(C_1-C_2)$alkoxy$(C_2-C_3)$alkoxy-, amino, $(C_1-C_3$ alkyl)amino-, and $(C_1-C_3$ alkyl)$(C_1-C_2$ alkyl)amino-.

In a still further embodiment, $R^a$ is 4-6-membered heterocycloalkyl wherein said 4-6-membered heterocycloalkyl is optionally substituted by 1 or 2 groups independently selected from the group consisting of $(C_1-C_4)$alkyl or benzyl, wherein the 4-6 membered heterocycloalkyl contains one heteroatom selected from the group consisting of N, O and S.

In a still further embodiment, $R^a$ is 5-6 membered heterocycloalkyl optionally substituted by 1 or 2 independently selected $(C_1-C_4)$alkyl groups, wherein the 5-6 membered heterocycloalkyl contains one heteroatom selected from the group consisting of N, O and S. In specific embodiments, the optionally substituted 5-6 membered heterocycloalkyl contains one oxygen heteroatom.

In a still further embodiment, $R^a$ is 5-6-membered heteroaryl wherein said 5-6-membered heteroaryl is optionally substituted by $(C_1-C_4)$alkyl or hydroxy$(C_1-C_4)$alkyl, wherein the 5-6 membered heteroaryl contains one heteroatom selected from the group consisting of N, O and S or contains one nitrogen atom and a second heteroatom selected from the group consisting of N, O and S and optionally contains one additional nitrogen atom. In a still further embodiment, $R^a$ is 6-membered heteroaryl optionally substituted by $(C_1-C_4)$alkyl or hydroxy$(C_1-C_4)$alkyl, wherein the 6 membered heteroaryl contains one or two nitrogen atoms.

In a still further embodiment, $R^a$ is phenyl, wherein said phenyl is optionally substituted by amino.

In a still further embodiment, $R^a$ is a 5-6-membered heterocycloalkyl, wherein said 5-6-membered heterocycloalkyl is optionally substituted by 1 or 2 independently selected $(C_1-C_4)$alkyl groups; wherein the 5-6 membered heterocycloalkyl group contains 1 heteroatom selected from the group consisting of N, O and S.

In a still further embodiment, $R^a$ is $(C_1-C_4)$alkyl, tetrahydrofuranyl, tetrahydropyranyl or piperidinyl, wherein:

said $(C_1-C_4)$alkyl is optionally substituted by a substituent selected from the group consisting of hydroxyl, $(C_1-C_2)$alkoxy, $(C_1-C_2)$alkoxy$(C_2-C_3)$alkoxy-, amino, $(C_1-C_3$ alkyl)amino-, $(C_1-C_3$ alkyl)$(C_1-C_2$ alkyl)amino-, and a $C_3-C_6$cycloalkyl (optionally substituted by $(C_1-C_4)$alkyl or hydroxy$(C_1-C_4)$alkyl), and said tetrahydrofuranyl, tetrahydropyranyl or piperidinyl is optionally substituted by 1 or 2 groups independently selected from the group consisting of halogen, —$CF_3$, hydroxyl, amino, $(C_1-C_4)$alkyl, phenyl$(C_1-C_4)$alkyl-, hydroxy$(C_1-C_4)$alkyl- and $(C_1-C_4)$alkoxy.

In another embodiment, $R^a$ is an unsubstituted $(C_1-C_4)$alkyl or a $(C_1-C_4)$alkyl substituted by a substituent selected from the group consisting of hydroxyl, $(C_1-C_2)$alkoxy, and $(C_1-C_2)$alkoxy$(C_2-C_3)$alkoxy-. In yet another embodiment, $R^a$ is tetrahydropyranyl, wherein the tetrahydropyranyl group is optionally substituted by 1 or 2 independently selected $(C_1-C_4)$alkyl groups. In still another embodiment, $R^a$ is tetrahydrofuranyl, wherein the tetrahydrofuranyl group is optionally substituted by 1 or 2 independently selected $(C_1-C_4)$alkyl groups. In still another embodiment, $R^a$ is piperidinyl, wherein the piperidinyl group is optionally substituted by 1 or 2 independently selected $(C_1-C_4)$alkyl groups.

In specific embodiments, $R^a$ is —$CH_3$, —$CH(CH_3)_2$, —$C(CH_3)_3$, —$CH_2CH_2OH$, —$C(CH_3)_2CH_2OH$, —$CH_2CH_2OCH_3$, tetrahydro-2H-pyran-4-yl, 2,2-dimethyltetrahydro-2H-pyran-4-yl, 4-methyltetrahydro-2H-pyran-4-yl, (3R,4R)-3-methyltetrahydro-2H-pyran-4-yl, or (2R,6S)-2,6-dimethyltetrahydro-2H-pyran-4-yl.

In selected embodiments, $R^a$ is —$CH_3$, —$CH(CH_3)_2$, —$C(CH_3)_3$, —$CH_2CH_2OH$, or tetrahydro-2H-pyran-4-yl. In other specific embodiments, $R^a$ is —$CH_2CH_3$, —$CH_2CH_2OCH_3$, —$CH_2CH_2CH_2OH$, tetrahydrofuran-3-yl, or 1-methyl-piperidin-4-yl-.

In another embodiment, $R^3$ is halogen, hydroxy, $(C_1-C_4)$alkyl-, halo$(C_1-C_4)$alkyl-, $(C_1-C_4)$alkoxy-, halo$(C_1-C_4)$alkoxy-, $(C_1-C_4)$alkoxy$(C_1-C_6)$alkyl-, $(C_1-C_4)$alkoxy$(C_2-C_6)$alkoxy-, hydroxy$(C_1-C_4)$alkyl-, or hydroxy$(C_2-C_6)$alkoxy-. In yet another embodiment, $R^3$ is halogen, hydroxy, $(C_1-C_4)$alkyl-, halo$(C_1-C_4)$alkyl-, $(C_1-C_4)$alkoxy-, $(C_1-C_4)$alkoxy$(C_1-C_6)$alkyl-, $(C_1-C_4)$alkoxy$(C_2-C_6)$alkoxy-, hydroxy$(C_1-C_4)$alkyl-, or hydroxy$(C_2-C_6)$alkoxy-. In a further embodiment, $R^3$ is halogen, hydroxy, $(C_1-C_3)$alkyl-, halo$(C_1-C_2)$alkyl-, $(C_1-C_3)$alkoxy-, halo$(C_1-C_3)$alkoxy-, $(C_1-C_3)$alkoxy$(C_1-C_3)$alkyl-, $(C_1-C_3)$alkoxy$(C_2-C_3)$alkoxy-, hydroxy$(C_1-C_3)$alkyl-, or hydroxy$(C_2-C_3)$alkoxy-. In a further embodiment, $R^3$ is halogen, hydroxy, $(C_1-C_3)$alkyl-, halo$(C_1-C_2)$alkyl-, $(C_1-C_3)$alkoxy-, $(C_1-C_3)$alkoxy$(C_1-C_3)$alkyl-, $(C_1-C_3)$alkoxy$(C_2-C_3)$alkoxy-, hydroxy$(C_1-C_3)$alkyl-, or hydroxy$(C_2-C_3)$alkoxy-. In a selected embodiment, $R^3$ is chloro, bromo, methyl, ethyl, trifluoromethyl, hydroxy, methoxy, difluoromethoxy, ethoxy, or 2-hydroxyethoxy-. In a specific embodiment, $R^3$ is chloro, bromo, methyl, ethyl, trifluoromethyl, hydroxy, methoxy, ethoxy or hydroxyethoxy-.

In another embodiment, Z is phenyl or phenyl$(C_1-C_4)$alkyl-, wherein any phenyl (including the phenyl moiety of phenyl$(C_1-C_4)$alkyl-) is substituted by $R^4$, $R^5$, $R^6$ and $R^7$ wherein:

$R^4$ is H, halogen, cyano, $(C_1-C_4)$alkyl, halo$(C_1-C_4)$alkyl, $(C_1-C_4)$alkoxy, phenoxy, phenyl$(C_1-C_4)$alkoxy, hydroxyl, hydroxy$(C_1-C_4)$alkyl- or aminocarbonyl, wherein the phenyl moiety of said phenoxy or phenyl$(C_1-C_4)$alkoxy- is optionally substituted by 1-3 substituents each independently selected from the group consisting of halogen, —$CF_3$, $(C_1-C_4)$alkyl and $(C_1-C_4)$alkoxy; and each of $R^5$, $R^6$ and $R^7$ is independently selected from the group consisting of H, hydroxyl, halogen, hydroxy$(C_1-C_4)$alkyl, $(C_1-C_4)$alkyl, halo$(C_1-C_4)$alkyl and $(C_1-C_4)$alkoxy.

Specifically, Z is phenyl, substituted by 1, 2 or 3 substituents each independently selected from the group consisting of hydroxyl, halogen, —$CF_3$, hydroxy$(C_1-C_4)$alkyl, $(C_1-C_4)$alkyl and $(C_1-C_4)$alkoxy.

More specifically, Z is phenyl, having the formula:

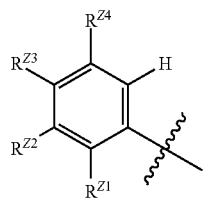

wherein:
$R^{Z1}$ is H, halogen, —$CF_3$, $(C_1-C_4)$alkyl or $(C_1-C_4)$alkoxy; particularly, $R^{Z1}$ is H or methyl;
$R^{Z2}$ is H, halogen, —$CF_3$, $(C_1-C_4)$alkyl or $(C_1-C_4)$alkoxy;
$R^{Z3}$ is H, halogen, cyano, $(C_1-C_4)$alkyl, halo$(C_1-C_4)$alkyl, $(C_1-C_4)$alkoxy, phenoxy, phenyl$(C_1-C_4)$alkoxy, hydroxyl, hydroxy$(C_1-C_4)$alkyl-, or aminocarbonyl, wherein the phenyl moiety of said phenoxy or phenyl$(C_1-C_4)$alkoxy- is optionally substituted by 1-3 substituents each independently selected from the group consisting of halogen, —$CF_3$, $(C_1-C_4)$alkyl and $(C_1-C_4)$alkoxy; and $R^{Z4}$ is hydroxyl, hydroxy$(C_1-C_4)$alkyl or $(C_1-C_4)$alkoxy. In a more specific embodiment, Z is 3-methoxy-4-chlorophenyl or 2-methyl-5-(hydroxymethyl)-phenyl.

In yet another embodiment, Z is phenyl substituted by $R^8$, $R^9$ and $R^{10}$, wherein:

$R^8$ and $R^9$ are located on adjacent atoms and taken together with the atoms to which they are attached form a 5-membered heterocyclic group containing 1, 2 or 3 heteroatoms each independently selected from the group consisting of N, O and S, which 5-membered heterocyclic group is substituted by $R^{11}$;

wherein one of $R^{10}$ or $R^{11}$ is H, halogen, cyano, $(C_1-C_4)$alkyl, —$CF_3$, $(C_1-C_4)$alkoxy, phenoxy, phenyl$(C_1-C_4)$alkoxy, hydroxyl, hydroxy$(C_1-C_4)$alkyl-, or aminocarbonyl, where the phenyl moiety of said phenoxy or phenyl$(C_1-C_4)$alkoxy is optionally substituted by 1-3 substituents each independently selected from the group consisting of halogen, —$CF_3$, $(C_1-C_4)$alkyl and $(C_1-C_4)$alkoxy, and the other of $R^{10}$ or $R^{11}$ is H, hydroxyl, halogen, —$CF_3$, hydroxy$(C_1-C_4)$alkyl, $(C_1-C_4)$alkyl or $(C_1-C_4)$alkoxy.

Specifically, Z is benzothiazolyl, optionally substituted by for 2 substituents each independently selected from the group consisting of halogen, $(C_1-C_4)$alkyl, —$CF_3$, and $(C_1-C_4)$alkoxy. More specifically, Z is an optionally substituted benzothiazol-6-yl optionally substituted by chloro, fluoro, —$CF_3$, methyl, or methoxy. In a specific embodiment, Z is benzothiazol-6-yl.

In yet another embodiment, Z is pyridyl substituted by $R^8$, $R^9$ and $R^{10}$, wherein:

$R^8$ and $R^9$ are located on adjacent atoms and taken together with the atoms to which they are attached form a 5-membered heterocyclic group containing 1, 2 or 3 heteroatoms each independently selected from the group consisting of N, O and S, which 5-membered heterocyclic group is substituted by $R^{11}$;

wherein one of $R^{10}$ or $R^{11}$ is H, halogen, cyano, $(C_1-C_4)$alkyl, —$CF_3$, $(C_1-C_4)$alkoxy, phenoxy, phenyl$(C_1-C_4)$alkoxy, hydroxyl, hydroxy$(C_1-C_4)$alkyl-, or aminocarbonyl, where the phenyl moiety of said phenoxy or phenyl$(C_1-C_4)$alkoxy is optionally substituted by 1-3 substituents each independently selected from the group consisting of halogen, —$CF_3$, $(C_1-C_4)$alkyl and $(C_1-C_4)$alkoxy and the other of $R^{10}$ or $R^{11}$ is H, hydroxyl, halogen, —$CF_3$, hydroxy$(C_1-C_4)$alkyl, $(C_1-C_4)$alkyl or $(C_1-C_4)$alkoxy.

In another embodiment, Z is pyrazolyl, $R^{12}$ is methyl or trifluoromethyl, $R^{13}$ is H, methyl, or trifluoromethyl, and $R^{14}$ is H or methyl. In a further embodiment, Z is pyrazolyl, $R^{12}$ and $R^{13}$ are independently selected from the group consisting of methyl and trifluoromethyl, and $R^{14}$ is H or methyl. In a specific embodiment, Z is pyrazolyl, $R^{12}$ is methyl, $R^{13}$ is methyl or trifluoromethyl, and $R^{14}$ is H.

In a still further embodiment, Z is pyrazolyl, substituted by $R^{12}$ and $R^{13}$ wherein:

$R^{12}$ and $R^{13}$ are located on adjacent carbon atoms and taken together with the atoms to which they are attached form a 6 membered carbocyclic ring or heterocyclic ring substituted by $R^{15}$ and $R^{16}$;

wherein $R^{15}$ is H, halogen, cyano, $(C_1-C_4)$alkyl, —$CF_3$, $(C_1-C_4)$alkoxy, phenoxy, phenyl$(C_1-C_4)$alkoxy, hydroxyl, hydroxy$(C_1-C_4)$alkyl-, or aminocarbonyl, wherein the phenyl moiety of said phenoxy or phenyl$(C_1-C_4)$alkoxy is optionally substituted by 1-3 substituents each independently selected from the group consisting of halogen, —$CF_3$, $(C_1-C_4)$alkyl and $(C_1-C_4)$alkoxy; and $R^{16}$ is H, hydroxyl, halogen, —$CF_3$, hydroxy$(C_1-C_4)$alkyl, $(C_1-C_4)$alkyl or $(C_1-C_4)$alkoxy.

In another embodiment, the invention is directed to a compound according to Formula (I), wherein Z is a 9-membered bi-cyclic heteroaryl group, wherein the 9-membered bi-cyclic heteroaryl group is an optionally substituted indazolyl or pyrazolo[3,4-b]pyridinyl, bonded to the quinolyl-amino (NR$^1$) moiety via a substitutable carbon ring atom of the 5-membered (pyrazolyl) ring moiety of the indazolyl or pyrazolo[3,4-b]pyridinyl group, wherein the indazolyl or pyrazolo[3,4-b]pyridinyl is substituted on the 6-membered (phenyl or pyridyl) ring moiety thereof by 1 or 2 substituents each independently selected from the group consisting of hydroxyl, halogen, —CF$_3$, hydroxy(C$_1$-C$_4$)alkyl, (C$_1$-C$_4$) alkyl and (C$_1$-C$_4$)alkoxy, or a salt, particularly a pharmaceutically acceptable salt, thereof.

In a further embodiment, Z is an optionally substituted indazolyl or pyrazolo[3,4-b]pyridinyl group, where the Z group is optionally substituted by 1 or 2 substituents each independently selected from the group consisting of chloro, fluoro, methyl, and methoxy. In specific embodiments, Z is 4-chloro-1H-indazol-3-yl, 5-chloro-1H-indazol-3-yl, 6-chloro-1H-indazol-3-yl, 7-chloro-1H-indazol-3-yl, 5-fluoro-1H-indazol-3-yl, 7-fluoro-1H-indazol-3-yl, 5-,7-difluoro-1H-indazol-3-yl, 6,7-difluoro-1H-indazol-3-yl, 5-methoxy-1H-indazol-3-yl or 5-fluoro-1H-pyrazolo[3,4-b]pyridin-3-yl.

In another embodiment, the invention is directed to a compound according to Formula (II):

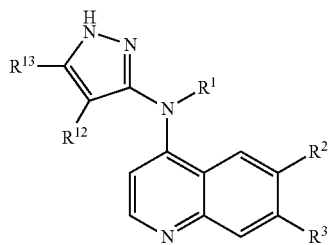

(II)

or a salt, particularly a pharmaceutically acceptable salt thereof, wherein R$^1$, R$^2$, R$^3$, R$^{12}$ and R$^{13}$ are as defined herein.

In another embodiment, the invention is directed to method of inhibiting RIP2 kinase comprising contacting the kinase with a compound according to Formula (III):

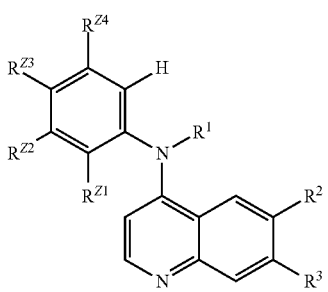

(III)

or a salt, particularly a pharmaceutically acceptable salt thereof, wherein R$^1$, R$^2$ and R$^3$ are as defined herein, and R$^{Z1}$ is H, halogen, —CF$_3$, (C$_1$-C$_4$)alkyl or (C$_1$-C$_4$)alkoxy; particularly, R$^{Z1}$ is H R$^{Z2}$ is H, H halogen, —CF$_3$, (C$_1$-C$_4$)alkyl or (C$_1$-C$_4$)alkoxy;

R$^{Z3}$ is H, halogen, cyano, (C$_1$-C$_4$)alkyl, halo(C$_1$-C$_4$)alkyl, (C$_1$-C$_4$)alkoxy, phenoxy, phenyl(C$_1$-C$_4$)alkoxy, hydroxyl, hydroxy(C$_1$-C$_4$)alkyl-, or aminocarbonyl, wherein the phenyl moiety of said phenoxy or phenyl(C$_1$-C$_4$)alkoxy- is optionally substituted by 1-3 substituents each independently selected from the group consisting of halogen, —CF$_3$, (C$_1$-C$_4$)alkyl and (C$_1$-C$_4$)alkoxy; and R$^{Z4}$ is hydroxyl, hydroxy(C$_1$-C$_4$)alkyl or (C$_1$-C$_4$)alkoxy.

In a compound, or salt thereof, of Formula (I), (II) and (III):

R$^1$ is H;

R$^2$ is —SOR$^a$, or —SO$_2$R$^a$, and R$^a$ is (C$_1$-C$_4$)alkyl or a 5-6-membered heterocycloalkyl, wherein said (C$_1$-C$_4$)alkyl is optionally substituted by a substituent selected from the group consisting of hydroxyl, (C$_1$-C$_2$)alkoxy, (C$_1$-C$_2$)alkoxy (C$_2$-C$_3$)alkoxy-, amino, (C$_1$-C$_3$ alkyl)amino-, and (C$_1$-C$_3$ alkyl)(C$_1$-C$_2$ alkyl)amino-, and said 5-6-membered heterocycloalkyl is optionally substituted by 1 or 2 independently selected (C$_1$-C$_4$)alkyl groups, wherein the 5-6 membered heterocycloalkyl group contains 1 heteroatom selected from the group consisting of N, O and S; and R$^3$ is halogen, hydroxy, (C$_1$-C$_3$)alkyl-, halo(C$_1$-C$_2$)alkyl-, (C$_1$-C$_3$)alkoxy-, (C$_1$-C$_3$)alkoxy(C$_1$-C$_3$)alkyl-, (C$_1$-C$_3$)alkoxy(C$_2$-C$_3$)alkoxy-, hydroxy(C$_1$-C$_3$)alkyl-, or hydroxy(C$_2$-C$_3$)alkoxy-.

In a compound, or salt thereof, of Formula (I), (II) and (III):

R$^1$ is H;

R$^2$ is —SOR$^a$, or —SO$_2$R$^a$, and R$^a$ is —CH$_3$, —CH(CH$_3$)$_2$, —C(CH$_3$)$_3$, —CH$_2$CH$_2$OH, or tetrahydro-2H-pyran-4-yl; and R$^3$ is chloro, bromo, methyl, ethyl, trifluoromethyl, hydroxy, methoxy or ethoxy. In a compound, or salt thereof, of Formula (I), (II) and (III):

R$^1$ is H;

R$^2$ is —SOR$^a$, or —SO$_2$R$^a$, and R$^a$ is —CH$_3$, —CH(CH$_3$)$_2$, —C(CH$_3$)$_3$, —CH$_2$CH$_2$OH, —C(CH$_3$)$_2$CH$_2$OH, —CH$_2$CH$_2$OCH$_3$, tetrahydro-2H-pyran-4-yl, 2,2-dimethyltetrahydro-2H-pyran-4-yl, 4-methyltetrahydro-2H-pyran-4-yl, (3R,4R)-3-methyltetrahydro-2H-pyran-4-yl, or (2R,6S)-2,6-dimethyltetrahydro-2H-pyran-4-yl; and R$^3$ is chloro, bromo, methyl, ethyl, trifluoromethyl, hydroxy, methoxy, difluoromethoxy, ethoxy, or 2-hydroxyethoxy-.

In one embodiment of a compound, or salt thereof, of Formula (I), as defined above, Z is 3-methoxy-4-chloro-phenyl or 2-methyl-5-(hydroxymethyl)-phenyl.

In another embodiment of a compound, or salt thereof, of Formula (I), as defined above, Z is pyrazolyl, R$^{12}$ is methyl, R$^{13}$ is methyl or trifluoromethyl, and R$^{14}$ is H.

In yet another embodiment of a compound, or salt thereof, of Formula (I), as defined above, Z is benzothiazol-6-yl.

In still another embodiment of a compound, or salt thereof, of Formula (I), as defined above, Z is 4-chloro-1H-indazol-3-yl, 5-chloro-1H-indazol-3-yl, 6-chloro-1H-indazol-3-yl, 7-chloro-1H-indazol-3-yl, 5-fluoro-1H-indazol-3-yl, 7-fluoro-1H-indazol-3-yl, 5-,7-difluoro-1H-indazol-3-yl, 6,7-difluoro-1H-indazol-3-yl, 5-methoxy-1H-indazol-3-yl or 5-fluoro-1H-pyrazolo[3,4-b]pyridin-3-yl.

Specific compounds of this invention are:
6-(tert-butylsulfonyl)-N-(4,5-dimethyl-1H-pyrazol-3-yl)-7-methoxyquinolin-4-amine;
N-(4,5-dimethyl-1H-pyrazol-3-yl)-7-(methyloxy)-6-(tetrahydro-2H-pyran-4-ylsulfinyl)-4-quinolinamine;
6-[(1,1-dimethylethyl)sulfinyl]-N-(4,5-dimethyl-1H-pyrazol-3-yl)-7-(methyloxy)-4-quinolinamine;

2-((4-((4,5-dimethyl-1H-pyrazol-3-yl)amino)-7-methoxyquinolin-6-yl)sulfonyl)-2-methylpropan-1-ol;
N-(4,5-dimethyl-1H-pyrazol-3-yl)-7-methoxy-6-((tetrahydro-2H-pyran-4-yl)sulfonyl)quinolin-4-amine;
2-((4-((4,5-dimethyl-1H-pyrazol-3-yl)amino)-7-methylquinolin-6-yl)sulfonyl)ethanol;
N-(4,5-dimethyl-1H-pyrazol-3-yl)-6-((2,2-dimethyltetrahydro-2H-pyran-4-yl)sulfonyl)-7-methoxyquinolin-4-amine;
N-(4,5-dimethyl-1H-pyrazol-3-yl)-7-methoxy-6-((4-methyltetrahydro-2H-pyran-4-yl)sulfonyl)quinolin-4-amine;
N-(4,5-dimethyl-1H-pyrazol-3-yl)-7-methoxy-6-((2-methoxyethyl)sulfonyl)quinolin-4-amine;
N-(4,5-dimethyl-1H-pyrazol-3-yl)-7-methoxy-6-(((3R,4R)-3-methyltetrahydro-2H-pyran-4-yl)sulfonyl)quinolin-4-amine;
N-(4,5-dimethyl-1H-pyrazol-3-yl)-6-(((2R,6S)-2,6-dimethyltetrahydro-2H-pyran-4-yl)sulfonyl)-7-methoxyquinolin-4-amine;
6-(tert-butylsulfonyl)-N-(5-fluoro-1H-pyrazolo[3,4-b]pyridin-3-yl)-7-methoxyquinolin-4-amine;
N-[4-chloro-3-(methyloxy)phenyl]-6-[(1,1-dimethyl ethyl)sulfonyl]-7-(methyloxy)-4-quinolinamine;
N-[4-chloro-3-(methyloxy)phenyl]-7-(methyloxy)-6-(tetrahydro-2H-pyran-4-ylsulfonyl)-4-quinolinamine;
N-1,3-benzothiazol-5-yl-7-(methyloxy)-6-(tetrahydro-2H-pyran-4-ylsulfonyl)-4-quinolinamine;
2-{[4-{[4-chloro-3-(methyloxy)phenyl]amino}-7-(methyloxy)-6-quinolinyl]sulfonyl}ethanol;
N-(5-fluoro-1H-indazol-3-yl)-7-(methyloxy)-6-(tetrahydro-2H-pyran-4-ylsulfonyl)-4-quinolinamine;
2-{[4-[(4,5-dimethyl-1H-pyrazol-3-yl)amino]-7-(methyloxy)-6-quinolinyl]sulfonyl}ethanol;
N-[4-chloro-3-(methyloxy)phenyl]-6-[(1-methylethyl) sulfonyl]-7-(methyloxy)-4-quinolinamine;
N-1,3-benzothiazol-5-yl-6-[(1-methylethyl) sulfonyl]-7-(methyloxy)-4-quinolinamine;
N-(4,5-dimethyl-1H-pyrazol-3-yl)-6-[(1-methylethyl) sulfonyl]-7-(methyloxy)-4-quinolinamine;
N-(5-fluoro-1H-indazol-3-yl)-6-[(1-methylethyl) sulfonyl]-7-(methyloxy)-4-quinolinamine;
2-{[4-(1,3-benzothiazol-5-ylamino)-7-(methyloxy)-6-quinolinyl]sulfonyl}ethanol;
6-(isopropylsulfonyl)-7-methoxy-N-(4-methyl-5-(trifluoromethyl)-1H-pyrazol-3-yl)quinolin-4-amine;
6-(tert-butylsulfonyl)-7-methoxy-N-(4-methyl-5-(trifluoromethyl)-1H-pyrazol-3-yl)quinolin-4-amine;
6-(tert-butylsulfonyl)-N-(4,5-dimethyl-1H-pyrazol-3-yl)-7-ethoxyquinolin-4-amine;
6-(tert-butylsulfonyl)-7-ethoxy-N-(5-fluoro-1H-indazol-3-yl)quinolin-4-amine;
7-chloro-N-(4,5-dimethyl-1H-pyrazol-3-yl)-6-((tetrahydro-2H-pyran-4-yl)sulfonyl)quinolin-4-amine;
N-(4,5-dimethyl-1H-pyrazol-3-yl)-7-methyl-6-((tetrahydro-2H-pyran-4-yl)sulfonyl)quinolin-4-amine;
7-chloro-N-(5-fluoro-1H-indazol-3-yl)-6-((tetrahydro-2H-pyran-4-yl)sulfonyl)quinolin-4-amine;
N-(5-fluoro-1H-indazol-3-yl)-7-methyl-6-((tetrahydro-2H-pyran-4-yl)sulfonyl)quinolin-4-amine;
N-(5-fluoro-1H-indazol-3-yl)-6-((tetrahydro-2H-pyran-4-yl)sulfonyl)-7-(trifluoromethyl) quinolin-4-amine;
6-(tert-butylsulfonyl)-N-(5-fluoro-1H-indazol-3-yl)-7-(trifluoromethyl)quinolin-4-amine;
6-(tert-butylsulfonyl)-N-(4,5-dimethyl-1H-pyrazol-3-yl)-7-methylquinolin-4-amine;
6-(tert-butylsulfonyl)-N-(5-fluoro-1H-indazol-3-yl)-7-methylquinolin-4-amine;
6-(tert-butylsulfonyl)-N-(5-fluoro-1H-indazol-3-yl)-7-methoxyquinolin-4-amine;
6-(tert-butylsulfonyl)-7-chloro-N-(5-fluoro-1H-indazol-3-yl)quinolin-4-amine;
6-(tert-butylsulfonyl)-7-ethyl-N-(5-fluoro-1H-indazol-3-yl)quinolin-4-amine;
N-(5-fluoro-1H-indazol-3-yl)-6-(isopropylsulfonyl)-7-methylquinolin-4-amine;
N-(4,5-dimethyl-1H-pyrazol-3-yl)-6-(isopropylsulfonyl)-7-methylquinolin-4-amine;
6-(tert-butylsulfonyl)-N-(4,5-dimethyl-1H-pyrazol-3-yl)-7-ethylquinolin-4-amine;
7-ethyl-N-(5-fluoro-1H-indazol-3-yl)-6-((tetrahydro-2H-pyran-4-yl)sulfonyl)quinolin-4-amine;
N-(4,5-dimethyl-1H-pyrazol-3-yl)-7-ethyl-6-((tetrahydro-2H-pyran-4-yl)sulfonyl)quinolin-4-amine;
(3-(6-(tert-butylsulfonyl)-7-methoxyquinolin-4-yl)amino)-4-methylphenyl)methanol;
7-ethoxy-N-(5-fluoro-1H-indazol-3-yl)-6-(isopropylsulfonyl)quinolin-4-amine;
N-(7-chloro-1H-indazol-3-yl)-7-methoxy-6-((tetrahydro-2H-pyran-4-yl)sulfonyl)quinolin-4-amine;
6-(tert-butylsulfonyl)-N-(7-fluoro-1H-indazol-3-yl)-7-methoxyquinolin-4-amine;
6-(tert-butylsulfonyl)-N-(5,7-difluoro-1H-indazol-3-yl)-7-methoxyquinolin-4-amine;
6-(tert-butylsulfonyl)-N-(6,7-difluoro-1H-indazol-3-yl)-7-methoxyquinolin-4-amine;
6-(tert-butylsulfonyl)-N-(7-chloro-1H-indazol-3-yl)-7-methoxyquinolin-4-amine;
6-(tert-butylsulfonyl)-7-methoxy-N-(5-methoxy-1H-indazol-3-yl)quinolin-4-amine;
6-(tert-butylsulfonyl)-N-(7-fluoro-1H-indazol-3-yl)-7-methylquinolin-4-amine;
6-(tert-butylsulfonyl)-N-(5,7-difluoro-1H-indazol-3-yl)-7-methylquinolin-4-amine;
6-(tert-butylsulfonyl)-N-(5-methoxy-1H-indazol-3-yl)-7-methylquinolin-4-amine;
6-(tert-butylsulfonyl)-N-(6,7-difluoro-1H-indazol-3-yl)-7-methylquinolin-4-amine;
6-(tert-butylsulfonyl)-N-(7-chloro-1H-indazol-3-yl)-7-methylquinolin-4-amine;
7-methoxy-N-(4-methyl-5-(trifluoromethyl)-1H-pyrazol-3-yl)-6-((tetrahydro-2H-pyran-4-yl)sulfonyl)quinolin-4-amine;
N-(5,7-difluoro-1H-indazol-3-yl)-7-methoxy-6-((tetrahydro-2H-pyran-4-yl)sulfonyl)quinolin-4-amine;
N-(4-chloro-1H-indazol-3-yl)-7-methoxy-6-((tetrahydro-2H-pyran-4-yl)sulfonyl)quinolin-4-amine;
N-(6-chloro-1H-indazol-3-yl)-7-methoxy-6-((tetrahydro-2H-pyran-4-yl)sulfonyl)quinolin-4-amine;
N-(6,7-difluoro-1H-indazol-3-yl)-7-methoxy-6-((tetrahydro-2H-pyran-4-yl)sulfonyl)quinolin-4-amine;
7-methoxy-N-(5-methoxy-1H-indazol-3-yl)-6-((tetrahydro-2H-pyran-4-yl)sulfonyl)quinolin-4-amine;
N-(5-chloro-1H-indazol-3-yl)-7-methoxy-6-((tetrahydro-2H-pyran-4-yl)sulfonyl)quinolin-4-amine;
N-(7-chloro-1H-indazol-3-yl)-7-methoxy-6-((4-methyltetrahydro-2H-pyran-4-yl)sulfonyl)quinolin-4-amine;
N-1,3-benzothiazol-5-yl-6-(methylsulfonyl)-4-quinolinamine;
7-bromo-N-(4,5-dimethyl-1H-pyrazol-3-yl)-6-((tetrahydro-2H-pyran-4-yl)sulfonyl)quinolin-4-amine;
7-bromo-6-(tert-butylsulfonyl)-N-(4,5-dimethyl-1H-pyrazol-3-yl)quinolin-4-amine;

7-bromo-N-(4-methyl-5-(trifluoromethyl)-1H-pyrazol-3-yl)-6-((tetrahydro-2H-pyran-4-yl)sulfonyl)quinolin-4-amine;
7-bromo-N-(4,5-dimethyl-1H-pyrazol-3-yl)-6-(isopropylsulfonyl)quinolin-4-amine;
7-bromo-N-(5-fluoro-1H-indazol-3-yl)-6-(isopropylsulfonyl)quinolin-4-amine;
7-bromo-N-(5-fluoro-1H-indazol-3-yl)-6-((tetrahydro-2H-pyran-4-yl)sulfonyl)quinolin-4-amine;
N-1,3-benzothiazol-5-yl-6-[(1,1-dimethylethyl)sulfonyl]-7-(methyloxy)-4-quinolinamine;
6-(tert-butylsulfonyl)-4-((4,5-dimethyl-1H-pyrazol-3-yl)amino)quinolin-7-ol;
2-((6-(tert-butylsulfonyl)-4-((4,5-dimethyl-1H-pyrazol-3-yl)amino)quinolin-7-yl)oxy)ethanol;
6-(tert-butylsulfonyl)-7-(difluoromethoxy)-N-(4,5-dimethyl-1H-pyrazol-3-yl)quinolin-4-amine;
7-(difluoromethoxy)-N-(4,5-dimethyl-1H-pyrazol-3-yl)-6-((tetrahydro-2H-pyran-4-yl)sulfonyl)quinolin-4-amine;
2-((4-(benzo[d]thiazol-5-ylamino)-6-(tert-butylsulfonyl)quinolin-7-yl)oxy)ethanol;
(3-(6-(tert-butylsulfonyl)-7-methoxyquinolin-4-yl)amino)-4-methyl-1H-pyrazol-5-yl)methanol;
N-(4,5-dimethyl-1H-pyrazol-3-yl)-7-methyl-6-((4-methyltetrahydro-2H-pyran-4-yl)sulfonyl)quinolin-4-amine;
N-(5-fluoro-1H-indazol-3-yl)-7-methyl-6-((4-methyltetrahydro-2H-pyran-4-yl)sulfonyl)quinolin-4-amine;
N-(4,5-dimethyl-1H-pyrazol-3-yl)-7-ethyl-6-((4-methyltetrahydro-2H-pyran-4-yl)sulfonyl)quinolin-4-amine;
7-ethyl-N-(5-fluoro-1H-indazol-3-yl)-6-((4-methyltetrahydro-2H-pyran-4-yl)sulfonyl)quinolin-4-amine;
N-(7-chloro-1H-indazol-3-yl)-7-methyl-6-((4-methyltetrahydro-2H-pyran-4-yl)sulfonyl)quinolin-4-amine;
or a salt, particularly a pharmaceutically acceptable salt, thereof.

Selected compounds of this invention are:
6-(tert-butylsulfonyl)-N-(4,5-dimethyl-1H-pyrazol-3-yl)-7-methoxyquinolin-4-amine;
6-[(1,1-dimethylethyl)sulfinyl]-N-(4,5-dimethyl-1H-pyrazol-3-yl)-7-(methyloxy)-4-quinolinamine;
N-(4,5-dimethyl-1H-pyrazol-3-yl)-7-methoxy-6-((tetrahydro-2H-pyran-4-yl)sulfonyl)quinolin-4-amine;
2-((6-(tert-butylsulfonyl)-4-((4,5-dimethyl-1H-pyrazol-3-yl)amino)quinolin-7-yl)oxy)ethanol;
N-(4,5-dimethyl-1H-pyrazol-3-yl)-6-[(1-methylethyl)sulfonyl]-7-(methyloxy)-4-quinolinamine;
N-(4,5-dimethyl-1H-pyrazol-3-yl)-7-methyl-6-((tetrahydro-2H-pyran-4-yl)sulfonyl)quinolin-4-amine;
or a salt, particularly a pharmaceutically acceptable salt, thereof.

Particular compounds of this invention are:
6-(tert-butylsulfonyl)-N-(4,5-dimethyl-1H-pyrazol-3-yl)-7-methoxyquinolin-4-amine;
N-(4,5-dimethyl-1H-pyrazol-3-yl)-7-methoxy-6-((tetrahydro-2H-pyran-4-yl)sulfonyl)quinolin-4-amine;
N-(4,5-dimethyl-1H-pyrazol-3-yl)-6-[(1-methylethyl)sulfonyl]-7-(methyloxy)-4-quinolinamine;
N-(4,5-dimethyl-1H-pyrazol-3-yl)-7-methyl-6-((tetrahydro-2H-pyran-4-yl)sulfonyl)quinolin-4-amine; specifically, 6-(tert-butylsulfonyl)-N-(4,5-dimethyl-1H-pyrazol-3-yl)-7-methoxyquinolin-4-amine;
or a salt, particularly a pharmaceutically acceptable salt, thereof.

Representative compounds of this invention are provided in Examples 1-83.

Accordingly, a compound of the invention includes a compound of Formula (I), particularly, a compound of Formula (I), (II) or (III) and the specific compounds described herein, or a salt thereof, particularly a pharmaceutically acceptable salt thereof. In one embodiment, the invention is directed to a method of inhibiting RIP2 kinase comprising contacting a cell with a compound of the invention. In another embodiment, the invention is directed to a method of treating a RIP2 kinase-mediated disease or disorder comprising administering a therapeutically effective amount of a compound of the invention to a human in need thereof. The invention is still further directed to the use of a compound of the invention or a pharmaceutical composition comprising a compound of the invention to inhibit RIP2 kinase and/or treat a RIP2 kinase-mediated disease or disorder.

The compounds according to Formula (I) may contain one or more asymmetric center (also referred to as a chiral center) and may, therefore, exist as individual enantiomers, diastereomers, or other stereoisomeric forms, or as mixtures thereof. Chiral centers, such as a chiral carbon, or particularly, a chiral —SO— moiety, may also be present in the compounds of this invention. Where the stereochemistry of a chiral center present in a compound of this invention, or in any chemical structure illustrated herein, is not specified the structure is intended to encompass all individual stereoisomers and all mixtures thereof. For example, each of (R)-6-[(1,1-dimethylethyl)sulfinyl]-N-(4,5-dimethyl-1H-pyrazol-3-yl)-7-(methyloxy)-4-quinolinamine and (S)-6-[(1,1-dimethylethyl)sulfinyl]-N-(4,5-dimethyl-1H-pyrazol-3-yl)-7-(methyloxy)-4-quinolinamine are encompassed by 6-[(1,1-dimethylethyl)sulfinyl]-N-(4,5-dimethyl-1H-pyrazol-3-yl)-7-(methyloxy)-4-quinolinamine. Thus, compounds according to Formula (I) containing one or more chiral center may be used as racemic mixtures, enantiomerically enriched mixtures, or as enantiomerically pure individual stereoisomers.

Individual stereoisomers of a compound according to Formula (I) which contain one or more asymmetric center may be resolved by methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral environment, for example, on a chiral support such as silica with a bound chiral ligand or in the presence of a chiral solvent. The skilled artisan will appreciate that where the desired stereoisomer is converted into another chemical entity by one of the separation procedures described above, a further step is required to liberate the desired form. Alternatively, specific stereoisomers may be synthesized by asymmetric synthesis using optically active reagents, substrates, catalysts or solvents, or by converting one enantiomer to the other by asymmetric transformation.

It is to be understood that a solid form of a compound of the invention may exist in crystalline forms, non-crystalline forms or a mixture thereof. Such crystalline forms may also exhibit polymorphism (i.e. the capacity to occur in different crystalline forms). These different crystalline forms are typically known as "polymorphs." Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. One of ordinary skill in the art will appreciate that different polymorphs may be produced, for example, by changing or adjusting the conditions used in crystallizing/recrystallizing the compound.

Because of their potential use in medicine, the salts of the compounds of Formula (I) are preferably pharmaceutically acceptable salts. Suitable pharmaceutically acceptable salts include those described by Berge, Bighley and Monkhouse J. Pharm. Sci (1977) 66, pp 1-19. Salts encompassed within the term "pharmaceutically acceptable salts" refer to non-toxic salts of the compounds of this invention.

When a compound of the invention is a base (contains a basic moiety), a desired salt form may be prepared by any suitable method known in the art, including treatment of the free base with an inorganic acid, such as hydrochloric acid, hydrobromic acid, sulfuric acid, nitric acid, phosphoric acid, and the like, or with an organic acid, such as acetic acid, trifluoroacetic acid, maleic acid, succinic acid, mandelic acid, fumaric acid, malonic acid, pyruvic acid, oxalic acid, glycolic acid, salicylic acid, and the like, or with a pyranosidyl acid, such as glucuronic acid or galacturonic acid, or with an alpha-hydroxy acid, such as citric acid or tartaric acid, or with an amino acid, such as aspartic acid or glutamic acid, or with an aromatic acid, such as benzoic acid or cinnamic acid, or with a sulfonic acid, such as p-toluenesulfonic acid, methanesulfonic acid, ethanesulfonic acid or the like.

Suitable addition salts are formed from acids which form non-toxic salts and examples include acetate, p-aminobenzoate, ascorbate, aspartate, benzenesulfonate, benzoate, bicarbonate, bismethylenesalicylate, bisulfate, bitartrate, borate, calcium edetate, camsylate, carbonate, clavulanate, citrate, cyclohexylsulfamate, edetate, edisylate, estolate, esylate, ethanedisulfonate, ethanesulfonate, formate, fumarate, gluceptate, gluconate, glutamate, glycollate, glycollylarsanilate, hexylresorcinate, hydrabamine, hydrobromide, hydrochloride, dihydrochloride, hydrofumarate, hydrogen phosphate, hydroiodide, hydromaleate, hydrosuccinate, hydroxynaphthoate, isethionate, itaconate, lactate, lactobionate, laurate, malate, maleate, mandelate, mesylate, methylsulfate, monopotassium maleate, mucate, napsylate, nitrate, N-methylglucamine, oxalate, oxaloacetate, pamoate (embonate), palmate, palmitate, pantothenate, phosphate/diphosphate, pyruvate, polygalacturonate, propionate, saccharate, salicylate, stearate, subacetate, succinate, sulfate, tannate, tartrate, teoclate, tosylate, triethiodide, trifluoroacetate and valerate.

Other exemplary acid addition salts include pyrosulfate, sulfite, bisulfite, decanoate, caprylate, acrylate, isobutyrate, caproate, heptanoate, propiolate, oxalate, malonate, suberate, sebacate, butyne-1,4-dioate, hexyne-1,6-dioate, chlorobenzoate, methylbenzoate, dinitrobenzoate, hydroxybenzoate, methoxybenzoate, phthalate, phenylacetate, phenylpropionate, phenylbutrate, lactate, γ-hydroxybutyrate, mandelate, and sulfonates, such as xylenesulfonate, propanesulfonate, naphthalene-1-sulfonate and naphthalene-2-sulfonate.

If an inventive basic compound is isolated as a salt, the corresponding free base form of that compound may be prepared by any suitable method known to the art, including treatment of the salt with an inorganic or organic base, suitably an inorganic or organic base having a higher $pK_a$ than the free base form of the compound.

When a compound of the invention is an acid (contains an acidic moiety), a desired salt may be prepared by any suitable method known to the art, including treatment of the free acid with an inorganic or organic base, such as an amine (primary, secondary, or tertiary), an alkali metal or alkaline earth metal hydroxide, or the like. Illustrative examples of suitable salts include organic salts derived from amino acids such as glycine and arginine, ammonia, primary, secondary, and tertiary amines, and cyclic amines, such as N-methyl-D-glucamine, diethylamine, isopropylamine, trimethylamine, ethylene diamine, dicyclohexylamine, ethanolamine, piperidine, morpholine, and piperazine, as well as inorganic salts derived from sodium, calcium, potassium, magnesium, manganese, iron, copper, zinc, aluminum, and lithium.

Certain of the compounds of the invention may form salts with one or more equivalents of an acid (if the compound contains a basic moiety) or a base (if the compound contains an acidic moiety). The present invention includes within its scope all possible stoichiometric and non-stoichiometric salt forms.

Compounds of the invention having both a basic and acidic moiety may be in the form of zwitterions, acid-addition salt of the basic moiety or base salts of the acidic moiety.

This invention also provides for the conversion of one pharmaceutically acceptable salt of a compound of this invention, e.g., a hydrochloride salt, into another pharmaceutically acceptable salt of a compound of this invention, e.g., a sulfate salt.

For solvates of the compounds of Formula (I), including solvates of salts of the compounds of Formula (I), that are in crystalline form, the skilled artisan will appreciate that pharmaceutically acceptable solvates may be formed wherein solvent molecules are incorporated into the crystalline lattice during crystallization. Solvates may involve nonaqueous solvents such as ethanol, isopropanol, DMSO, acetic acid, ethanolamine, and EtOAc, or they may involve water as the solvent that is incorporated into the crystalline lattice. Solvates wherein water is the solvent that is incorporated into the crystalline lattice are typically referred to as "hydrates." Hydrates include stoichiometric hydrates as well as compositions containing variable amounts of water. The invention includes all such solvates, particularly hydrates. It is to be understood that the term "a salt, particularly a pharmaceutically acceptable salt, thereof, or hydrate thereof" encompasses a salt of a compound of Formula (I), a pharmaceutically acceptable salt of a compound of Formula (I), a hydrate of a compound of Formula (I), a hydrate of a salt of a compound of Formula (I), and a hydrate of a pharmaceutically acceptable salt of a compound of Formula (I).

Because the compounds of Formula (I) are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions.

General Synthetic Methods

The compounds of Formula (I) may be obtained by using synthetic procedures illustrated in the Schemes below or by drawing on the knowledge of a skilled organic chemist. The syntheses provided in these Schemes are applicable for producing compounds of the invention having a variety of different substituent groups employing appropriate precursors, which are suitably protected if needed, to achieve compatibility with the reactions outlined herein. Subsequent deprotection, where needed, affords compounds of the nature generally disclosed. While the Schemes are shown with compounds only of Formula (I), they are illustrative of processes that may be used to make the compounds of the invention.

Intermediates (compounds used in the preparation of the compounds of the invention) may also be present as salts. Thus, in reference to intermediates, the phrase "compound(s) of formula (number)" means a compound having that structural formula or a pharmaceutically acceptable salt thereof.

Scheme 1: 6-Bromo-4-chloro-7-methoxyquinolines may be synthesized via condensation of an aniline with Meldrum's acid followed by cyclization to the hydroxyquinoline. Conversion of the hydroxyquinoline tothe chloroquinoline may be achieved with POCl₃.

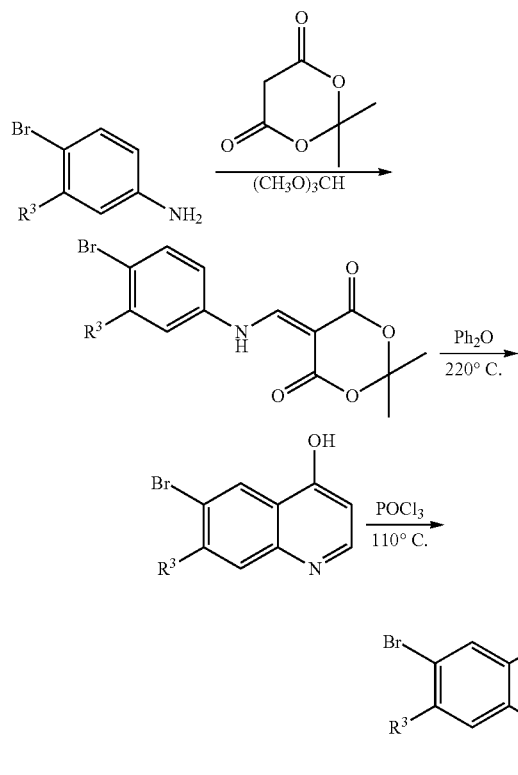

Scheme 2: 4-Methyltetrahydro-2H-pyran-4-thiol can be made by epoxide formation from dihydro-2H-pyran-4(3H)-one followed by conversion to the thiirane and subsequent reduction to the thiol.

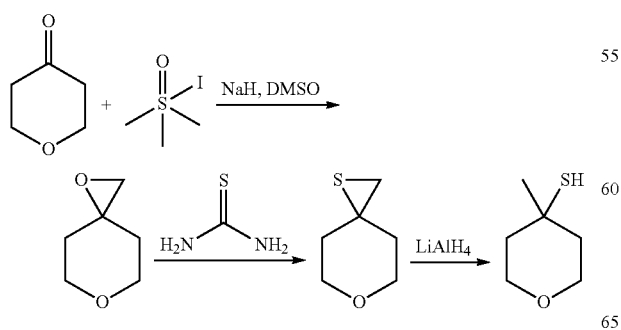

Scheme 3: The β-susbstituted tetrahydropyranylthiol may be synthesized from dihydro-2H-pyran-4(3H)-one. Alkylation at the β-position can be followed by reduction to the alcohol. Following a separation of the diastereomers, the cis isomer may be subjected to a mesylation and treatment with potassium thiolate. Removal of the acetate under reducing conditions provides the thiol.

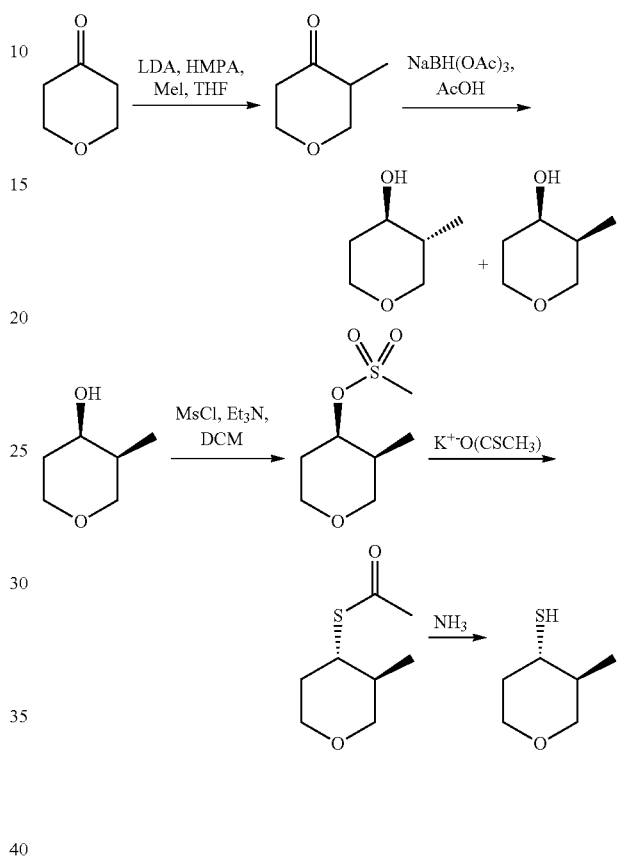

Scheme 4: Additional substituted tetrahydropyranylthiols may be synthesized from commercially available pyranones following a similar method to Scheme 3.

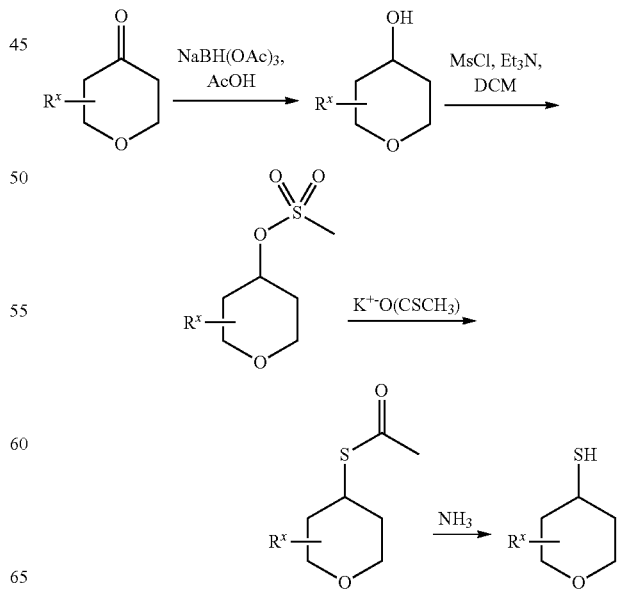

Scheme 5: Alkylation of ethyl dioxalate with proprionitrile followed by condensation with hydrazine can provide ethyl 3-amino-4-methyl-1H-pyrazole-5-carboxylate.

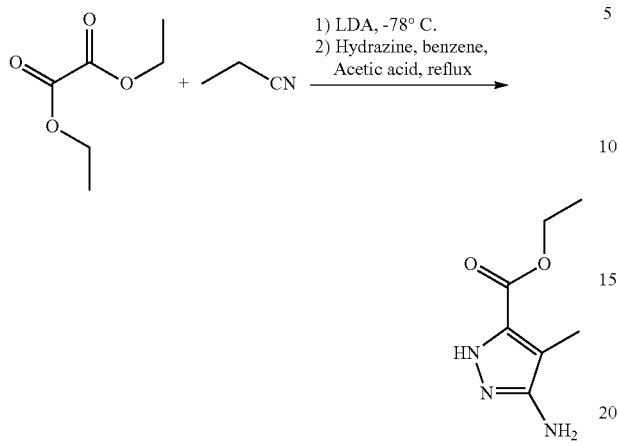

Scheme 6: The synthesis of 5-fluoro-1H-pyrazole[3,4-b]pyridin-3-amine may begin with amidation of 2-chloro-5-fluoro-3-pyridinecarboxylic acid. Reduction of the amide to the nitrile followed by reaction with hydrazone affords the azaindazole.

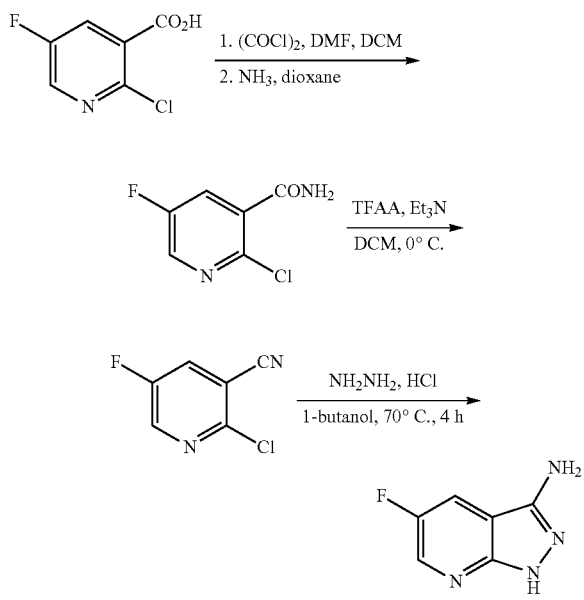

Scheme 7: Substituent "Z" groups can be attached to the quinoline core by treatment of the 4-chloroquinoine with the appropriate amine under microwave conditions or by heating in the presence of acid. The sulfide may then be installed under palladium catalyzed conditions. Treatment of the sulfide with Fe(III)Cl and one equivalent periodic acid or careful addition of oxone provides the sulfoxide. Further reaction with excess oxone provides the sulfone.

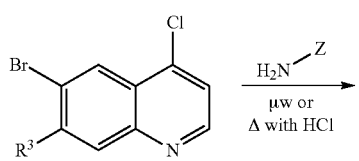

-continued

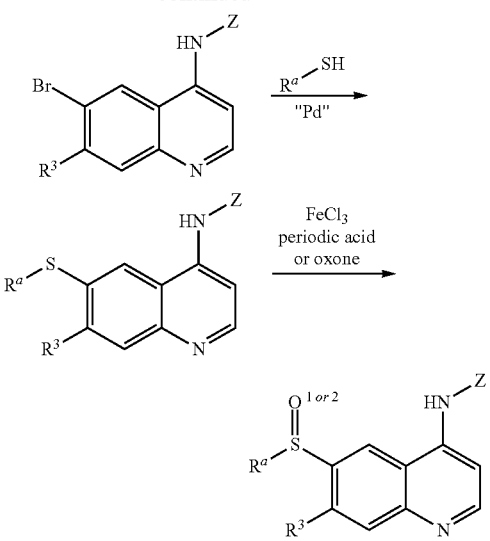

Scheme 8: Alternatively, the "Z" group can be installed following the palladium catalyzed formation of the sulfide and prior to the oxidation of the sulfide.

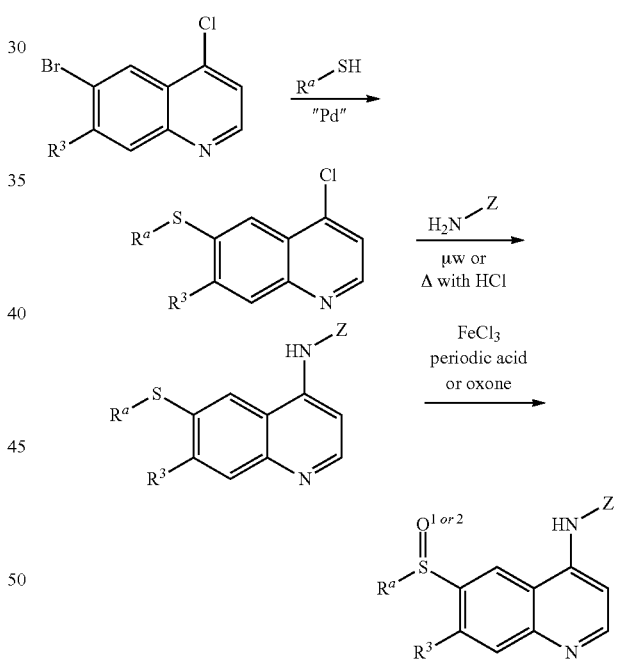

Scheme 9: In another method, the "Z" group may be installed as the last step following the palladium catalyzed formation of the sulfide and oxidation of the sulfide. However, oxidation after the installation of the "Z" group as in schemes 3 and 4 may lead to less N-oxide byproduct.

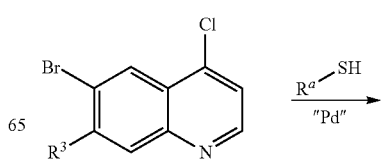

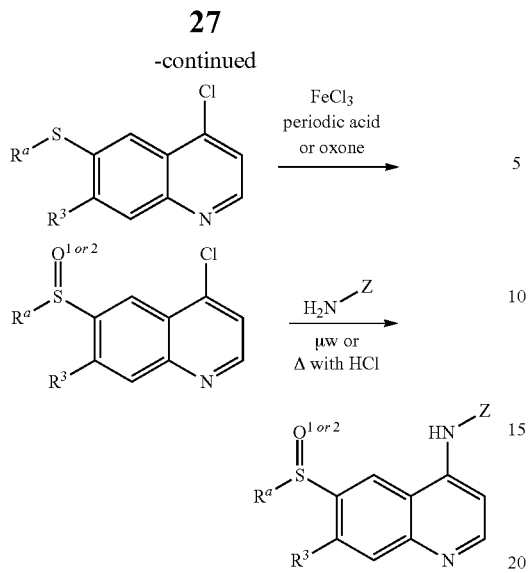

Scheme 10: 3-Bromo-4-sulfonlylanilines can be synthesized from 2-bromo-1-fluoro-4-nitrobenzene. Displacement of the aryl fluorine with a thiol followed by oxidation to the sulfone provides the sulfonylnitrobenzene. The nitrobenzene can be reduced to the aniline with Sn(II)Cl as in this scheme or with iron/acetic acid as in scheme 7.

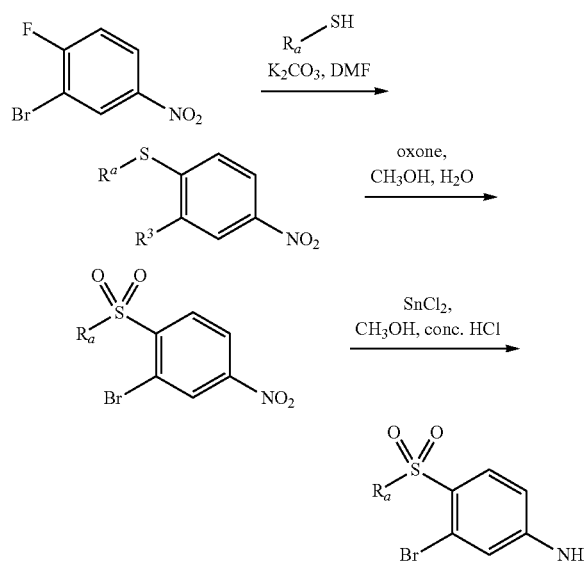

Scheme 11: 7-Bromoquinolines can be synthesized via the appropriate nitrobenzene. Reduction of the nitrobenzene to the aniline followed by reaction with Meldrum's acid affords the imine which can by cyclized to the hydroxyquinoline core. Functionalization to the chloride may occur via reaction with POCl₃. The "Z" group may then be installed as the last step.

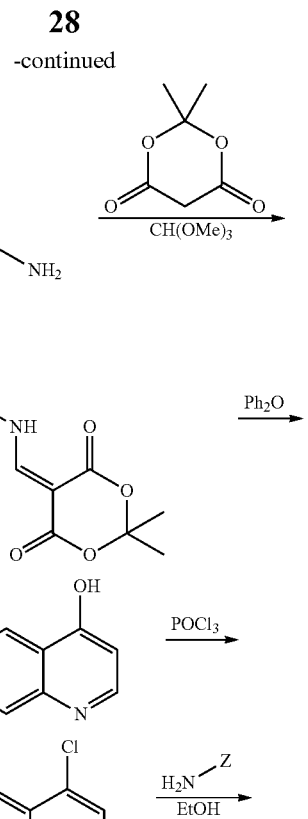

Scheme 12: 4,7-Dichloro-6-iodoquinolines may be synthesized via condensation of an aniline with diethyl[(ethyloxy)methylidene] propanediote followed by cyclization to the aryl ester. Following hydrolysis or the ester and decarboxylation, conversion of the hydroxyquinoline to the chloroquinoline may be achieved with POCl₃.

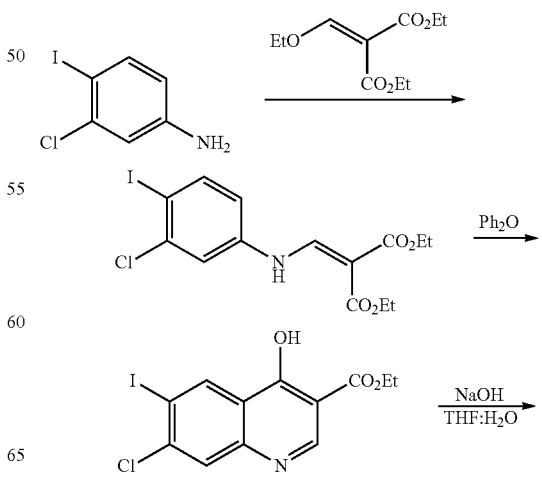

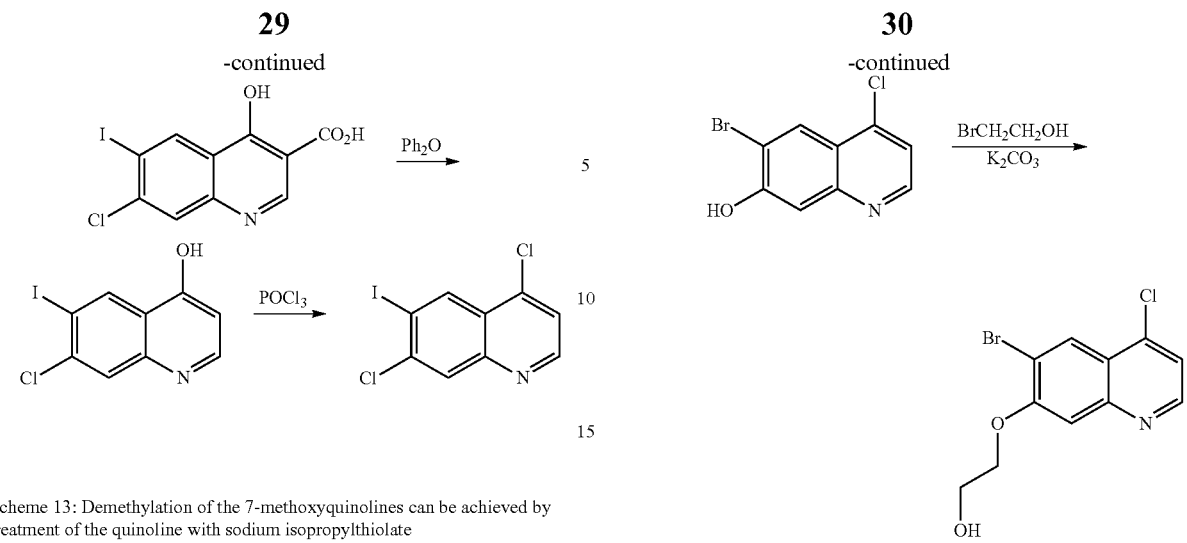

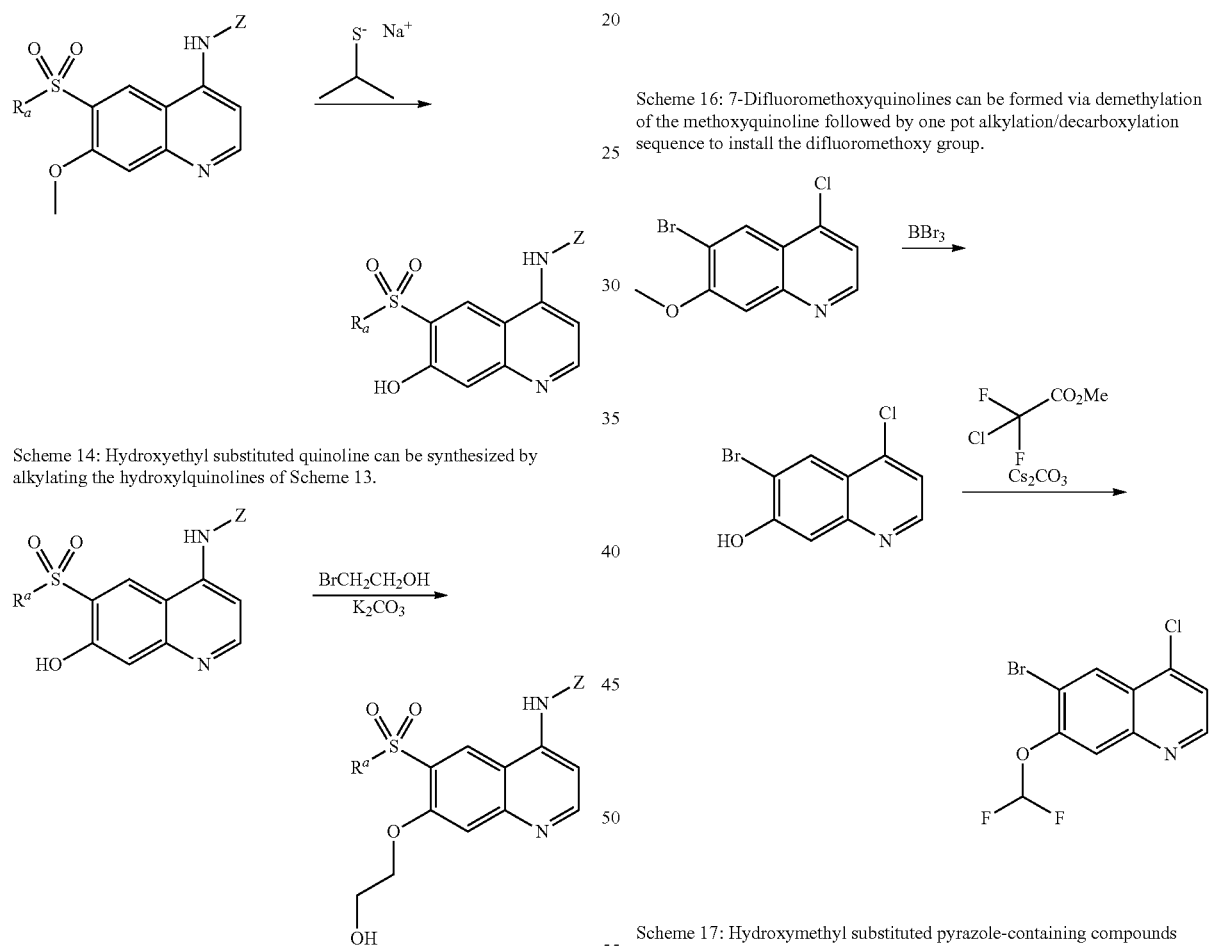

Scheme 13: Demethylation of the 7-methoxyquinolines can be achieved by treatment of the quinoline with sodium isopropylthiolate Scheme 14: Hydroxyethyl substituted quinoline can be synthesized by alkylating the hydroxylquinolines of Scheme 13.

Scheme 15: Alternatively, the alkylation to install the hydroxyethyl substituent can be done prior to installing the "Z" group or sulfone.

Scheme 16: 7-Difluoromethoxyquinolines can be formed via demethylation of the methoxyquinoline followed by one pot alkylation/decarboxylation sequence to install the difluoromethoxy group.

Scheme 17: Hydroxymethyl substituted pyrazole-containing compounds can be synthesized by first installing ethyl 3-amino-4-methyl-1H-pyrazole-5-carboxylate on the quinoline core followed by reduction to the alcohol.

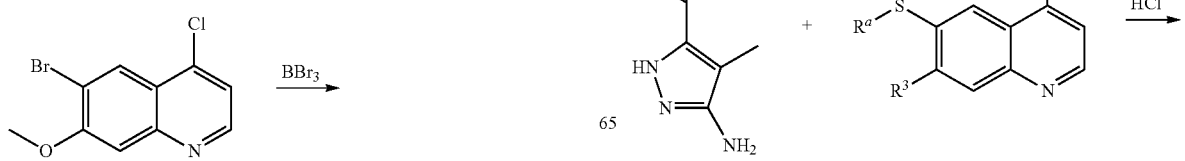

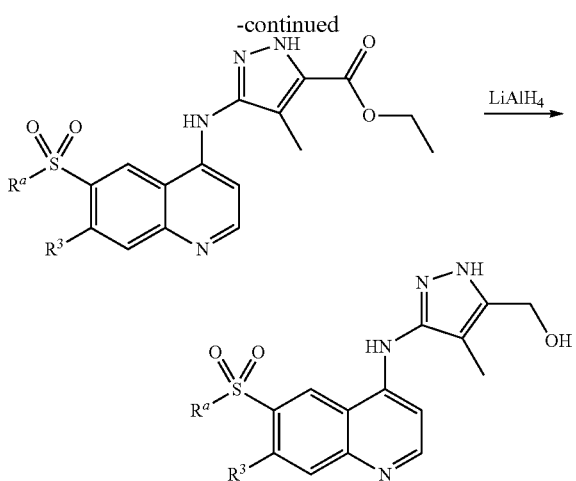

Scheme 18: Hydroxylated sulfones could undergo an internal cyclization to form cyclic sulfones upon demethylation of the 7-methoxy substituent.

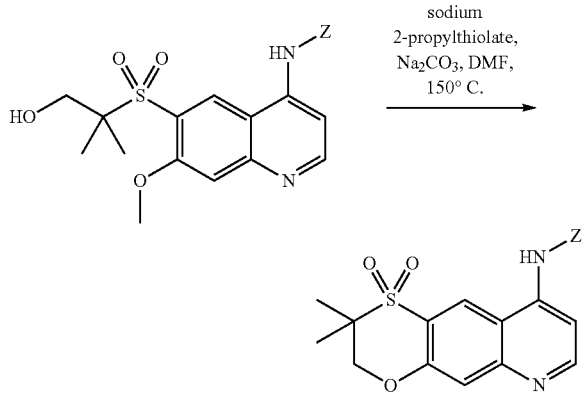

Scheme 19: 6-Tetrahydropyranylsulfonyl containing quinolines could be directly alkylated to install an α-methyl group specifically when the R³ group is an alkyl group (Me or Et).

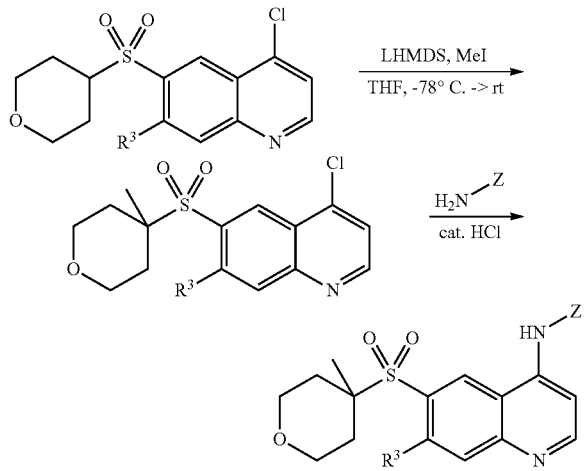

The compounds of this invention may be particularly useful for treatment of RIP2 kinase-mediated diseases or disorders, particularly, uveitis, interleukin-1 converting enzyme (ICE, also known as Caspase-1) associated fever syndrome, dermatitis, acute lung injury, type 2 diabetes mellitus, arthritis (specifically rheumatoid arthritis), inflammatory bowel disorders (such as ulcerative colitis and Crohn's disease), early-onset and extra-intestinal inflammatory bowel disease, prevention of ischemia reperfusion injury in solid organs (specifically kidney) in response ischemia induced by cardiac surgery, organ transplant, sepsis and other insults, liver diseases (non-alcohol steatohepatitis, alcohol steatohepatitis, and autoimmune hepatitis), allergic diseases (such as asthma), transplant reactions (such as graft versus host disease), autoimmune diseases (such as systemic lupus erythematosus, and multiple sclerosis), and granulomateous disorders (such as sarcoidosis, Blau syndrome, early-onset sarcoidosis, Wegner's granulomatosis, and interstitial pulmonary disease).

The compounds of this invention may be particularly useful in the treatment of uveitis, ICE fever, Blau Syndrome, early-onset sarcoidosis, ulcerative colitis, Crohn's disease, Wegener's granulamatosis and sarcoidosis.

Treatment of RIP2 kinase-mediated diseases or disorders, or more broadly, treatment of immune mediated diseases including, but not limited to, allergic diseases, autoimmune diseases, prevention of transplant rejection and the like, may be achieved using a compound of this invention as a monotherapy, or in dual or multiple combination therapy, particularly for the treatment of refractory cases, such as in combination with other anti-inflammatory and/or anti-TNF agents, which may be administered in therapeutically effective amounts as is known in the art.

For example, the compounds of this invention may be administered in combination with corticosteroids and/or anti-TNF agents to treat Blau syndrome, early-onset sarcoidosis; or in combination with anti-TNF biologics or other anti-inflammatory biologics to treat Crohn's Disease; or in combination with 5-ASA (mesalamine) or sulfasalazine to treat ulcerative colitis; or in combination with low-dose corticosteroids and/or methotrexate to treat Wegener's granulamatosis or sarcoidosis or interstitial pulmonary disease; or in combination with a biologic (e.g. anti-TNF, anti-IL-6, etc.) to treat rheumatoid arthritis; or in combination with anti-IL6 and/or methotrexate to treat ICE fever.

Examples of suitable anti-inflammatory agents include corticosteroids, particularly low-dose corticosteroids (such as Deltasone® (prednisone)) and anti-inflammatory biologics (such as Acterma® (anti-IL6R mAb) and Rituximab® (anti-CD20 mAb)). Examples of suitable anti-TNF agents include anti-TNF biologics (such as Enbrel® (etanecerpt)), Humira® (adalimumab), Remicade® (infliximab) and Simponi® (golimumab)).

This invention also provides a compound of Formula (I), or a salt thereof, particularly a pharmaceutically acceptable salt thereof, for use in therapy, specifically for use in the treatment of a RIP2 kinase-mediated disease or disorder, for example the diseases and disorders recited herein.

The invention also provides the use of a compound of Formula (I), or a salt thereof, particularly a pharmaceutically acceptable salt thereof, in the manufacture of a medicament for use in the treatment of a RIP2 kinase-mediated disease or disorder, for example the diseases and disorders recited herein.

A therapeutically "effective amount" is intended to mean that amount of a compound that, when administered to a patient in need of such treatment, is sufficient to effect treatment, as defined herein. Thus, e.g., a therapeutically effective amount of a compound of Formula (I), or a pharmaceutically acceptable salt thereof, is a quantity of an inventive agent that, when administered to a human in need thereof, is sufficient to modulate or inhibit the activity of RIP2 kinase such that a disease condition which is mediated by that activity is reduced, alleviated or prevented. The amount of a given compound that will correspond to such an amount will vary depending upon factors such as the particular compound (e.g., the potency ($pIC_{50}$), efficacy ($EC_{50}$), and the biological half-life of the particular compound), disease condition and its severity, the identity (e.g., age, size and weight) of the patient in need of treatment, but can nevertheless be routinely determined by one skilled in the art. Likewise, the duration of treatment and the time period of administration (time period between dosages and the timing of the dosages, e.g., before/with/after meals) of the compound will vary according to the identity of the mammal in need of treatment (e.g., weight), the particular compound and its properties (e.g., pharmaceutical characteristics), disease or disorder and its severity and the specific composition and method being used, but can nevertheless be determined by one of skill in the art.

"Treating" or "treatment" is intended to mean at least the mitigation of a disease condition in a patient. The methods of treatment for mitigation of a disease condition include the use of the compounds in this invention in any conventionally acceptable manner, for example for prevention, retardation, prophylaxis, therapy or cure of a mediated disease or disorder. Specific diseases and disorders that may be particularly susceptible to treatment using a compound of this invention are described herein.

The compounds of the invention may be administered by any suitable route of administration, including both systemic administration and topical administration. Systemic administration includes oral administration, parenteral administration, transdermal administration, rectal administration, and administration by inhalation. Parenteral administration refers to routes of administration other than enteral, transdermal, or by inhalation, and is typically by injection or infusion. Parenteral administration includes intravenous, intramuscular, and subcutaneous injection or infusion. Inhalation refers to administration into the patient's lungs whether inhaled through the mouth or through the nasal passages. Topical administration includes application to the skin.

The compounds of the invention may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound of the invention depend on the pharmacokinetic properties of that compound, such as absorption, distribution, and half-life, which can be determined by the skilled artisan. In addition, suitable dosing regimens, including the duration such regimens are administered, for a compound of the invention depend on the disease or disorder being treated, the severity of the disease or disorder being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change.

For use in therapy, the compounds of the invention will be normally, but not necessarily, formulated into a pharmaceutical composition prior to administration to a patient. Accordingly, the invention also is directed to pharmaceutical compositions comprising a compound of the invention and a pharmaceutically acceptable excipient.

The pharmaceutical compositions of the invention may be prepared and packaged in bulk form wherein an effective amount of a compound of the invention can be extracted and then given to the patient such as with powders, syrups, and solutions for injection. Alternatively, the pharmaceutical compositions of the invention may be prepared and packaged in unit dosage form. For oral application, for example, one or more tablets or capsules may be administered. A dose of the pharmaceutical composition contains at least a therapeutically effective amount of a compound of this invention (i.e., a compound of Formula (I), or a salt, particularly a pharmaceutically acceptable salt, thereof). When prepared in unit dosage form, the pharmaceutical compositions may contain from 1 mg to 1000 mg of a compound of this invention.

The pharmaceutical compositions of the invention typically contain one compound of the invention. However, in certain embodiments, the pharmaceutical compositions of the invention contain more than one compound of the invention. In addition, the pharmaceutical compositions of the invention may optionally further comprise one or more additional pharmaceutically active compounds.

As used herein, "pharmaceutically acceptable excipient" means a material, composition or vehicle involved in giving form or consistency to the composition. Each excipient must be compatible with the other ingredients of the pharmaceutical composition when commingled such that interactions which would substantially reduce the efficacy of the compound of the invention when administered to a patient and interactions which would result in pharmaceutical compositions that are not pharmaceutically acceptable are avoided. In addition, each excipient must of course be of sufficiently high purity to render it pharmaceutically acceptable.

The compounds of the invention and the pharmaceutically acceptable excipient or excipients will typically be formulated into a dosage form adapted for administration to the patient by the desired route of administration. Conventional dosage forms include those adapted for (1) oral administration such as tablets, capsules, caplets, pills, troches, powders, syrups, elixirs, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as aerosols and solutions; and (6) topical administration such as creams, ointments, lotions, solutions, pastes, sprays, foams, and gels.

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carrying or transporting the compound or compounds of the invention once administered to the patient from one organ, or portion of the body, to another organ, or portion of the body. Certain pharmaceutically acceptable excipients may be chosen for their ability to enhance patient compliance.

Suitable pharmaceutically acceptable excipients include the following types of excipients: diluents, fillers, binders, disintegrants, lubricants, glidants, granulating agents, coating agents, wetting agents, solvents, co-solvents, suspending agents, emulsifiers, sweeteners, flavoring agents, flavor masking agents, coloring agents, anti-caking agents, humectants, chelating agents, plasticizers, viscosity increasing agents, antioxidants, preservatives, stabilizers, surfactants, and buffering agents. The skilled artisan will appreciate that certain pharmaceutically acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically acceptable excipients in appropriate amounts for use in the invention. In addition, there are a number of resources that are available to the skilled artisan which describe pharmaceutically acceptable excipients and may be useful in selecting suitable pharmaceutically acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company).

In one aspect, the invention is directed to a solid oral dosage form such as a tablet or capsule comprising an effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesium stearate, calcium stearate, and talc.

EXAMPLES

The following examples illustrate the invention. These examples are not intended to limit the scope of the present invention, but rather to provide guidance to the skilled artisan to prepare and use the compounds, compositions, and methods of the present invention. While particular embodiments of the present invention are described, the skilled artisan will appreciate that various changes and modifications can be made without departing from the spirit and scope of the invention.

Names for the intermediate and final compounds described herein were generated using a software naming program. It will be appreciated by those skilled in the art that in certain instances this program will name a structurally depicted compound as a tautomer of that compound. It is to be understood that any reference to a named compound or a structurally depicted compound is intended to encompass all tautomers of such compounds and any mixtures of tautomers thereof.

In the following experimental descriptions, the following abbreviations may be used:

| Abbreviation | Meaning |
| --- | --- |
| AcOH | acetic acid |
| aq | aqueous |
| brine | saturated aqueous NaCl |
| $CH_2Cl_2$, DCM | methylene chloride |
| $CH_3CN$ or MeCN | acetonitrile |
| $CH_3NH_2$ | methylamine |
| d | day |
| DCE | 1,2-dichloroethane |
| DMA | dimethyl acetamide |
| DMF | N,N-dimethylformamide |
| DMSO | dimethylsulfoxide |
| EDC | 1-ethyl-3-(3-dimethylaminopropyl) carbodiimide |
| equiv | equivalents |
| Et | ethyl |
| $Et_3N$ | triethylamine |
| $Et_2O$ or DME | diethyl ether |
| EtOAc | ethyl acetate |
| EtOH | ethanol |
| h, hr | hour |
| HATU | O-(7-Azabenzotriazol-1yl)-N,N,N',N'-tetramethylyronium hexafluorophosphate |
| HCl | hydrochloric acid |
| HMPA | hexamethylphosphoramide |
| IPA | isopropyl alcohol |
| i-$Pr_2$NEt | N',N'-diisopropylethylamine |
| KOt-Bu | potassium tert-butoxide |
| LDA | lithium diisopropyl amide |
| LCMS | liquid chromatography-mass spectroscopy |
| LHDMS | lithium hexamethyldisilazane |
| Me | methyl |
| MeI | Methyl iodide |
| MeOH or $CH_3OH$ | methanol |
| $MgSO_4$ | magnesium sulfate |
| min | minute |
| MP-carbonate resin | polymer bound tetraalkylammonium carbonate |
| MS | mass spectrum |
| µw | microwave |
| $NaBH_4$ | sodium borohydride |
| $Na_2CO_3$ | sodium carbonate |
| $NaHCO_3$ | sodium bicarbonate |
| NaOH | sodium hydroxide |
| $Na_2SO_4$ | sodium sulfate |
| $NH_4Cl$ | ammonium chloride |
| $NiCl_2 \cdot 6H_2O$ | nickel (II) chloride hexahydrate |
| NMP | N-methyl-2-pyrrolidone |
| Ph | phenyl |
| RBF | round bottomed flask |
| rt | room temperature |
| satd or sat'd | saturated |
| SCX | strong cation exchange |
| SPE | solid phase extraction |
| TLC | Thin layer chromatography |
| TFA | trifluoroacetic acid |
| THF | tetrahydrofuran |
| $t_R$ | retention time |

Preparation 1

6-bromo-4-chloro-7-(methyloxy)quinoline

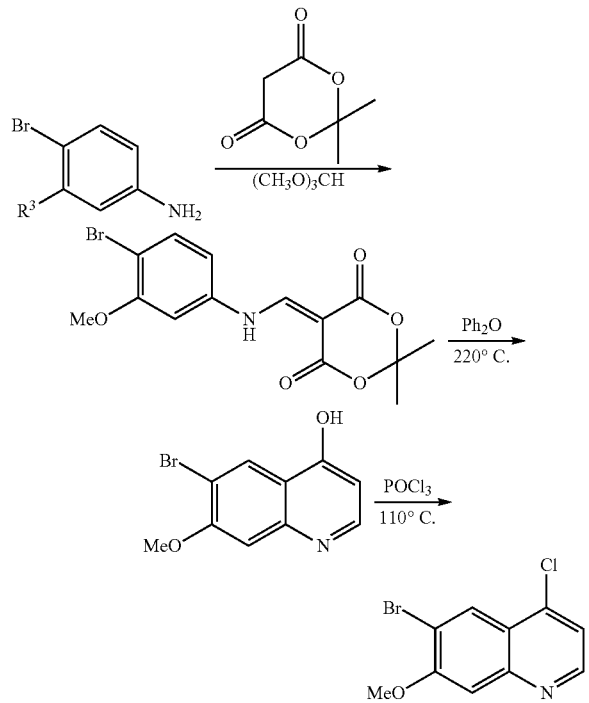

Step 1. 5-({[4-bromo-3-(methyloxy)phenyl]amino}methylidene)-2,2-dimethyl-1,3-dioxane-4,6-dione: 2,2-dimethyl-1,3-dioxane-4,6-dione (8.5 g, 58 mmol) in trimethyl orthoformate (50 mL, 450 mmol) was refluxed at 105° C. for 1 hr. 4-Bromo-3-methoxyaniline (10.5 g, 50.4 mmol) was then added and refluxing was continued for and additional hour. The suspension was filtered, and the solid was washed with MeOH and vacuum dried to yield 5-({[4-bromo-3-(methyloxy)phenyl]amino}methylidene)-2,2-dimethyl-1,3-dioxane-4,6-dione (17 g, 49 mmol, 96% yield). $^1$H NMR (400 MHz, DMSO-d) δ ppm 1.68 (s, 6H), 3.90 (s, 3H), 7.11 (dd, J=8.6 Hz, 2 Hz, 1H), 7.43 (d, J=2 Hz, 1H), 7.59 (d, J=8.6 Hz, 1H), 8.64 (s, 1H), 11.23 (br. s., 1H).

Step 2. 6-bromo-7-(methyloxy)-4-quinolinol: To diphenyl ether (68 mL, 420 mmol) at 230° C. was added 5-({[4-bromo-3-(methyloxy)phenyl]amino}methylidene)-2,2-dimethyl-1,3-dioxane-4,6-dione (15 g, 42 mmol), and the mixture was stirred for 1 hr. The reaction mixture was poured into hexane after being cooled to room temperature. The precipitate was filtered and washed with hexane. The brown solid was dried under vacuum overnight to afford 6-bromo-7-(methyloxy)-4-quinolinol (10 g, 33 mmol, 79% yield). $^1$H NMR (400 MHz, DMSO-d) δ ppm 3.94 (s, 3H), 5.99 (dd, J=7.4 Hz, 1.2 Hz, 1H), 7.05 (s, 1H), 7.86 (dd, J=7.4 Hz, 5.8 Hz, 1H), 8.16 (s, 1H), 11.68 (br. s., 1H). MS (m/z) 254, 256 (M+H$^+$).

Step 3. 6-bromo-4-chloro-7-(methyloxy)quinoline: 6-bromo-7-(methyloxy)-4-quinolinol (4.17 g, 16.41 mmol) in phosphorus oxychloride (7.73 mL, 82 mmol) was stirred at 110° C. for 1 hr. The reaction mixture was cooled and slowly poured into saturated sodium carbonate with ice while stirring. The resulting suspension was filtered, the solid was rinsed with water and vacuum-dried overnight to yield 6-bromo-4-chloro-7-(methyloxy)quinoline (4.6 g, 16 mmol, 97% yield). $^1$H NMR (400 MHz, DMSO-d) δ ppm 4.05 (s, 3H), 7.61 (s, 1H), 7.65 (d, J=4.8 Hz, 1H), 8.38 (s, 1H), 8.81 (d, J=4.8 Hz, 1H). MS (m/z) 272, 274 (M+H$^+$).

The following intermediates can be made in an analogous manner:

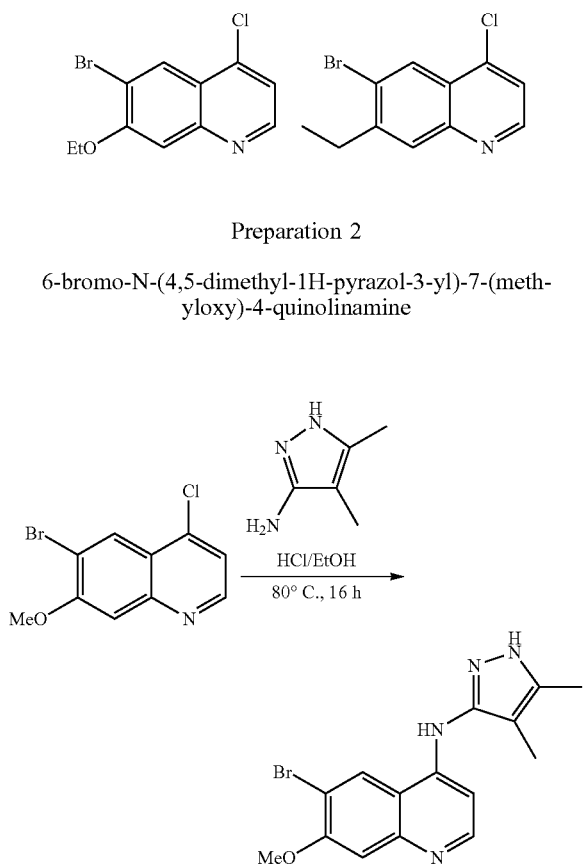

Preparation 2

6-bromo-N-(4,5-dimethyl-1H-pyrazol-3-yl)-7-(methyloxy)-4-quinolinamine

A mixture of 6-bromo-4-chloro-7-(methyloxy)quinoline (0.42 g, 1.5 mmol) and 4,5-dimethyl-1H-pyrazol-3-amine (0.17 g, 1.5 mmol) was heated in EtOH (3 mL) at 80° C. in a sealed tube for 16 h. The reaction mixture was cooled and Et$_2$O (10 mL) was added. Precipitate 6-bromo-N-(4,5-dimethyl-1H-pyrazol-3-yl)-7-(methyloxy)-4-quinolinamine was filtered and dried to give a brown solid. $^1$H NMR (DMSO-d$_6$) δ ppm 12.63 (br. s., 1H), 10.42 (br. s., 1H), 9.10 (s, 1H), 8.47 (d, J=7.1 Hz, 1H), 7.47 (s, 1H), 6.71 (d, J=6.8 Hz, 1H), 4.06 (s, 3H), 2.23 (s, 3H), 1.85 (s, 3H); MS (m/z) 347, 349 (M+H$^+$).

The following compounds were made in an analogous manner. Isopropanol may be used as the solvent in addition to ethanol.

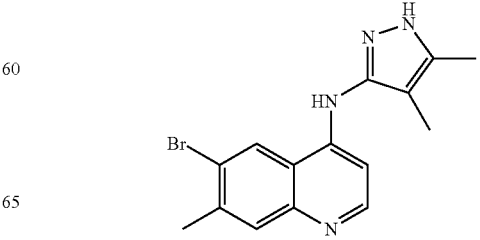

-continued

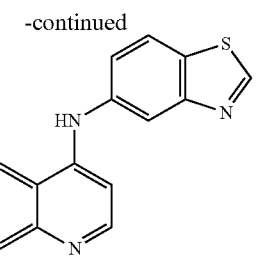

Preparation 3

4-methyltetrahydro-2H-pyran-4-thiol

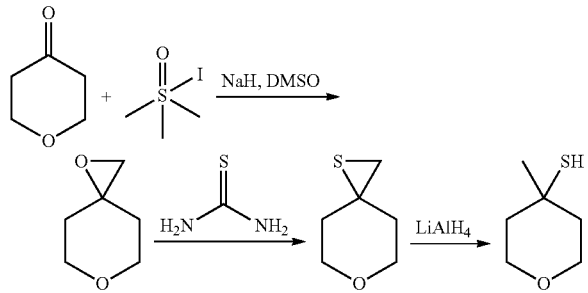

Step 1: 1,6-Dioxaspiro[2.5]octane: To a suspension of trimethylsulfoxonium iodide (28.6 g, 130 mmol) in DMSO (200 mL) in a two-neck RBF (500 mL) was added NaH (5.19 g, 130 mmol, 60% in mineral oil) in portions under $N_2$ atomsphere at room temperature. Stirring was continued for one hour, then a solution of dihydro-2H-pyran-4(3H)-one (10 g, 100 mmol) in DMSO (10 mL) was added dropwise over 5 min. The reaction mixture was stirred for 1 hr at room temperature, then poured into ice-water (300 mL) and extracted with $Et_2O$ (2×200 mL). The organic was washed with water and brine, dried over $MgSO_4$, filtered, and concentrated to give 1,6-dioxaspiro[2.5]octane (4.9 g, 42.9 mmol, 43.0% yield) as colorless oil. $^1$H NMR (400 MHz, Chloroform-d) δ: 1.52-1.59 (m, 2 H) 1.89 (ddd, J=13.20, 8.40, 4.67 Hz, 2 H) 2.71 (s, 2 H) 3.79-3.95 (m, 4 H).

Step 2: 6-Oxa-1-thiaspiro[2.5]octane: To a solution of 1,6-dioxaspiro[2.5]octane (200 mg, 1.752 mmol) in MeOH (5 mL) was added thiourea (133 mg, 1.75 mmol), and the reaction mixture was stirred and heated at 80° C. for 4 h. The precipitate that formed during the course of the reaction was filtered. The filtrate was diluted with $Et_2O$ (100 mL), washed with brine, dried over $MgSO_4$, filtered, and evaporated to give a colorless oil 6-oxa-1-thiaspiro[2.5]octane (216 mg, 1.659 mmol, 95% yield). $^1$H NMR (CHLOROFORM-d) δ: 3.97 (dt, J=11.3, 4.1 Hz, 2H), 3.76 (ddd, J=11.5, 9.2, 2.8 Hz, 2H), 2.49 (s, 2H), 2.22 (ddd, J=13.4, 9.5, 3.9 Hz, 2H), 1.55 (d, J=13.4 Hz, 2H).

Step 3: 4-Methyltetrahydro-2H-pyran-4-thiol: To a refluxing solution of 6-oxa-1-thiaspiro[2.5]octane (200 mg, 1.54 mmol) in THF (5 mL) was added $LiAlH_4$ in THF (0.40mL, 0.80 mmol) dropwise. The reaction was stirred for 1 hour, then cooled to 0° C. and quenched with water (1 mL). The mixture was stirred for 10 min and extracted with $Et_2O$ (2×10 mL). The organic was washed with brine, dried over $MgSO_4$, filtered, and concentrated. The residue was purified on silica gel column (10 g) and eluted with 10% EtOAc in hexane to give desired product (94 mg, 46%) as a colorless oil. $^1$H NMR (CHLOROFORM-d) δ: 3.78 (dd, J=6.8, 3.3 Hz, 4H), 1.73-1.84 (m, 2H), 1.64-1.73 (m, 3H), 1.51 (s, 3H).

Preparation 4

Trans-3-Methyltetrahydro-2H-pyran-4-thiol

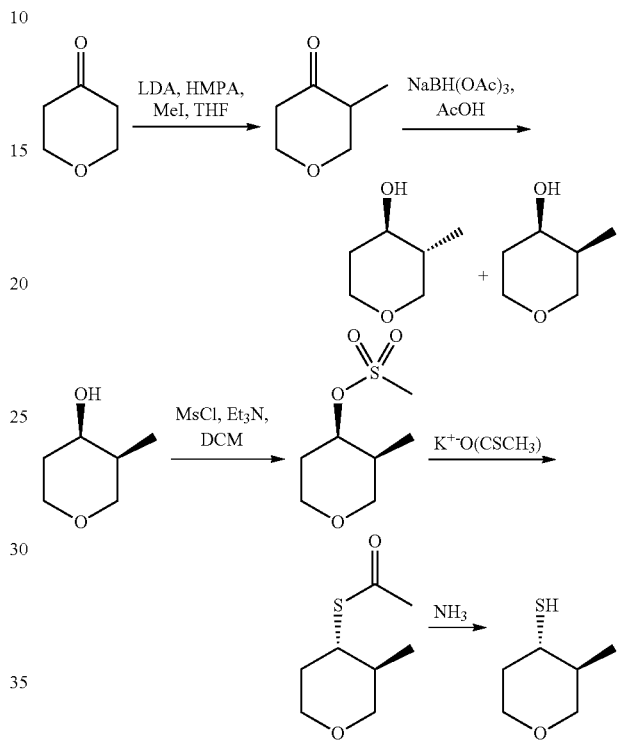

Step 1: 3-Methyltetrahydro-4H-pyran-4-one: To a solution of LDA (2.0 M in heptane/THF/ethylbenzene, 12.0 mL, 24.0 mmol) in THF (100 mL) cooled to −78° C. was added a solution of dihydro-2H-pyran-4(3H)-one (2 g, 20.0 mmol) and HMPA (3.5 mL, 20.0 mmol) in THF (70 mL) dropwise. After stirring for 5 min, MeI (6.25 mL, 100 mmol) in THF (30 mL) was added to the above solution, the reaction was warmed to 0° C. and kept for 2 h, then warmed to room temperature for 10 min, and then cooled again to 0° C. The reaction mixture was quenched with $NH_4Cl$ (sat'd) and extracted with $Et_2O$ (2×200 mL). The organic was washed with brine, dried over $MgSO_4$, filtered, and concentrated. The crude mixture was purified via a silica gel column (100 g), using 10-20% $Et_2O$ in DCM to give an orange oil 3-methyldihydro-2H-pyran-4(3H)-one (2.2 g, 19.30 mmol, 96% yield). $^1$H NMR (CHLOROFORM-d) δ: 4.12-4.32 (m, 2H), 3.67-3.81 (m, 2H), 2.60-2.74 (m, 1H), 2.54(dt, J=17.1, 6.1 Hz, 1H), 2.41 (dt, J=14.1, 2.7 Hz, 1H), 1.01 (d, J=6.8 Hz, 3H).

Step 2: Trans-3-methyltetrahydro-2H-pyran-4-ol: To a solution of 3-methyldihydro-2H-pyran-4(3H)-one (2.28 g, 20.0 mmol) in DCE (50 mL) was added sodium triacetoxyborohydride (8.47 g, 40.0 mmol), followed by acetic acid (3.4 mL, 59.9 mmol) and the reaction mixture was stirred at room temperature for 16 h. The reaction was quenched with water and extracted with $Et_2O$ (3×20 mL). Organic extracts were combined, washed with sodium bicarbonate (sat'd) and brine, dried over $MgSO_4$, filtered, and concentrated. The reaction mixture was purified on a silica gel column (100 g) using 50-60% EtOAc in hexane to give two products (the structures were confirmed by nOe experiments):

trans-3-methyltetrahydro-2H-pyran-4-ol (206 mg, 9% yield). ¹H NMR (400 MHz, CHLOROFORM-d) δ: 0.97 (d, J=13.39 Hz, 3 H) 1.63-1.87 (m, 3 H) 3.10 (d, J=11.37 Hz, 1 H) 3.43-3.58 (m, 3 H) 3.90-3.99 (m, 1 H).

cis-3-methyltetrahydro-2H-pyran-4-ol (790 mg, 34% yield). ¹H NMR (400 MHz, CHLOROFORM-d) δ: 0.96 (d, J=6.57 Hz, 3 H) 1.58-1.66 (m, 1 H) 1.92 (m, J=12.66, 4.64, 2.46, 2.46 Hz, 2 H) 2.96-3.07 (m, 1 H) 3.35 (td, J=9.85, 4.55 Hz, 1 H) 3.44 (td, J=11.87, 2.27 Hz, 1 H) 3.86 (dd, J=12.25, 3.66 Hz, 1 H) 3.97-4.03 (m, 1 H).

Step 3: cis-3-methyltetrahydro-2H-pyran-4-yl methanesulfonate: To a solution of cis-3-methyltetrahydro-2H-pyran-4-ol (780 mg, 6.71 mmol) in DCM (20 mL) was added methanesulfonyl chloride (0.63 mL, 8.06 mmol) followed by trimethylamine (1.87 mL, 13.43 mmol) at 0° C. The reaction mixture was stirred at 0° C. for 3 h, then quenched with water and extracted with DCM (2×30 mL). The organic was washed with sodium bicarbonate (sat'd) and brine, dried over MgSO₄, filtered, and concentrated to give a colorless oil cis-3-methyltetrahydro-2H-pyran-4-yl methanesulfonate (1.4 g, 7.21 mmol, 107% yield) which was used for next step without purification.

Step 4: trans-S-3-methyltetrahydro-2H-pyran-4-yl)ethanethioate: Potassium thioacetate (882 mg, 7.72 mmol) was added to a solution of cis-3-methyltetrahydro-2H-pyran-4-yl methanesulfonate (500 mg, 2.57 mmol) in DMA (8 mL) and the reaction was heated at 80° C. for 24 h. The reaction was cooled to room temperature and extracted with Et₂O (3×30 mL). Extracts were combined and washed with water (2×20 mL) and brine, dried over MgSO₄, filtered, and concentrated to give a red oil (single spot on TLC) as desired product trans-S-3-methyltetrahydro-2H-pyran-4-yl)ethanethioate (445 mg, 2.55 mmol, 99% yield) which was used for next step without purification.

Step 5: trans-3-methyltetrahydro-2H-pyran-4-thiol: Ammonia (2.0 M in MeOH, 10.400 mL, 20.80 mmol) was added to trans-S-3-methyltetrahydro-2H-pyran-4-yl) ethanethioate (440 mg, 2.52 mmol) and the reaction mixture was heated at 40° C. for 12 h. Upon completion, the mixture was concentrated in vacuo to give an orange solid. The solid was purified on an ISCO silica gel column (25 g), using 10-20% EtOAc in hexane to give desired product trans-3-methyltetrahydro-2H-pyran-4-thiol (71 mg, 0.54 mmol, 21.27% yield). ¹HNMR (400 MHz, CHLOROFORM-d) δ: 1.02-1.08 (m, 3 H) 1.76-1.95 (m, 2 H) 2.05-2.15 (m, 1 H) 3.13 (m, J=9.00, 4.28, 4.28, 2.40 Hz, 1 H) 3.42-3.58 (m, 2 H) 3.64 (dt, J=11.49, 4.48 Hz, 1 H) 3.88-3.96 (m, 1 H).

Preparation 5

(2R,6S)-2,6-Dimethyltetrahydro-2H-pyran-4-thiol

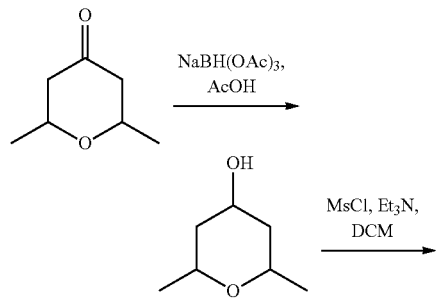

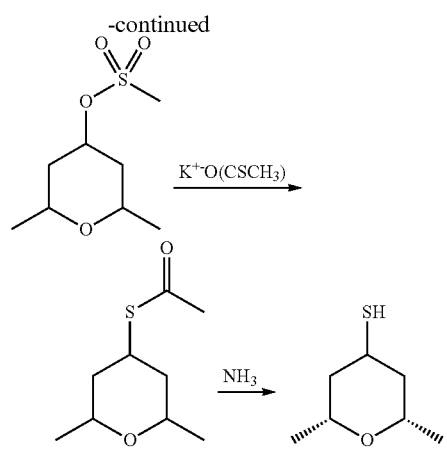

Step 1: 2,6-Dimethyltetrahydro-2H-pyran-4-ol: To a solution of 2,6-dimethyldihydro-2H-pyran-4(3H)-one (3 g, 23.41 mmol) in DCE (60 mL) was added sodium triacetoxyborohydride (14.88 g, 70.2 mmol) followed by acetic acid (8.1 mL, 140 mmol), and the reaction mixture was stirred at room temperature for 20 h. The reaction was quenched with water and extracted with Et₂O (3×50 mL). The organic was washed with brine, dried over MgSO₄, filtered, and concentrated to give the desired product 2,6-dimethyltetrahydro-2H-pyran-4-ol as a colorless oil (3 g, 23.04 mmol, 98% yield). ¹H NMR(CHLOROFORM-d) δ: 1.19-1.26 (m, 6 H) 1.83 (d, J=12.13 Hz, 2 H) 1.93 (dd, J=12.00, 4.67 Hz, 2 H) 3.58-3.68 (m, 1 H) 3.75-3.85 (m, 1 H) 3.93 (m, 1 H).

Step 2: 2,6-Dimethyltetrahydro-2H-pyran-4-yl methanesulfonate: To a solution of 2,6-dimethyltetrahydro-2H-pyran-4-ol (3 g, 23.04 mmol) in DCM (100 mL) was added mesyl chloride (2.16 mL, 27.7 mmol) and followed by Et₃N (6.42 mL, 46.1 mmol). The reaction mixture was stirred at 0° C. for 1 hr and quenched with water. The reaction mixture was extracted with DCM (2×50 mL), and the organic was washed with sodium bicarbonate (sat'd) and brine, dried over MgSO₄, filtered, concentrated. The crude mixture was purified on an ISCO silica column (40 g) using 50% EtOAc in hexane to give a white solid 2,6-dimethyltetrahydro-2H-pyran-4-yl methanesulfonate (2.17 g, 10.42 mmol, 45.2% yield).).

¹H NMR(CHLOROFORM-d) δ: 1.26 (d, J=6.06 Hz, 6 H) 1.40-1.51 (m, 2 H) 2.12 (dd, J=12.13, 4.80 Hz, 3 H) 3.03 (s, 3 H) 3.42-3.59 (m, 2 H) 4.82 (s, 1 H).

Step 3: S-(2,6-dimethyltetrahydro-2H-pyran-4-yl)ethanethioate: To a solution of 2,6-dimethyltetrahydro-2H-pyran-4-yl methanesulfonate (2.17 g, 10.42 mmol) in DMA (25 mL) was added potassium thioacetate (2.380 g, 20.84 mmol) and the reaction mixture was stirred at 65° C. for 20 h. The reaction mixture was cooled to room temperature, diluted with Et₂O (100 mL), and the organic was washed with water (2×20 mL) and brine, dried over MgSO₄, filtered, and concentrated. The crude mixture was purified on silica gel (50 g) using 10-20% EtOAc in hexane to give the desired product S-(2,6-dimethyltetrahydro-2H-pyran-4-yl)ethanethioate (1.93 g, 10.25 mmol, 98% yield). ¹H NMR (CHLOROFORM-d) δ: 4.03-4.09 (m, 1H), 3.65 (dd, J=6.6, 2.3 Hz, 2H), 2.34 (s, 3H), 1.65-1.71 (m, 4H), 1.18 (d, J=6.3 Hz, 6H); MS (m/z) 189 (M+H⁺).

Step 4: (2R,6S)-2,6-dimethyltetrahydro-2H-pyran-4-thiol: Ammonia (2.0M in MeOH, 6.37 mL, 12.75 mmol) was added to S-(2,6-dimethyltetrahydro-2H-pyran-4-yl) ethanethioate (500 mg, 2.66 mmol) and the reaction mixture was stirred at 23° C. for 20 h. The reaction was going slowly and was heated at 40° C. for an additional 4 h followed by concentration in vacuo and purification on an ISCO (silica gel column 25 g) using 0-10% EtOAc in hexane to give (2R,6S)-2,6-dimethyltetrahydro-2H-pyran-4-thiol (308 mg, 79% yield). The structure was confirmed by nOe experiment. ¹H NMR (400 MHz, CHLOROFORM-d) δ: 1.20 (d, J=6.32 Hz, 6 H) 1.58-1.77 (m, 5 H) 3.56-3.68 (m, 1 H) 3.88-4.04 (m, 2 H).

The following intermediate was synthesized in an analogous manner using p-toluenesulfonyl chloride in step 2 rather than methanesulfonyl chloride.

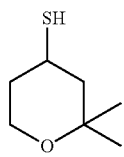

Preparation 6

N-(4,5-dimethyl-1H-pyrazol-3-yl)-7-(methyloxy)-6-(tetrahydro-2H-pyran-4-ylthio)-4-quinolinamine

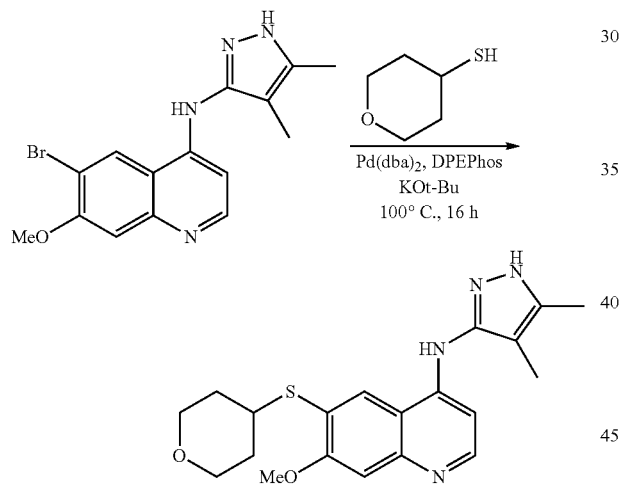

Method A: A mixture of 6-bromo-N-(4,5-dimethyl-1H-pyrazol-3-yl)-7-(methyloxy)-4-quinolinamine (250 mg, 0.60 mmol), tetrahydro-2H-pyran-4-thiol (70 mg, 0.60 mmol), potassium tert-butoxide (200 mg, 1.8 mmol), (oxydi-2,1-phenylene)bis-(diphenylphosphine) (32 mg, 0.060 mmol) and bis(dibenzylidineacetone)palladium (55 mg, 0.06 mmol) in 3.9 mL of DMF were heated at 100° C. in a sealed, nitrogen-purged vial for 16 h. The reaction was diluted with EtOAc and water and the layers were separated. The organics were concentrated, and the crude product was purified by column chromatography (Isco CombiFlash, 0% to 10% 2N NH₃/MeOH in DCM) to give N-(4,5-dimethyl-1H-pyrazol-3-yl)-7-(methyloxy)-6-(tetrahydro-2H-pyran-4-ylthio)-4-quinolinamine (80 mg, 35%). MS (m/z) 385 (M+H⁺). 1,4-Dioxane may also be used as the solvent. In cases where the starting quinoline is an HCl salt, and equivalent of triethylamine may also be added.

Method B: Alternatively, coupling reactions may be performed as follows: To a solution of quinoline (1 eq) in dioxane (0.1 M) was added (oxydibenzene-2,1-diyl)bis(diphenylphosphane) (0.1 eq), tris(dibenzylideneacetone)dipalladium(0) (0.1 eq), potassium tert-butoxide (1-2 eq), thiol (1.2 eq), and triethylamine (1-3 eq). The flask was purged with nitrogen, and heated under nitrogen for 3 h at 90° C. before pouring into EtOAc. The organic layer was washed with saturated sodium bicarbonate. The aqueous layer was washed with 25% EtOH in methylene chloride, then methylene chloride. The organics were combined, dried over MgSO₄ and concentrated to a brown oil. The residue was purified via Isco CombiFlash.

The following analogs were made in an analogous manner:

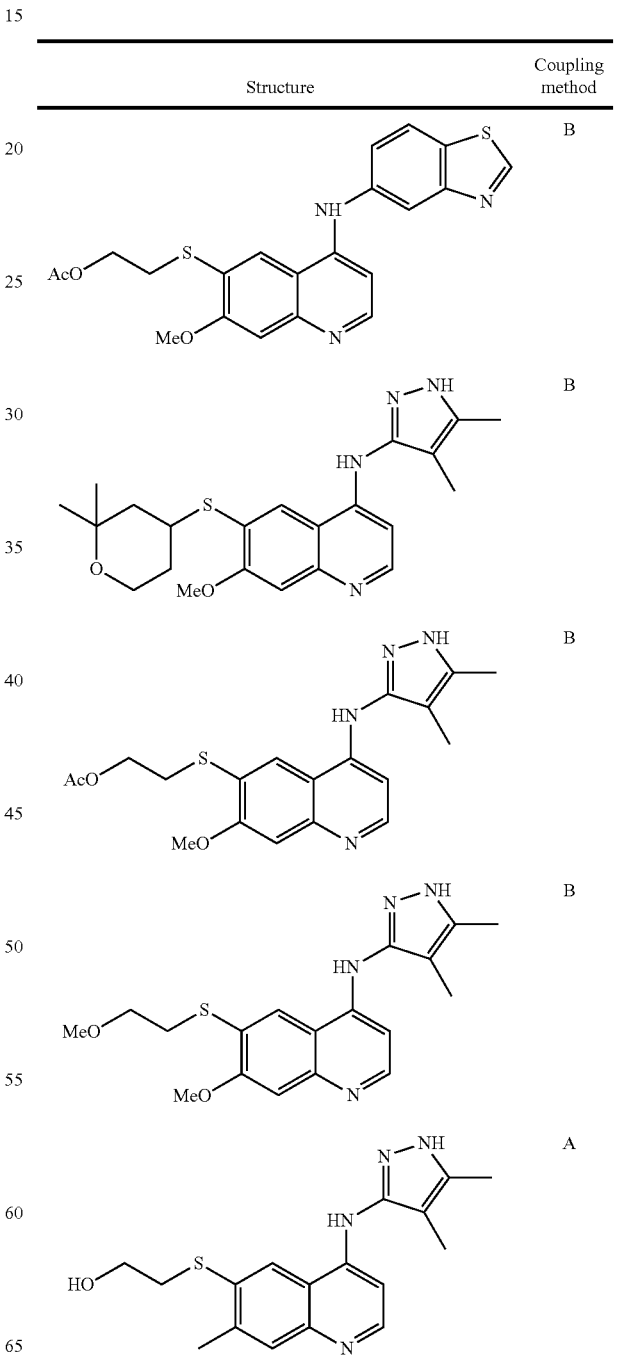

-continued

| Structure | Coupling method |
|---|---|
| (structure with methyl-tetrahydropyran-S-quinoline-pyrazole, MeO) | B |
| (structure with methyl-tetrahydropyran-S-quinoline-pyrazole, MeO) | B |
| (structure with dimethyl-tetrahydropyran-S-quinoline-pyrazole, MeO) | B |

Preparation 7

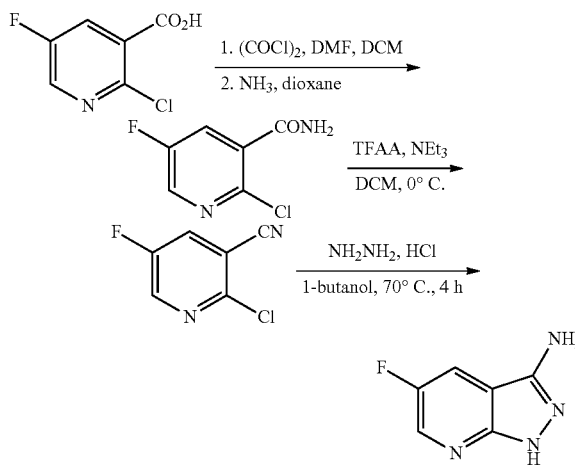

Step 1. 2-chloro-5-fluoro-3-pyridinecarboxamide: 2-Chloro-5-fluoro-3-pyridinecarboxylic acid (20 g, 110 mmol) was dissolved in DCM (400 mL), and then DMF (88 ul, 1.1 mmol) was added at 0° C. After the DMF addition, oxalyl chloride (26 mL, 300 mmol) was added dropwise at 0° C. The reaction mixture was stirred at room temperature for 16 hours, and concentrated in vacuo. The resulting yellow liquid was dissolved in 1,4-dioxane (400 mL), cooled to 0° C. and NH₃ (gas) (19.4 g, 1140 mmol) was bubbled through the solution for 30 minutes. The mixture was stirred at room temperature for 16 hours. The resulting white mixture was filtered and the filtrate was concentrated to give the desired product as a white solid (18 g, 89% yield). MS (m/z) 175 (M+H⁺); $^1$H NMR (400 MHz, DMSO-d$_6$) δ ppm 8.53 (d, 1 H), 8.10 (s, 1 H), 8.00 (dd, 1 H), 7.88 (s, 1 H).

Step 2. 2-chloro-5-fluoro-3-pyridinecarbonitrile: 2-Chloro-5-fluoro-3-pyridinecarboxamide (18 g, 102 mmol) was suspended in DCM (500 mL), and then triethylamine (31 mL, 220 mmol) was added at 0° C. Trifluoroacetic anhydride (TFAA) (16 mL, 110 mmol) was added dropwise to the reaction mixture at 0° C. The white carboxamide starting material disappeared after 20 minutes at 0° C., indicating the completion of the reaction. The reaction mixture was stirred at 0° C. for 1 hour. The reaction mixture was diluted with DCM, and then washed with saturated NaHCO₃(aq). The organic layer was washed with brine, dried over MgSO₄, filtered and the filtrate was concentrated to a brown residue. The residue was purified by Isco Combiflash (8%-20% EtOAc/Hexane; 330 g column). Collected fractions were combined and concentrated to give the desired product as a white solid (15 g, 96% yield). MS (m/z) 157 (M+H⁺). $^1$H NMR (400 MHz, DMSO-d$_6$) δ ppm 8.68 (dd, 1 H), 8.83 (d, 1 H).

Step 3. 5-fluoro-1H-pyrazolo[3,4-b]pyridin-3-amine: 2-Chloro-5-fluoro-3-pyridinecarbonitrile (15.3 g, 98 mmol) was dissolved in 1-butanol (300 mL), and then hydrazine monohydrate (16.82 mL, 293 mmol) was added, followed by hydrochloric acid (4N in dioxane) (0.244 mL, 0.977 mmol). The reaction mixture was maintained at 70° C. for 4 hours, and the resulting yellow crystalline solid was collected by filtration (12.5 g, 84% yield). MS (m/z) 153 (M+H⁺). $^1$H NMR (400 MHz, DMSO-d$_6$) δ ppm 5.56 (s, 2 H), 7.97 (dd, 1 H), 8.39 (m, 1 H), 12.07 (s, 1 H).

Preparation 8

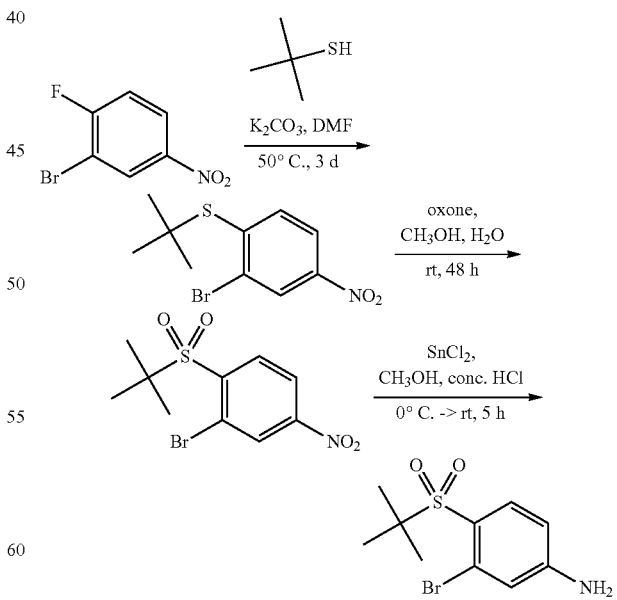

Step 1: 2-bromo-1-[(1,1-dimethylethyl)thio]-4-nitrobenzene: To a round bottom flask containing 2-bromo-1-fluoro-4-nitrobenzene (15 g, 68 mmol) and 2-methyl-2-propanethiol (8.4 mL, 75 mmol) in DMF (45 mL) was added potassium carbonate (10.37 g, 75 mmol). The reaction was heated to 50° C. for 3 d and partitioned between EtOAc and water. The aqueous layer was extracted with EtOAc (2×) and the combined organics were washed with water (3×) and brine (1×) and concentrated to dryness to afford 2-bromo-1-[(1,1-dimethylethyl)thio]-4-nitrobenzene (19 g, 66 mmol, 98% yield). $^1$H NMR (400 MHz, DMSO-$d_6$) δ ppm 8.47 (d, J=2.3 Hz, 1 H), 8.20 (dd, J=8.6, 2.5 Hz, 1 H), 7.93 (d, J=8.6 Hz, 1 H), 1.44 (s, 9 H)

Step 2: 2-bromo-4-nitrophenyl 1,1-dimethylethyl sulfone: To a round bottom flask containing 2-bromo-4-nitrophenyl 1,1-dimethylethyl sulfide (15 g, 53 mmol) in MeOH (89mL) and water (89 mL) was added oxone (49 g, 80 mmol). The reaction was stirred at rt for 18 h. An additional amount of oxone (25 g), MeOH (30 mL) and water (30 mL) were added at that time. After 24 h, additional oxone (25 g) was added and the reaction was stirred at rt for 24 h. The reaction was neutralized with 1N NaOH and DCM was added. The aqueous layer was extracted with DCM (1×) and the combined organic extracts were washed with brine (1×), dried over magnesium sulfate and purified via column chromatography in 2 batches (ISCO-Rf, 120 g, 0-30% EtOAc/hexane) to provide 2-bromo-4-nitrophenyl 1,1-dimethylethyl sulfone (9.6 g, 30 mmol, 56% yield. $^1$H NMR (400 MHz, DMSO-$d_6$) δ ppm 8.61 (d, J=2.3 Hz, 1 H), 8.43 (dd, J=8.6, 2.3 Hz, 1 H), 8.27 (d, J=8.8 Hz, 1 H), 1.35 (s, 9 H)

Step 3: 3-bromo-4-(tert-butylsulfonyl)aniline: A solution of tin (II) chloride dihydrate (17 g, 73 mmol) and conc HCl (24 mL) in MeOH (49 mL) was cooled to 0° C. and 2-bromo-1-(tert-butylsulfonyl)-4-nitrobenzene (4.7 g, 15 mmol) was added in one portion. After 5 h, the reaction was cooled to 0° C. and carefully neutralized with 6N NaOH (~75 mL). Ethyl acetate (350 mL) was added and the mixture was filtered in portions (white precipitate clogs the filter paper). The layers of the filtrate were separated and the aqueous layer was extracted with EtOAc (2×). The combined organic extracts were dried over magnesium sulfate and concentrated to dryness to provide 3-bromo-4-(tert-butylsulfonyl)aniline (3.8 g, 13 mmol, 90% yield). MS (m/z) 236, 238 (M-tbutyl+H$^+$). $^1$H NMR (400 MHz, DMSO-$d_6$) δ ppm 7.57 (d, J=8.8 Hz, 1 H), 6.93 (d, J=2.3 Hz, 1 H), 6.64 (dd, J=8.8, 2.3 Hz, 1 H), 6.41 (s, 2 H), 1.25 (s, 9 H)

The following intermediate was synthesized by an analogous method:

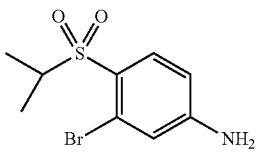

Preparation 9

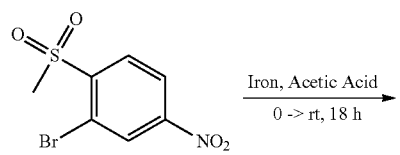

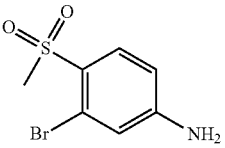

3-bromo-4-(methylsulfonyl)aniline: To a suspension of 2-bromo-1-(methylsulfonyl)-4-nitrobenzene (18.6 g, 66.4 mmol) in acetic acid (221 mL) was added iron (11.13 g, 199 mmol) portionwise at 0° C. The reaction was slowly warmed to room temperature overnight and then slowly poured into water (150 mL), EtOAc (600 mL), and 2N NaOH (450 mL) with stirring. Solid sodium carbonate (~300 g) was slowly added to the brown solution until bubbling ceased and the solution reached pH~10. The solution was transferred to a reparatory funnel, the layers were separated and the aqueous layer was extracted with EtOAc (1×). The combined organic extracts were concentrated to dryness to yield 3-bromo-4-(methylsulfonyl)aniline (10.5 g, 42.0 mmol, 63.2% yield). $^1$H NMR (400 MHz, DMSO-$d_6$) δ ppm 7.66 (d, J=8.6 Hz, 1 H), 6.94 (d, J=2.0 Hz, 1 H), 6.62 (dd, J=8.7, 2.1 Hz, 1 H), 6.36 (s, 2 H), 3.19 (s, 3 H). MS (m/z) 250, 252 (M+H)

Preparation 10

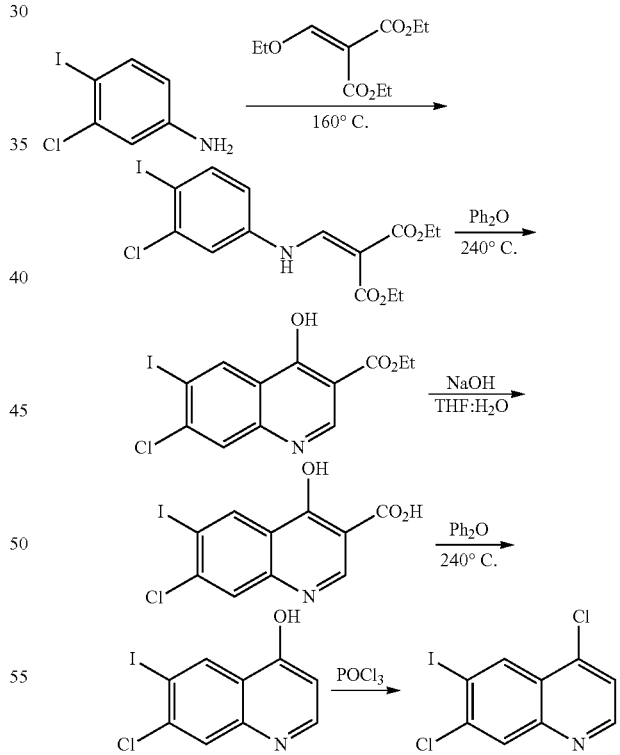

Step 1: Diethyl {[(3-chloro-4-iodophenyl)amino]methylidene}propanedioate: 3-chloro-4-iodoaniline (15 g, 59 mmol) was dissolved in diethyl [(ethyloxy)methylidene]propanedioate (19 mL, 95 mmol) and heated to 160° C. for 4 hours under a reflux condenser. The condenser was then removed to allow EtOH to boil off. After an hour, it was cooled to rt where it solidified, was broken up, and the solid suspended in hexanes. The mixture was filtered and the cake was washed several times with hexanes to afford a gray solid (23 g, 91%). MS (m/z) 424.0 (M+H)⁺.

Step 2: Ethyl 7-chloro-4-hydroxy-6-iodo-3-quinolinecarboxylate: To diphenyl ether (100 mL, 630 mmol) at 240° C. was added diethyl {[(3-chloro-4-iodophenyl)amino]methylidene}propanedioate (18 g, 43 mmol) in portions. The reaction was heated for 5 hours before it was cooled to rt. After reaching rt, the reaction was diluted with hexanes (150 mL) and the suspension was filtered. The cake was rinsed with hexanes (2×100 mL) and then dried under vacuum (6.7 g, 41%).

Step 3: 7-Chloro-4-hydroxy-6-iodo-3-quinolinecarboxylic acid: Ethyl 7-chloro-4-hydroxy-6-iodo-3-quinolinecarboxylate (6.7 g, 18 mmol) and NaOH (3.5 g, 89 mmol) were suspended in THF (50 mL) and water (50 mL). The reaction was then heated to 70° C. overnight. The mixture was cooled to rt where it was partially concentrated to remove THF. The aqueous solution was then acidified using conc HCl. The resulting suspension was filtered and the cake was washed with water (2×100 mL) and then dried under vacuum overnight to afford the desired product (6.4 g, 93%). ¹H NMR (DMSO-d₆) δ 14.78 (s, 1H), 13.47 (s, 1H), 8.97 (s, 1H), 8.70 (s, 1H), 7.99 (s, 1H).

Step 4: 7-Chloro-6-iodo-4-quinolinol: To diphenyl ether (44 mL, 276 mmol) at 240° C. was added 7-chloro-4-hydroxy-6-iodo-3-quinolinecarboxylic acid (6.4 g, 18 mmol) portion-wise. The mixture was heated for 3 hours before it was cooled to rt overnight. The reaction was diluted with hexanes (200 mL) and sonicated. The suspension was filtered and the cake was washed with hexanes (2×100 mL) and dried under vacuum to afford the desired product (4.9 g, 71%). MS (m/z) 306.0 (M+H)⁺.

Step 5: 4,7-Dichloro-6-iodoquinoline: 7-chloro-6-iodo-4-quinolinol (4.9 g, 16 mmol) was suspended in POCl₃ (50 mL, 536 mmol) and stirred at rt for 72 hours. The mixture was then concentrated and the residue was cooled to 0° C. and carefully quenched by the addition of sat aq Na₂CO₃. The resulting suspension was filtered and the cake was rinsed with water (2×50 mL). After drying the material under vacuum it was dissolved in DCM and concentrated onto silica gel. The dry load was purified by flash chromatography (20->50% EtOAc in hexanes). Concentration of fractions afforded the desired product as a white solid (3.4 g, 63%). ¹H NMR (DMSO-d₆) δ 8.90 (d, J=4.8 Hz, 1H), 8.73 (s, 1H), 8.33 (s, 1H), 7.84 (d, J=4.8 Hz, 1H); MS (m/z) 323.9 (M+H)⁺.

Preparation 11

Ethyl 3-amino-4-methyl-1H-pyrazole-5-carboxylate

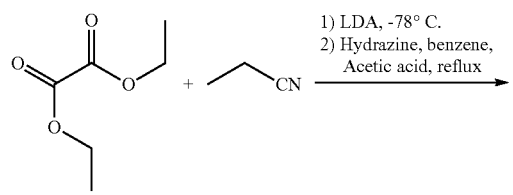

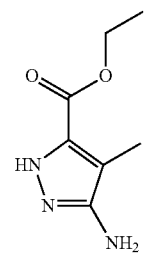

To a stirred solution of propiononitrile (1 g, 18.16 mmol) in THF (40 mL) cooled to −78° C. was added LDA in heptane/THF/ethylbenzene (10.89 mL, 21.79 mmol) dropwise. The reaction mixture was stirred for 1 hr, then added to a solution of diethyl oxalate (2.65 g, 18.16 mmol) in THF (40 mL) cooled to −78° C. The resulting solution was stirred at −78° C. for 2 h, allowed warm to 0° C. and then quenched by addition of aqueous NH₄Cl. 3N HCl was then added to achieve pH=5. The two layers were separated and the aqueous layer was extracted with EtOAc (2×100 mL). The extracts were combined, washed with brine, dried over MgSO₄, filtered, and concentrated. A yellow precipitate was formed upon partial concentration and was filtered. The remaining solvent was removed to give a brown oil. The residue oil and hydrazine (1.140 mL, 36.3 mmol) were dissolved in acetic acid (3 mL) and benzene (100 mL), and were refluxed for 16 h using Dean Stark trap. 1.5 mL of water was collected. The reaction was cooled to room temperature, and the solution was decanted away from precipitate on the bottom of the flask. The solvent was removed in vacuo, and brine (20mL) was added and then extracted with EtOAc (3×70 mL). The combined extracts were washed with water, dried over MgSO₄, filtered, and concentrated to give a colorless oil. The precipitate from the reaction was partitioned between EtOAc and saturated sodium bicarbonate and the layers were separated. The organic layer was washed with brine, dried over MgSO₄, filtered, and combined with the oil above, and the solvent was removed in vacuo to give a white solid ethyl 3-amino-4-methyl-1H-pyrazole-5-carboxylate (1.92 g, 11.35 mmol, 62.5% yield) as the desired product). ¹H NMR (Chloroform-d) δ: 4.37 (q, J=7.1Hz, 2H), 2.15 (s, 3H), 1.38 (t, J=7.2 Hz, 3H); MS (m/z) 170 (M+H⁺).

Example 1

6-(tert-Butylsulfonyl)-N-(4,5-dimethyl-1H-pyrazol-3-yl)-7-methoxyquinolin-4-amine

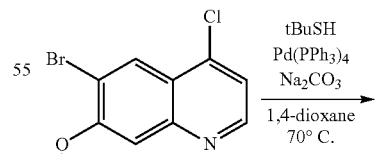

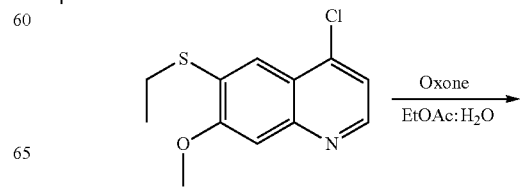

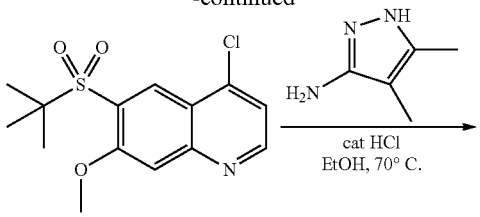

12.26 (s, 1 H), 9.32 (s, 1 H), 8.94 (s, 1 H), 8.40 (d, J=5.3 Hz, 1 H), 7.40 (s, 1 H), 6.41 (d, J=5.3 Hz, 1 H), 3.96 (s, 3 H), 2.20 (s, 3 H), 1.78 (s, 3 H), 1.24-1.38 (m, 9 H). MS (m/z) 389.

Example 2

N-(4,5-dimethyl-1H-pyrazol-3-yl)-7-(methyloxy)-6-(tetrahydro-2H-pyran-4-ylsulfinyl)-4-quinolinamine

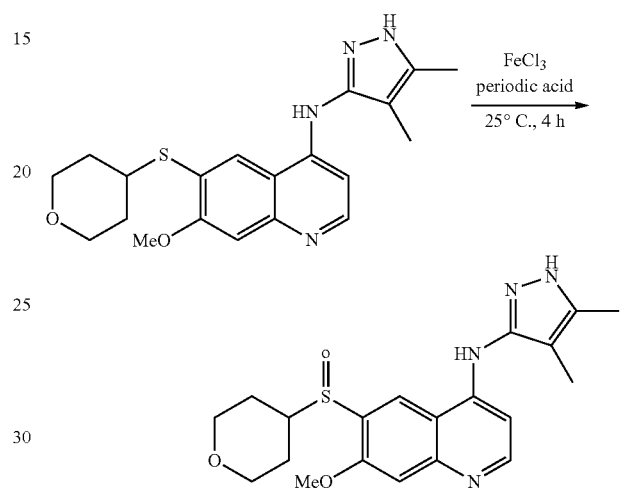

Step 1. 6-(tert-butylthio)-4-chloro-7-methoxyquinoline: A mixture of 6-bromo-4-chloro-7-methoxyquinoline (50 g, 183 mmol), Pd(Ph₃P)₄ (5.30 g, 4.59 mmol), sodium carbonate (48.6 g, 459 mmol) and 1,4-dioxane (895 mL) was purged with nitrogen for 10minutes. 2-methyl-2-propanethiol (tBuSH; 22.75 mL, 202 mmol) was added and the reaction was heated at 70° C. for 4 d. The reaction was cooled to rt and flushed through a silica gel plug that had been pre-wetted with EtOAc using 100% EtOAc as the eluent. The product-containing fractions were triturated with MeOH and combined to afford 6-(tert-butylthio)-4-chloro-7-methoxyquinoline (37.5 g, 128 mmol, 69.6% yield). ¹H NMR (400 MHz, DMSO-d₆) δ ppm 8.79 (d, J=4.8 Hz, 1 H), 8.25 (s, 1 H), 7.63 (d, J=4.8 Hz, 1 H), 7.54 (s, 1 H), 3.99(s, 3 H), 1.31 (s, 9 H). MS (m/z) 282.

Step 2. 6-(tert-butylsulfonyl)-4-chloro-7-methoxyquinoline: To a solution of 6-(tert-butylthio)-4-chloro-7-methoxyquinoline (18.5 g, 63.0 mmol) in EtOAc (315 mL) and water (315 mL) was added oxone (44.6 g, 72.5 mmol). The reaction was stirred at rt for 18 h. The layers were separated and the aqueous layer was extracted with EtOAc (2×). The combined organic extracts were concentrated to dryness, dissolved in a minimal amount of 10% MeOH/DCM, loaded onto a Biotage 340 g silica column and purified via column chromatography (Biotage SP-1, 340 g, 100% EtOAc for 20 min, then 0%-20% MeOH/EtOAc). The cleanest fractions were concentrated to dryness and triturated with EtOAc to provide 6-(tert-butylsulfonyl)-4-chloro-7-methoxyquinoline (15.2 g). ¹H NMR (400 MHz, DMSO-d₆) δ ppm 8.95 (d, J=4.8 Hz, 1 H), 8.65 (s, 1 H), 7.71-7.79 (m, 2 H), 4.04 (s, 3 H), 1.31 (s, 9 H). MS (m/z) 314.

Step 3. 6-(tert-butylsulfonyl)-N-(4,5-dimethyl-1H-pyrazol-3-yl)-7-methoxyquinolin-4-amine: To a solution of 6-(tert-butylsulfonyl)-4-chloro-7-methoxyquinoline (4.7 g, 14.98mmol) and 4,5-dimethyl-1H-pyrazol-3-amine (1.998 g, 17.97 mmol) in EtOH (74.9 mL) was added conc. HCl (2 drops). The reaction was heated at 70° C. for 42 h. The reaction was concentrated to dryness and partitioned between DCM and sat. sodium bicarbonate. The aqueous layer was extracted with DCM (1×) and the combined organic extracts were washed with brine (1×) and concentrated to dryness. The material was triturated with 1:1acetonitrile/water (60 mL) (2×) and dried in a vacuum oven overnight to afford 6-(tert-butylsulfonyl)-N-(4,5-dimethyl-1H-pyrazol-3-yl)-7-methoxyquinolin-4-amine (4.3 g, 11.07 mmol, 73.9% yield). ¹H NMR (400 MHz, DMSO-d₆) δ ppm To a solution of iron(III)chloride (1 mg, 6 umol) and N-(4,5-dimethyl-1H-pyrazol-3-yl)-7-(methyloxy)-6-(tetrahydro-2H-pyran-4-ylthio)-4-quinolinamine (80 mg, 0.21 mmol) in acetonitrile (1 mL) stirred for 5 minutes was added periodic acid (52 mg, 0.23 mmol). After 4 hours, the reaction was quenched with saturated aqueous Na₂S₂O₃ and extracted with DCM. The organic layer was concentrated and purified by silica gel chromatography (0% to 10% 2N NH₃/MeOH in DCM). Purified material contained some over oxidized sulfone and was repurified by reverse phase HPLC to give N-(4,5-dimethyl-1H-pyrazol-3-yl)-7-(methyloxy)-6-(tetrahydro-2H-pyran-4-ylsulfinyl)-4-quinolinamine (10 mg, 12%). ¹H NMR (DMSO-d₆) δ ppm 12.29 (br. s., 1H), 9.43-9.62 (br. s., 1H), 8.99 (s, 1H), 8.41 (d, J=5.6 Hz, 1H), 7.44 (s, 1H), 6.49 (s, 1H), 4.05 (s, 3H), 3.93 (d, J=11.2 Hz, 2H), 3.81 (d, J=7.3 Hz, 1H), 3.20-3.41 (m, 2H), 2.20 (s, 3H), 1.80 (s, 3H), 1.63-1.73 (m, 4H). MS (m/z) 401 (M+H⁺).

Example 3

6-[(1,1-dimethylethyl)sulfinyl]-N-(4,5-dimethyl-1H-pyrazol-3-yl)-7-(methyloxy)-4-quinolinamine

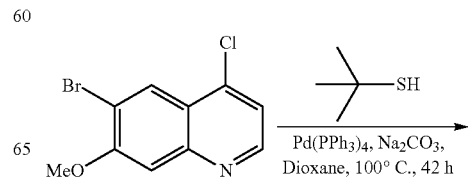

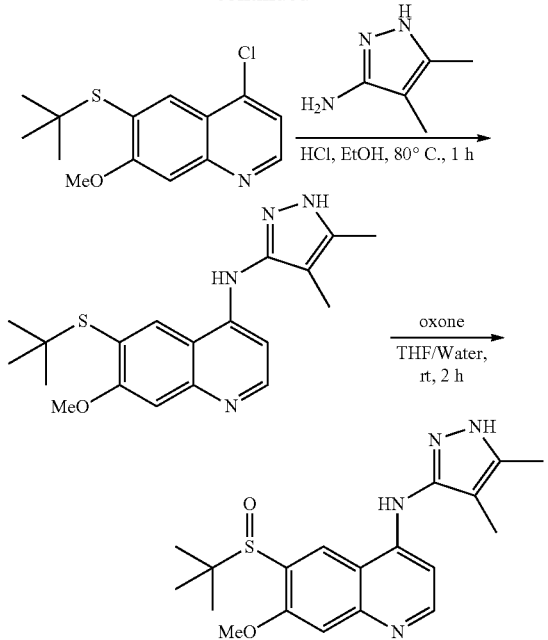

Step 1: 4-chloro-6-[(1,1-dimethylethyl)thio]-7-(methyloxy)quinoline: 6-bromo-4-chloro-7-(methyloxy)quinoline (700 mg, 2.6 mmol), sodium carbonate (1.1 g, 6.4 mmol), 1,4-dioxane (25.5 mL), tetrakis(triphenylphosphine)palladium(0) (300 mg, 0.26 mmol), and t-butylthiol (0.29 mL, 2.6 mmol) were added to microwave vial and purged with nitrogen for 10 min. After heating at 80° C. overnight, the reaction was only ~50% complete and additional tetrakis (triphenylphosphine)palladium(0) (150 mg) was added. The reaction was purged with nitrogen for 10 min, thiol (290 uL) was added and the reaction heated at 100° C. overnight. The reaction was partitioned between EtOAc and a solution of aqueous sodium thiosulfate/sodium bicarbonate (5:1, 2M). The aqueous layer was extracted with EtOAc (1×) and the combined organic extracts were dry-loaded onto silica. The crude product was purified via column chromatography (ISCO-Rf (0-100% EtOAc/hexane)) to afford 4-chloro-6-[(1,1-dimethylethyl)thio]-7-(methyloxy)quinoline (260 mg, 0.91 mmol, 36% yield). $^1$H NMR (400 MHz, DMSO-d$_6$) δ ppm 8.79 (d, J=4.8 Hz, 1 H), 8.26 (s, 1 H), 7.63 (d, J=4.8 Hz, 1 H), 7.55 (s, 1 H), 3.99 (s, 3 H), 1.32 (s, 9 H). MS (m/z) 282 (M+H)

Step 2: 6-[(1,1-dimethylethyl)thio]-N-(4,5-dimethyl-1H-pyrazol-3-yl)-7-(methyloxy)-4-quinolinamine: A mixture of 4-chloro-6-[(1,1-dimethylethyl)thio]-7-(methyloxy)quinoline (250 mg, 0.89 mmol), 4,5-dimethyl-1H-pyrazol-3-amine (99 mg, 0.89mmol) and EtOH (8.9 mL) was treated with 2 drops of concentrated HCl and heated at 80° C. for 1 h. The reaction was concentrated to dryness, suspended in DCM and filtered to provide 6-[(1,1-dimethylethyl)thio]-N-(4,5-dimethyl-1H-pyrazol-3-yl)-7-(methyloxy)-4-quinolinamine (175 mg, 0.45 mmol, 50% yield) as the HCl salt. $^1$H NMR (400 MHz, DMSO-d$_6$) δ ppm 14.05 (d, J=1.5 Hz, 1 H), 12.67 (s, 1 H), 10.68 (s, 1 H), 8.92 (s, 1 H), 8.44 (d, J=6.8 Hz, 1 H), 7.42 (s, 1 H), 6.66 (d, J=7.1 Hz, 1 H), 4.00 (s, 3 H), 2.24 (s, 3 H), 1.84 (s, 3 H), 1.30 (s, 9 H). MS (m/z) 357 (M+H)

Step 3: 6-[(1,1-dimethylethyl)sulfinyl]-N-(4,5-dimethyl-1H-pyrazol-3-yl)-7-(methyloxy)-4-quinolinamine: A mixture of 6-[(1,1-dimethylethyl)thio]-N-(4,5-dimethyl-1H-pyrazol-3-yl)-7-(methyloxy)-4-quinolinamine (184 mg, 0.52 mmol), THF (4.9 mL), water (246 µl) and oxone (159 mg, 0.258 mmol) was stirred at rt for 2 h. The reaction was partitioned between EtOAc and saturated sodium bicarbonate. The aqueous layer was extracted with EtOAc (1×) and the combined organics were dry-loaded onto silica gel and purified via column chromatography (ISCO-Rf, 12 g, 0-20% MeOH/DCM) which provided 96 mg of desired product and 65 mg of 1:1 SM/Pdt. The 65 mg of 1:1 SM/Pdt was treated with THF (2 mL), water (0.2 mL) and oxone (30 mg). The reaction was stirred for 1 h. Again, the reaction was partitioned between EtOAc and saturated sodium bicarbonate. The aqueous layer was extracted with EtOAc (1×) and the combined organics were combined with the 96 mg of 92% pure material, dry-loaded onto silica gel and purified via column chromatography (ISCO-Rf, 4 g, 0-20% MeOH/DCM) to provide 6-[(1,1-dimethylethyl)sulfinyl]-N-(4,5-dimethyl-1H-pyrazol-3-yl)-7-(methyloxy)-4-quinolinamine (90 mg, 0.24 mmol, 47% yield). $^1$H NMR (400 MHz, DMSO-d$_6$) δ ppm 12.21 (s, 1 H), 9.13(s, 1 H), 8.66 (s, 1 H), 8.34 (d, J=5.6 Hz, 1 H), 7.32 (s, 1 H), 6.40 (d, J=5.3 Hz, 1 H), 3.86-3.98 (m, 3 H), 2.20 (s, 3 H), 1.78 (s, 3 H), 1.17 (s, 9 H). MS (m/z) 373 (M+H)

The sulfone can be generated in step three by adding a full equivalent of oxone. The following examples were made in an analogous manner beginning with the appropriate quinoline from the Preparations above and/or commercial sources:

| Ex. | Structure | Name | MS (M + H)$^+$ | NMR |
|---|---|---|---|---|
| 4 | ![structure] | 2-((4-((4,5-dimethyl-1H-pyrazol-3-yl)amino)-7-methoxyquinolin-6-yl)sulfonyl)-2-methylpropan-1-ol | 405 | $^1$H NMR (400 MHz, DMSO-d6) Shift: 12.27 (s, 1 H), 9.30 (s, 1 H), 8.91 (s, 1 H), 8.40 (d, J = 5.3 Hz, 1 H), 7.39 (s, 1 H), 6.40 (d, J = 5.3 Hz, 1 H), 4.88 (t, J = 6.1 Hz, 1 H), 3.96 (s, 3 H), 3.59 (d, J = 6.1 Hz, 2 H), 2.20 (s, 3 H), 1.79 (s, 3 H), 1.28 (s, 6 H) |

Example 5

N-(4,5-dimethyl-1H-pyrazol-3-yl)-7-methoxy-6-((tetrahydro-2H-pyran-4-yl)sulfonyl)quinolin-4-amine

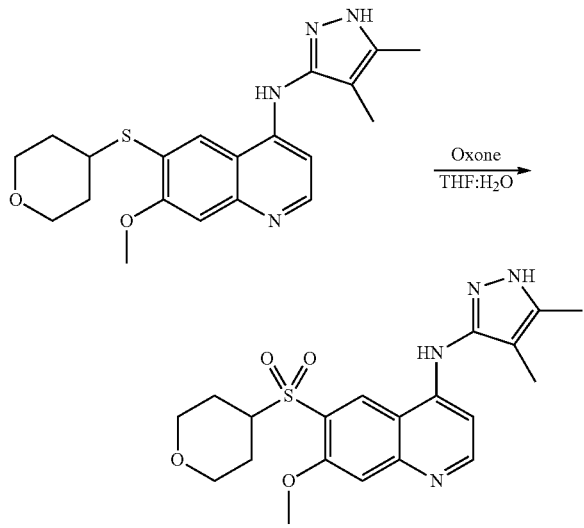

N-(4,5-dimethyl-1H-pyrazol-3-yl)-7-(methyloxy)-6-(tetrahydro-2H-pyran-4-ylthio)-4-quinolinamine (150 mg, 0.39 mmol) and oxone (240 mg, 0.39 mmol) were taken up in THF (1 mL) and water (1 mL) and stirred at room temperature. Once complete by LCMS, the reaction was concentrated, dissolved in MeOH, and purified by reverse phase HPLC. Desired fractions were neutralized using a MP-carbonate resin which was filtered off and rinsed with MeOH. The filtrate was concentrated and the residue was dissolved in 2 mL of water and MeCN each. The solution was sonicated and the resulting suspension was filtered and dried under vacuum to provide the title compound (29 mg, 17%). $^1$H NMR (DMSO-$d_6$) δ 12.25 (br. s., 1H), 9.29 (br. s., 1H), 8.96 (s, 1H), 8.41 (d, J=5.3 Hz, 1H), 7.44 (s, 1H), 6.46 (d, J=4.8 Hz, 1H), 4.04 (s, 3H), 3.88-3.98 (m, 2H), 3.74-3.88 (m, 1H), 3.32-3.41 (m, 2H), 2.20 (s, 3H), 1.80 (s, 3H), 1.69 (m, 4H); MS (m/z) 417 (M+H$^+$).

Alternatively, EtOAc or MeOH may be used as the organic component in the solvent mixture in ratios varying from 4:1 to 1:1 organic:aqueous.

The following examples were made in an analogous manner beginning with the appropriate quinoline from the Preparations above or commercial sources:

| Ex. | Structure | Name | MS (M + H)$^+$ | NMR |
|---|---|---|---|---|
| 6 | 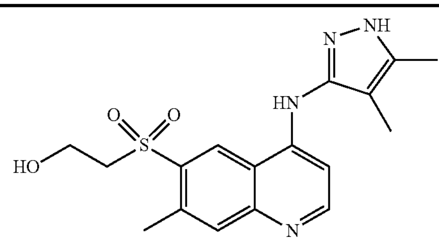 | 2-((4-((4,5-dimethyl-1H-pyrazol-3-yl)amino)-7-methylquinolin-6-yl)sulfonyl)ethanol | 361 | $^1$H NMR (DMSO-d6) Shift: 12.36 (br. s., 1H), 9.62 (br. s., 1H), 9.07 (s, 1H), 8.47 (d, J = 5.8 Hz, 1H), 7.83 (s, 1H), 6.56 (d, J = 5.3 Hz, 1H), 4.86 (br. s., 1H), 3.77 (m, 2H), 3.58 (t, J = 6.1 Hz, 2H), 2.77 (s, 3H), 2.21 (s, 3H), 1.81 (s, 3H) |
| 7 | 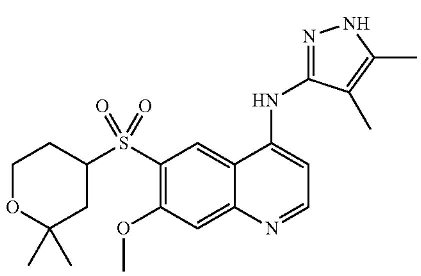 [SMILES: COc1cc2nccc(Nc3n[nH]c(C)c3C)c2cc1S(=O)(=O)C1CCOC(C)(C)C1] | N-(4,5-dimethyl-1H-pyrazol-3-yl)-6-((2,2-dimethyltetrahydro-2H-pyran-4-yl)sulfonyl)-7-methoxyquinolin-4-amine | 445 | $^1$H NMR (400 MHz, METHANOL-d4) Shift: 8.95 (s, 1H), 8.39 (d, J = 5.8 Hz, 1H), 7.44 (s, 1H), 6.49 (br. s., 1H), 4.13 (s, 3H), 4.02-4.09 (m, 1H), 3.67-3.88 (m, 2H), 2.30 (s, 3H), 1.90 (s, 3H), 1.78-1.86 (m, 2H), 1.64-1.72 (m, 2H), 1.24 (s, 6H) |
| 8 | 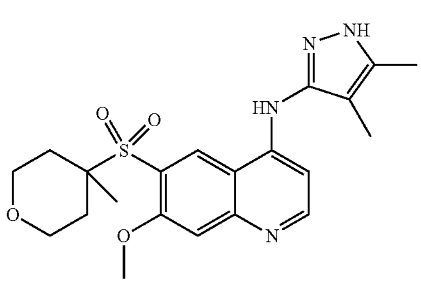 [SMILES: COc1cc2nccc(Nc3n[nH]c(C)c3C)c2cc1S(=O)(=O)C1(C)CCOCC1] | N-(4,5-Dimethyl-1H-pyrazol-3-yl)-7-methoxy-6-((4-methyltetrahydro-2H-pyran-4-yl)sulfonyl)quinolin-4-amine | 431 | $^1$H NMR (400 MHz, DMSO-$d_6$) δ 1.41 (s, 3H) 1.42-1.50 (m, 2H) 1.79 (s, 3H) 2.09-2.19 (m, 2H) 2.20 (s, 3H) 3.41-3.52 (m, 2H) 3.80-3.89 (m, 2H) 3.96 (s, 3H) 6.37-6.46 (m, 1H) 7.41 (s, 1H) 8.37-8.47 (m, 1H), 8.93 (s, 1H) 9.37 (br. s., 1H) 12.28 (br. s, 1H) |

| Ex. | Structure | Name | MS (M + H)+ | NMR |
|---|---|---|---|---|
| 9 | 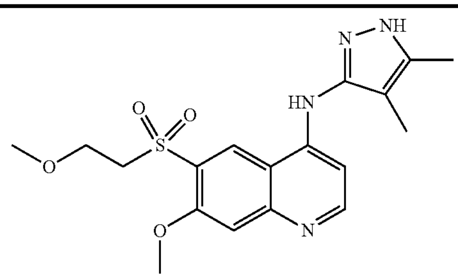 | N-(4,5-Dimethyl-1H-pyrazol-3-yl)-7-methoxy-6-((2-methoxyethyl)sulfonyl)quinolin-4-amine | 391 | ¹H NMR (400 MHz, DMSO-d₆) δ 1.80 (s, 3H) 2.20 (s, 3H) 3.09 (s, 3H) 3.67 (t, J = 5.31 Hz, 2H) 3.74 (t, J = 5.56 Hz, 2H), 4.05 (s, 3H), 6.47 (d, J = 5.31 Hz, 1H) 7.42 (s, 1H) 8.40 (d, J = 5.56 Hz, 1H) 8.96 (s, 1H) 9.26 (br. s., 1H) 12.25 (br. s., 1H) |
| 10 | 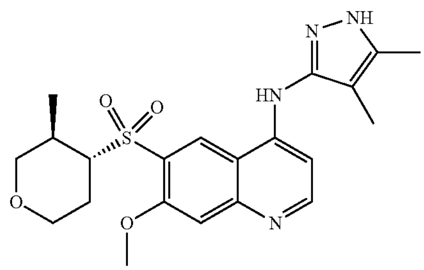 [SMILES: COc1cc2nccc(Nc3n[nH]c(C)c3C)c2cc1S(=O)(=O)[C@@H]1CCOC[C@H]1C] | N-(4,5-Dimethyl-1H-pyrazol-3-yl)-7-methoxy-6-(((3R,4R)-3-methyltetrahydro-2H-pyran-4-yl)sulfonyl)quinolin-4-amine | 431 | ¹H NMR (400 MHz, METHANOL-d₄) δ 1.25 (d, J = 7.33 Hz, 3H) 1.59-1.68 (m, 1H) 1.89 (s, 3H) 2.15-2.26 (m, 2H) 2.29 (s, 3H) 3.03 (s, 3H) 3.38-3.47 (m, 1H) 3.55-3.62 (m, 1H) 3.72-3.80 (m, 1H) 3.97-4.08 (m, 2H) 6.48 (d, J = 5.81 Hz, 1H) 7.44 (s, 1H) 8.39 (d, 5.81 Hz, 1H) 8.96 (s, 1H) |
| 11 | 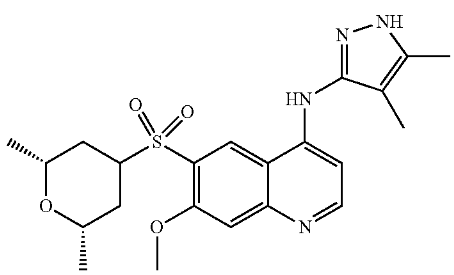 | N-(4,5-dimethyl-1H-pyrazol-3-yl)-6-(((2R,6S)-2,6-dimethyltetrahydro-2H-pyran-4-yl)sulfonyl)-7-methoxyquinolin-4-amine | 445 | ¹H NMR (500 MHz, DMSO-d₆) δ 1.05 (d, J = 6.23 Hz, 6H) 1.50-1.63 (m, 2H) 1.78 (s, 3H) 1.98 (d, J = 14.62 Hz, 2H) 2.19 (s, 3H) 3.89-3.95 (m, 1H) 3.96-4.06 (m, 5H) 6.42 (br. s., 1H) 7.43 (s, 1H) 8.41 (br. s., 1H) 8.99 (s, 1H) 9.33 (br. s., 1H) 12.26 (br. s., 1H) |

Example 12

6-(tert-butylsulfonyl)-4-((4,5-dimethyl-1H-pyrazol-3-yl)amino)quinolin-7-ol

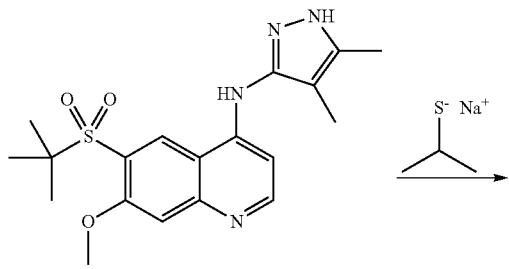

A solution of 6-(tert-butylsulfonyl)-N-(4,5-dimethyl-1H-pyrazol-3-yl)-7-methoxyquinolin-4-amine (170 mg, 0.44 mmol) and sodium propane-2-thiolate (260 mg, 2.6 mmol) was heated at 150° C. in DMF for 3 h. The residue was purified by reverse phase chromatography (6% to 75% 0.1% TFA in MeCN in 0.1% TFA in water; Sum 30×150 mm Waters Sunfire column). The fractions were collected and concentrated to an oil. The crude mixture was purified with preparatory TLC (elution with 10% NH₄OH in iPrOH). The desired spot was scraped off, the product dissolved in MeOH, filtered and the product was isolated as a yellow solid 6-(tert-butylsulfonyl)-4-((4,5-dimethyl-1H-pyrazol-3-yl)amino)quinolin-7-ol (23 mg, 14% yield) by evaporation of the solvent. ¹H NMR (400 MHz, methanol-d₄) δ=8.86 (s, 1 H), 8.04 (d, J=6.6 Hz, 1 H), 6.96 (s, 1 H), 6.27 (d, J=6.6Hz, 1 H), 2.30 (s, 3 H), 1.44 (s, 9 H), 1.93 (s, 3 H). MS (m/z) 375 (M+H⁺).

Example 13

6-(tert-butylsulfonyl)-N-(5-fluoro-1H-pyrazolo[3,4-1)]pyridin-3-yl)-7-methoxyquinolin-4-amine

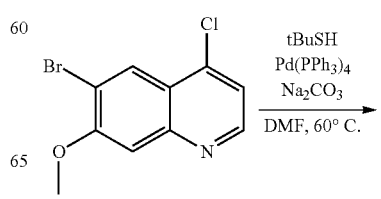

-continued

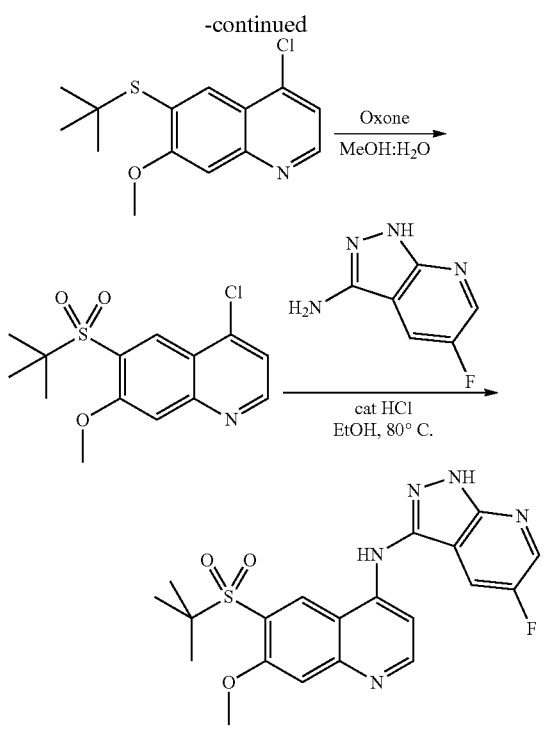

Step 1: 4-chloro-6-[(1,1-dimethylethyl)thio]-7-(methyloxy)quinoline:

Method A: 6-bromo-4-chloro-7-(methyloxy)quinoline (1.87 g, 5.42 mmol), sodium carbonate (1.44 g, 13.55 mmol), and Pd(PPh$_3$)$_4$ (0.31 g, 0.27 mmol) in DMF (30 mL) were deoxygenated for 10 minutes in a sealed tube. 2-methyl-2-propanethiol (0.62 mL, 5.42 mmol) was added. The mixture was heated to 60° C. overnight. The reaction mixture was partitioned between EtOAc and a saturated solution of sodium thiosulfate and sodium bicarbonate (v/v 5:1). The aqueous layer was extracted with EtOAc twice and the combined EtOAc layers were washed with brine, dried over sodium sulfate, filtered, and concentrated. The residue was purified by flash chromatography (0-35% EtOAc/Hexane) to yield the title compound (1.51 g, 85%). MS (m/z) 282 (M+H)$^+$. Alternatively, this reaction can be run using NaHCO$_3$ as the base or using 1,4-dioxane as the solvent. Reaction temperatures vary from 50° C. to 100° C. based on the substrate.

Method B: Alternatively, coupling reactions may be performed as follows: To a solution of quinoline (1 eq) in dioxane (0.1 M) was added (oxydibenzene-2,1-diyl)bis(diphenylphosphane) (0.1 eq), tris(dibenzylideneacetone)dipalladium(0) (0.1 eq), potassium tert-butoxide (1.25 eq), thiol (1.2 eq), and triethylamine (3 eq). The flask was purged with nitrogen, and heated under nitrogen for 3 h at 90° C. before pouring into EtOAc. The organic layer was washed with saturated sodium bicarbonate. The aqueous layer was washed with 25% EtOH in methylene chloride, then methylene chloride. The organics were combined, dried over MgSO$_4$ and concentrated to a brown oil. The residue was purified via Isco CombiFlash.

Step 2: 4-chloro-6-[(1,1-dimethylethyl)sulfonyl]-7-(methyloxy)quinoline: 4-Chloro-6-[(1,1-dimethylethyl)thio]-7-(methyloxy)quinoline (1.03 g, 3.66 mmol) and oxone (3.37 g, 5.48 mmol) in MeOH (10 mL) and water (10 mL) were stirred at rt. Once the reaction was complete it was filtered, and the cake was washed with MeOH. The filtrate was concentrated, dissolved in EtOAc, dried over sodium sulfate, then filtered and concentrated. The residue was purified via flash chromatography (0-50% EtOAc/Hexane) to yield the title compound (0.46 g, 39% yield). MS (m/z) 314 (M+H)$^+$. Alternatively this reaction can be done using a THF:Water or EtOAc:Water solvent system (4:1, 2:1, or 1:1).

Step 3: 6-(tert-butylsulfonyl)-N-(5-fluoro-1H-pyrazolo[3,4-b]pyridin-3-yl)-7-methoxyquinolin-4-amine: 4-Chloro-6-[(1,1-dimethylethyl)sulfonyl]-7-(methyloxy)quinoline (200 mg, 0.64 mmol), 5-fluoro-1H-pyrazolo[3,4-b]pyridin-3-amine (97mg, 0.64 mmol), and EtOH (1.5 mL) were combined along with 2 drops of concentrated HCl and heated to 80° C. overnight. The mixture was diluted with MeOH:Et$_2$O and filtered. The cake was rinsed with Et$_2$O. The collected solid was then dissolved in MeOH and free based using MP-carbonate resin. The resin was filtered off and rinsed with MeOH. The filtrate was concentrated to afford the desired product as a yellow solid (93 mg, 32%). $^1$H NMR (DMSO-d$_6$) δ 13.54 (br. s., 1H), 10.01 (s, 1H), 9.05 (s, 1H), 8.62 (br. s., 1H), 8.57 (d, J=5.3 Hz, 1H), 8.17 (d, J=8.8 Hz, 1H), 7.50 (s, 1H), 7.28 (d, J=5.3 Hz, 1H), 3.99 (s, 3H), 1.33 (s, 9H); MS (m/z) 430 (M+H)$^+$.

Alternatively this reaction can be done using NMP or isopropyl alcohol as the solvent and/or by heating to 150° C. in a microwave reactor. When using NMP as solvent, the reaction mixture is injected directly onto a reverse phase HPLC for purification.

The following examples were made in an analogous manner beginning with the appropriate quinoline from the above preparations and/or commercial sources:

| Ex | Structure | Name | MS (M + H)$^+$ | NMR | Step 1 Method |
|---|---|---|---|---|---|
| 14 | 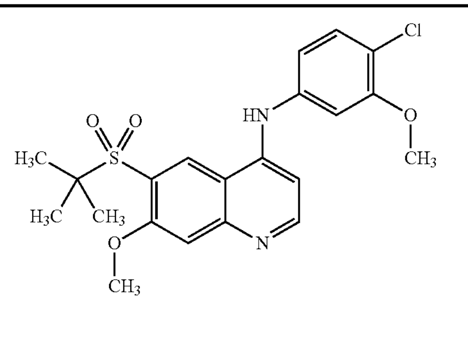 | N-[4-chloro-3-(methyloxy)phenyl]-6-[(1,1-dimethylethyl)sulfonyl]-7-(methyloxy)-4-quinolinamine | 455 | $^1$H NMR (400 MHz, DMSO-d) δ ppm 1.31 (s, 9H), 3.86 (s, 3H), 3.97 (s, 3H), 6.95 (d, J = 5.3 Hz, 1H), 6.97 (dd, J = 8.7 Hz, 1.9 Hz, 1H), 7.12 (d, J = 2.1 Hz, 1H), 7.44 (d, J = 8.4 Hz, 1H), 7.46 (s, 1H), 8.51 (d, J = 5.6 Hz, 1H), 8.88 (s, 1H), 9.54 (s, 1H). | A |

-continued

The following examples were made in an analogous manner beginning with the appropriate quinoline from the above preparations and/or commercial sources:

| Ex | Structure | Name | MS (M + H)+ | NMR | Step 1 Method |
|---|---|---|---|---|---|
| 15 | 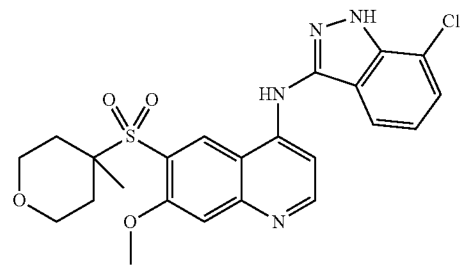 [SMILES: COc1cc2nccc(Nc3n[nH]c4c(Cl)cccc34)c2cc1S(=O)(=O)C1(C)CCOCC1] | N-(7-Chloro-1H-indazol-3-yl)-7-methoxy-6-((4-methyltetrahydro-2H-pyran-4-yl)sulfonyl)quinolin-4-amine | 487 | $^1$H NMR (400 MHz, DMSO-d$_6$) δ 1.42 (s, 3H) 1.49 (s, 2H) 2.09-2.23 (m, 2H) 3.47 (s, 2H) 3.79-3.89 (m, 2H) 3.99 (s, 3H) 7.07-7.20 (m, 2H) 7.47-7.57 (m, 2H) 7.76 (d, J = 8.08 Hz, 1H) 8.55 (d, J = 5.05 Hz, 1H) 9.07 (s, 1H) 10.05 (s, 1H) 13.36 (br. s., 1H) | B |
| 16 | 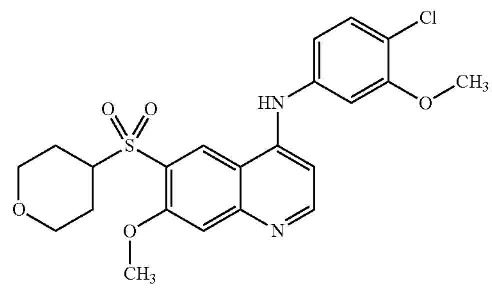 [SMILES: COc1cc(Nc2ccnc3cc(OC)c(S(=O)(=O)C4CCOCC4)cc23)ccc1Cl] | N-[4-chloro-3-(methyloxy)phenyl]-7-(methyloxy)-6-(tetrahydro-2H-pyran-4-ylsulfonyl)-4-quinolinamine | 463 | $^1$H NMR (400 MHz, DMSO-d6) δ ppm 9.56 (s, 1H), 8.89 (s, 1H), 8.53 (d, J = 5.3 Hz, 1H), 7.50 (s, 1H), 7.43 (d, J = 8.3 Hz, 1H), 7.13 (d, J = 2.3 Hz, 1H), 6.95-7.02 (m, 2H), 4.06 (s, 3H), 3.93 (d, J = 10.9 Hz, 2H), 3.86 (s, 4H), 3.36 (br. s., 2H), 1.69 (d, 4H) | A |
| 17 | 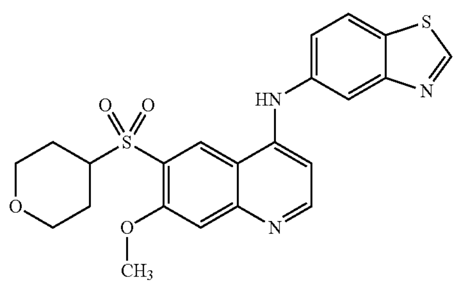 [SMILES: COc1cc2nccc(Nc3ccc4scnc4c3)c2cc1S(=O)(=O)C1CCOCC1] | N-1,3-benzothiazol-5-yl-7-(methyloxy)-6-(tetrahydro-2H-pyran-4-ylsulfonyl)-4-quinolinamine | 456 | $^1$H NMR (400 MHz, DMSO-d6) δ ppm 9.72 (s, 1H), 9.44 (s, 1H), 8.95 (s, 1H), 8.51 (d, J = 5.3 Hz, 1H), 8.21 (d, J = 8.6 Hz, 1H), 8.03 (d, J = 2.0 Hz, 1H), 7.49-7.57 (m, 2H), 6.94 (d, J = 5.3 Hz, 1H), 4.07 (s, 3H), 3.94 (d, J = 7.6 Hz, 2H), 3.80-3.89 (m, 1H), 3.35-3.41 (m, 2H), 1.67-1.73 (m, 4H) | A |
| 18 | 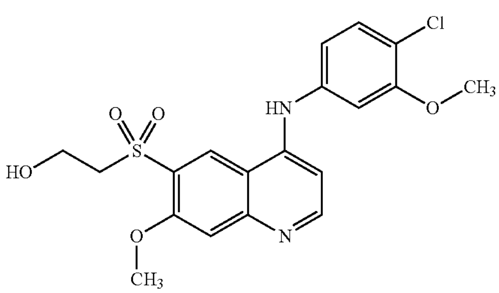 [SMILES: COc1cc(Nc2ccnc3cc(OC)c(S(=O)(=O)CCO)cc23)ccc1Cl] | 2-{[4-{[4-chloro-3-(methyloxy)phenyl]amino}-7-(methyloxy)-6-quinolinyl]sulfonyl}ethanol | 423 | $^1$H NMR (400 MHz, DMSO-d6) δ ppm 9.54 (s, 1H), 8.87 (s, 1H), 8.53 (d, J = 5.3 Hz, 1H), 7.48 (s, 1H), 7.43 (d, J = 8.3 Hz, 1H), 7.13 (d, J = 2.3 Hz, 1H), 6.95-7.03 (m, 2H), 4.83 (t, J = 5.3 Hz, 1H), 4.06 (s, 3H), 3.86 (s, 3H), 3.62-3.75 (m, 4H) | A |
| 19 | 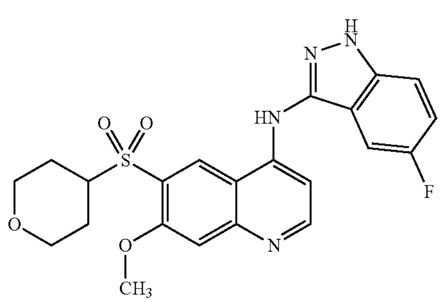 [SMILES: COc1cc2nccc(Nc3n[nH]c4ccc(F)cc34)c2cc1S(=O)(=O)C1CCOCC1] | N-(5-fluoro-1H-indazol-3-yl)-7-(methyloxy)-6-(tetrahydro-2H-pyran-4-ylsulfonyl)-4-quinolinamine | 457 | $^1$H NMR (400 MHz, DMSO-d6) δ ppm 12.91 (s, 1H), 9.87 (s, 1H), 9.08 (s, 1H), 8.54 (d, J = 5.3 Hz, 1H), 7.54-7.65 (m, 2H), 7.52 (s, 1H), 7.31 (td, 1H), 7.21 (d, J = 5.3 Hz, 1H), 4.07 (s, 3H), 3.94 (d, J = 11.1 Hz, 2H), 3.80-3.89 (m, 1H), 3.37 (d, J = 5.3 Hz, 2H), 1.65-1.75 (m, 4H) | A |

-continued

The following examples were made in an analogous manner beginning with the appropriate quinoline from the above preparations and/or commercial sources:

| Ex | Structure | Name | MS (M + H)+ | NMR | Step 1 Method |
|---|---|---|---|---|---|
| 20 | 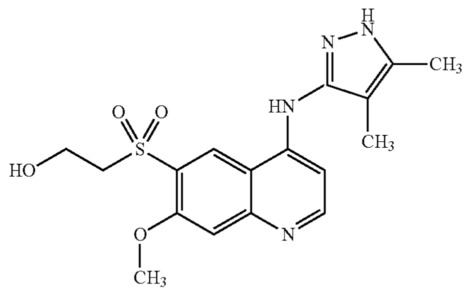 | 2-{[4-[(4,5-dimethyl-1H-pyrazol-3-yl)amino]-7-(methyloxy)-6-quinolinyl]sulfonyl}ethanol | 377 | $^1$H NMR (400 MHz, DMSO-d6) δ ppm 12.23 (s, 1H), 9.24 (s, 1H), 8.95 (s, 1H), 8.40 (d, J = 5.3 Hz, 1H), 7.42 (s, 1H), 6.47 (d, J = 5.3 Hz, 1H), 4.83 (t, J = 5.4 Hz, 1H), 4.04 (s, 3H), 3.59-3.77 (m, 4H), 2.20 (s, 3H), 1.80 (s, 3H) | A |
| 21 | 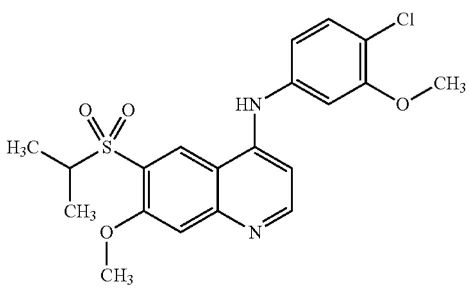 [SMILES: COc1cc(Nc2ccnc3cc(OC)c(S(=O)(=O)C(C)C)cc23)ccc1Cl] | N-[4-chloro-3-(methyloxy)phenyl]-6-[(1-methylethyl)sulfonyl]-7-(methyloxy)-4-quinolinamine | 421 | $^1$H NMR (400 MHz, DMSO-d6) δ ppm 9.55 (s, 1H), 8.89 (s, 1H), 8.53 (d, J = 5.6 Hz, 1H), 7.50 (s, 1H), 7.43 (d, J = 8.6 Hz, 1H), 7.13 (d, J = 2.3 Hz, 1H), 6.94-7.03 (m, 2H), 4.05 (s, 3H), 3.86 (s, 3H), 3.74-3.83 (m, 1H), 1.21 (d, J = 6.8 Hz, 6H) | A |
| 22 | 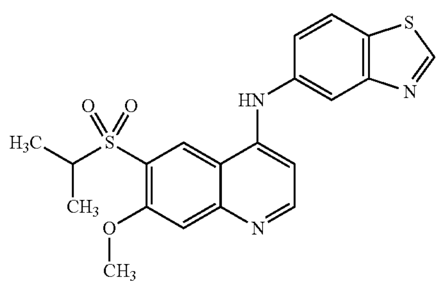 [SMILES: COc1cc2nccc(Nc3ccc4scnc4c3)c2cc1S(=O)(=O)C(C)C] | N-1,3-benzothiazol-5-yl-6-[(1-methylethyl)sulfonyl]-7-(methyloxy)-4-quinolinamine | 414 | $^1$H NMR (400 MHz, DMSO-d6) δ ppm 9.71 (s, 1H), 9.43 (s, 1H), 8.96 (s, 1H), 8.51 (d, J = 5.3 Hz, 1H), 8.20 (d, J = 8.6 Hz, 1H), 8.04 (d, J = 2.0 Hz, 1H), 7.46-7.61 (m, 2H), 6.94 (d, J = 5.3 Hz, 1H), 4.06 (s, 3H), 3.71-3.89 (m, 1H), 1.23 (d, 6H) | A |
| 23 | 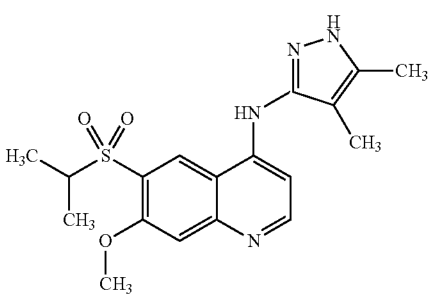 | N-(4,5-dimethyl-1H-pyrazol-3-yl)-6-[(1-methylethyl)sulfonyl]-7-(methyloxy)-4-quinolinamine | 375 | $^1$H NMR (400 MHz, DMSO-d6) δ ppm 12.23 (s, 1H), 9.26 (s, 1H), 8.96 (s, 1H), 8.40 (d, J = 5.3 Hz, 1H), 7.43 (s, 1H), 6.47 (d, J = 5.6 Hz, 1H), 4.03 (s, 3H), 3.72-3.82 (m, 1H), 2.20 (s, 3H), 1.80 (s, 3H), 1.22 (d, J = 6.8 Hz, 6H) | A |
| 24 | 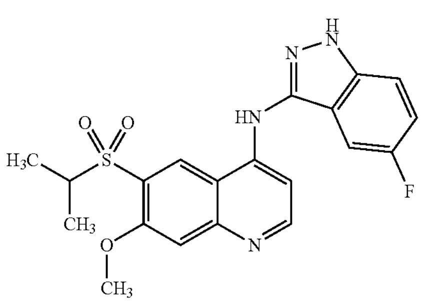 [SMILES: COc1cc2nccc(Nc3n[nH]c4ccc(F)cc34)c2cc1S(=O)(=O)C(C)C] | N-(5-fluoro-1H-indazol-3-yl)-6-[(1-methylethyl)sulfonyl]-7-(methyloxy)-4-quinolinamine | 415 | $^1$H NMR (400 MHz, DMSO-d6) δ ppm 12.90 (s, 1H), 9.87 (s, 1H), 9.09 (s, 1H), 8.54 (d, J = 5.6 Hz, 1H), 7.55-7.63 (m, 2H), 7.52 (s, 1H), 7.28-7.36 (m, 1H), 7.22 (d, J = 5.6 Hz, 1H), 4.06 (s, 3H), 3.76-3.85 (m, 1H), 1.23 (d, J = 6.8 Hz, 6H) | A |

The following examples were made in an analogous manner beginning with the appropriate quinoline from the above preparations and/or commercial sources:

| Ex | Structure | Name | MS (M + H)+ | NMR | Step 1 Method |
|---|---|---|---|---|---|
| 25 | 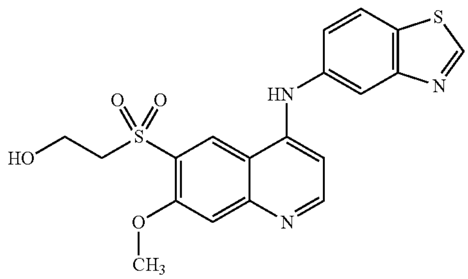 [SMILES: COc1cc2nccc(Nc3ccc4scnc4c3)c2cc1S(=O)(=O)CCO] | 2-{[4-(1,3-benzothiazol-5-ylamino)-7-(methyloxy)-6-quinolinyl]sulfonyl}ethanol | 416 | $^1$H NMR (400 MHz, DMSO-d6) δ ppm 9.70 (br. s., 1H), 9.43 (s, 1H), 8.94 (s, 1H), 8.50 (br. s., 1H), 8.19 (br. s., 1H), 8.03 (br. s., 1H), 7.48 (br. s., 2H), 6.94 (br. s., 1H), 4.86 (br. s., 1H), 4.06 (s, 3H), 3.61-3.78 (m, 4H) | A |
| 26 | 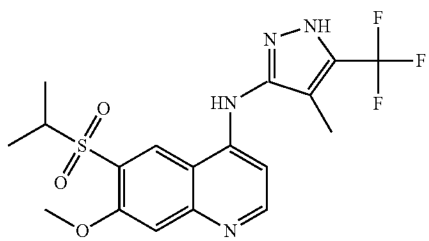 | 6-(isopropyl-sulfonyl)-7-methoxy-N-(4-methyl-5-(trifluoromethyl)-1H-pyrazol-3-yl)quinolin-4-amine | 429 | $^1$H NMR (400 MHz, DMSO-d$_6$) δ 13.65 (br. s., 1H), 9.41-9.80 (m, 1H), 8.85-9.10 (m, 1H), 8.34-8.61 (m, 1H), 7.37-7.68 (m, 1H), 6.24 (br. s., 1H), 4.05 (s, 3H), 3.81 (m, 1H), 1.87-2.05 (m, 3H), 1.22 (d, J = 6.82 Hz, 6H) | A |
| 27 | 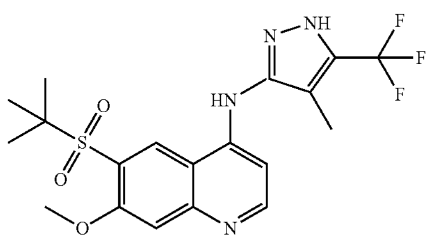 | 6-(tert-butylsulfonyl)-7-methoxy-N-(4-methyl-5-(trifluoromethyl)-1H-pyrazol-3-yl)quinolin-4-amine | 443 | $^1$H NMR (400 MHz, DMSO-d$_6$) δ 13.97 (br. s., 1H), 9.00-9.24 (m, 1H), 8.37-8.62 (m, 1H), 7.51-7.65 (m, 1H), 6.42 (br. s., 1H), 4.03 (s, 3H), 1.99 (s, 3H), 1.34 (s, 9H) | A |
| 28 | 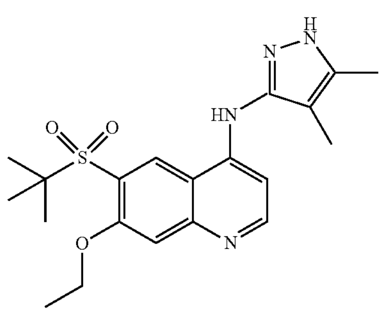 | 6-(tert-butylsulfonyl)-N-(4,5-dimethyl-1H-pyrazol-3-yl)-7-ethoxyquinolin-4-amine | 403 | $^1$H NMR (CDCl$_3$) δ 11.53 (br. s., 1H), 10.71 (br. s., 1H), 9.06 (s, 1H), 8.35 (d, J = 6.8 Hz, 1H), 8.15 (s, 1H), 6.50 (d, J = 6.8 Hz, 1H), 4.44 (q, J = 7.1 Hz, 2H), 2.35 (s, 3H), 1.83 (s, 3H), 1.57 (t, J = 7.1 Hz, 3H), 1.42 (s, 9H) | B |
| 29 | 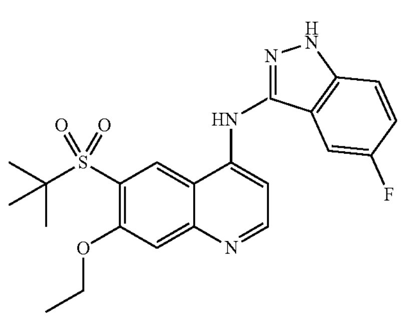 | 6-(tert-butylsulfonyl)-7-ethoxy-N-(5-fluoro-1H-indazol-3-yl)quinolin-4-amine | 443 | $^1$H NMR (400 MHz, methanol-d$_4$) δ 9.03 (s, 1H), 8.46 (d, J = 5.7 Hz, 1H), 7.58 (td, J = 9.1, 2.4 Hz, 1H), 7.46 (s, 1H), 7.38 (dd, J = 9.1, 2.4 Hz, 1H), 7.29 (td, J = 9.1, 2.4 Hz, 1H), 6.98 (d, J = 5.7 Hz, 1H), 4.28 (q, J = 7.0 Hz, 2H), 1.58 (t, J = 7.0 Hz, 3H), 1.46 (s, 9H) | B |

-continued

The following examples were made in an analogous manner beginning with the
appropriate quinoline from the above preparations and/or commercial sources:

| Ex | Structure | Name | MS (M + H)+ | NMR | Step 1 Method |
|---|---|---|---|---|---|
| 30 | 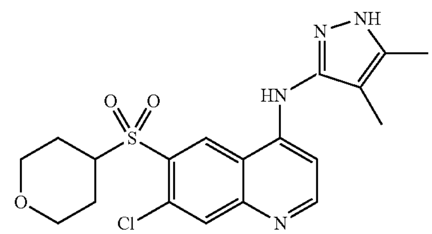 | 7-chloro-N-(4,5-dimethyl-1H-pyrazol-3-yl)-6-((tetrahydro-2H-pyran-4-yl)sulfonyl)quinolin-4-amine | 421 | $^1$H NMR (DMSO-$d_6$) 12.32 (br s, 1H), 9.56 (s, 1H), 9.16 (s, 1H), 8.52 (d, J = 5.6 Hz, 1H), 8.08 (s, 1H), 6.62 (d, J = 4.0 Hz, 1H), 3.81-4.01 (m, 2H), 3.71-3.83 (m, 1H), 3.35-3.42 (m, 2H), 2.21 (s, 3H), 1.80 (s, 3H), 1.65-1.78 (m, 4H). | A |
| 31 | 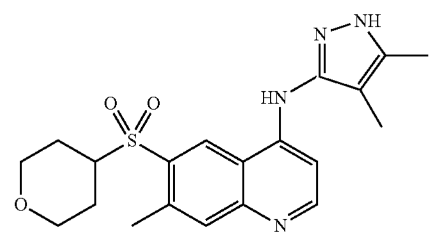 | N-(4,5-dimethyl-1H-pyrazol-3-yl)-7-methyl-6-((tetrahydro-2H-pyran-4-yl)sulfonyl)quinolin-4-amine | 401 | $^1$H NMR (DMSO-$d_6$) 12.52 (br s, 1H), 9.15 (s, 1H), 8.52 (d, J = 6.3 Hz, 1H), 7.89 (s, 1H), 6.68 (d, J = 6.3 Hz, 1H), 3.93 (m, 2H), 3.63-3.77 (m, 1H), 3.26-3.43 (m, 2H), 2.82 (s, 3H), 2.23 (s, 3H), 1.83 (s, 3H), 1.65-1.78 (m, 4H). | A |
| 32 | 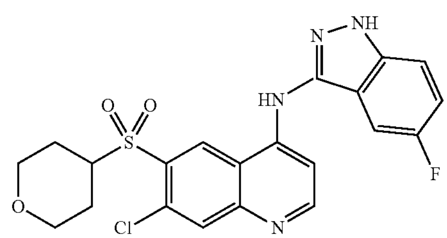 | 7-chloro-N-(5-fluoro-1H-indazol-3-yl)-6-((tetrahydro-2H-pyran-4-yl)sulfonyl)quinolin-4-amine | 461 | $^1$H NMR (DMSO-$d_6$) 9.28 (s, 1H), 8.56 (s, 1H), 8.03-8.14 (m, 1H), 7.50-7.61 (m, 2H), 7.26-7.36 (m, 2H), 3.87-4.00 (m, 3H), 3.35-3.43 (m, 2H), 1.70-1.81 (m, 4H). | A |
| 33 | 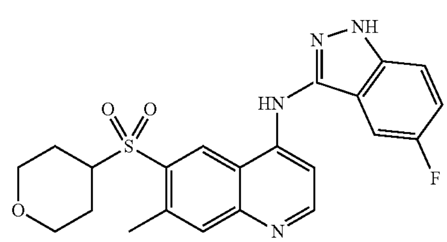 | N-(5-fluoro-1H-indazol-3-yl)-7-methyl-6-((tetrahydro-2H-pyran-4-yl)sulfonyl)quinolin-4-amine | 441 | $^1$H NMR (DMSO-$d_6$) 13.03 (s, 1H), 9.15 (s, 1H), 8.57 (d, J = 5.5 Hz, 1H), 7.92 (s, 1H), 7.60 (dd, J = 9.0, 4.3 Hz, 1H), 7.56 (dd, J = 9.0, 1.8 Hz, 1H), 7.33 (td, J = 9.0, 2.3 Hz, 1H), 7.23 (d, J = 5.8 Hz, 1H), 3.93 (m, 2H), 3.69 (tt, J = 10.2, 5.2 Hz, 1H), 3.29-3.43 (m, 2H), 2.81 (s, 3H), 1.63-1.82 (m, 4H). | A |
| 34 | 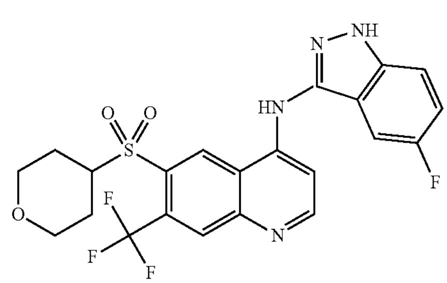 | N-(5-fluoro-1H-indazol-3-yl)-6-((tetrahydro-2H-pyran-4-yl)sulfonyl)-7-(trifluoromethyl)quinolin-4-amine | 495 | $^1$H NMR (DMSO-$d_6$) 9.33 (s, 1H), 7.47-7.58 (m, 2H), 7.38-7.45 (m, 4H), 7.31-7.36 (m, 1H), 7.20-7.29 (m, 1H), 3.88-3.99 (m, 2H), 3.51-3.64 (m, 1H), 3.26-3.32 (m, 2H), 1.69-1.84 (m, 4H). | A |

The following examples were made in an analogous manner beginning with the appropriate quinoline from the above preparations and/or commercial sources:

| Ex | Structure | Name | MS (M + H)+ | NMR | Step 1 Method |
|---|---|---|---|---|---|
| 35 | 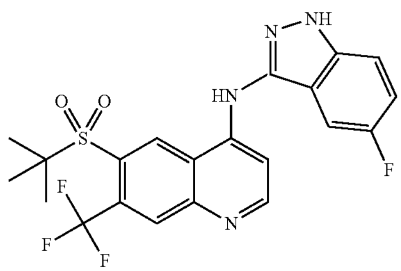 | 6-(tert-butylsulfonyl)-N-(5-fluoro-1H-indazol-3-yl)-7-(trifluoromethyl)quinolin-4-amine | 467 | $^1$H NMR (DMSO-$d_6$) 13.43 (s, 1H), 9.50 (s, 1H), 8.78 (d, J = 6.3 Hz, 1H), 8.58 (s, 1H), 7.69 (dd, J = 9.2, 4.1 Hz, 1H), 7.51 (dd, J = 8.9, 1.9 Hz, 1H), 7.39 (td, J = 9.1, 2.4 Hz, 1H), 7.28 (d, J = 6.5 Hz, 1H), 1.38 (s, 9H). | A |
| 36 | 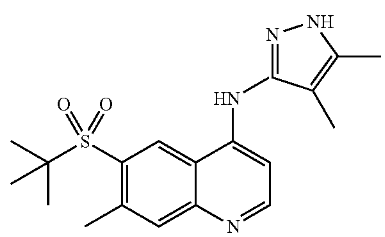 | 6-(tert-butylsulfonyl)-N-(4,5-dimethyl-1H-pyrazol-3-yl)-7-methylquinolin-4-amine | 373 | $^1$H NMR (DMSO-$d_6$) 12.27 (br s, 1H), 9.37 (br s, 1H), 8.98 (s, 1H), 8.46 (d, J = 5.1 Hz, 1H), 7.81 (s, 1H), 6.49 (d, J = 5.1 Hz, 1H), 2.75 (s, 3H), 2.20 (s, 3H), 1.78 (s, 3H), 1.32 (s, 9H). | A |
| 397 | 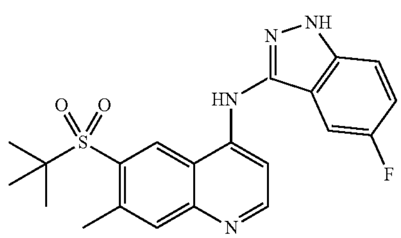 | 6-(tert-butylsulfonyl)-N-(5-fluoro-1H-indazol-3-yl)-7-methylquinolin-4-amine | 413 | $^1$H NMR (DMSO-$d_6$) 13.00 (s, 1H), 9.96 (s, 1H), 9.12 (s, 1H), 8.57 (d, J = 5.3 Hz, 1H), 7.90 (s, 1H), 7.60 (dd, J = 8.8, 4.0 Hz, 1H), 7.48 (dd, J = 9.1, 1.8 Hz, 1H), 7.32 (td, J = 9.1, 2.3 Hz, 1H), 7.12 (d, J = 5.3 Hz, 1H), 2.79 (s, 3H), 1.34 (s, 9H). | A |
| 38 | 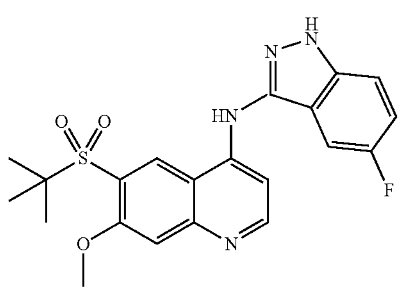 | 6-(tert-butylsulfonyl)-N-(5-fluoro-1H-indazol-3-yl)-7-methoxyquinolin-4-amine | 429 | $^1$H NMR (DMSO-$d_6$) 12.96 (br s, 1H), 9.91 (br s, 1H), 9.06 (s, 1H), 8.47-8.58 (m, 1H), 7.58 (dd, J = 9.0, 4.2 Hz, 1H), 7.45-7.54 (m, 2H), 7.31 (td, J = 9.0, 2.1 Hz, 1H), 7.06 (d, J = 5.3 Hz, 1H), 3.98 (s, 3H), 1.34 (s, 9H). | A |
| 39 | 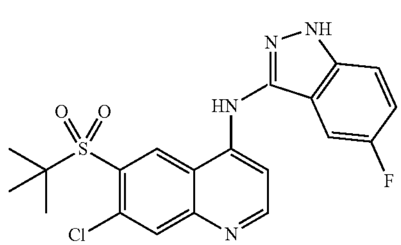 | 6-(tert-butylsulfonyl)-7-chloro-N-(5-fluoro-1H-indazol-3-yl)quinolin-4-amine | 433 | $^1$H NMR (DMSO-d6) Shift: 9.28 (s, 1H), 8.54 (br. s., 1H), 8.05 (br. s., 1H), 7.59 (dd, J = 8.5, 4.0 Hz, 1H), 7.41-7.51 (m, 1H), 7.27-7.36 (m, 1H), 7.17 (d, J = 5.3 Hz, 1H), 1.39 (s, 9H) | A |

-continued

The following examples were made in an analogous manner beginning with the appropriate quinoline from the above preparations and/or commercial sources:

| Ex | Structure | Name | MS (M + H)+ | NMR | Step 1 Method |
|---|---|---|---|---|---|
| 40 | 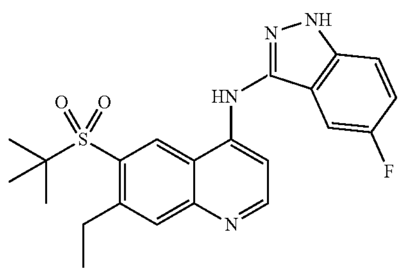 | 6-(tert-butylsulfonyl)-7-ethyl-N-(5-fluoro-1H-indazol-3-yl)quinolin-4-amine | 427 | 1H NMR (DMSO-d6) Shift: 12.98 (br. s., 1H), 9.12 (s, 1H), 8.54 (br. s., 1H), 7.91 (br. s., 1H), 7.59 (dd, J = 9.0, 4.2 Hz, 1H), 7.42-7.51 (m, 1H), 7.31 (td, J = 9.0, 2.2 Hz, 1H), 7.11 (d, J = 5.6 Hz, 1H), 3.19 (q, J = 7.3 Hz, 2H), 1.26-1.37 (m, 12H) | A |
| 41 | 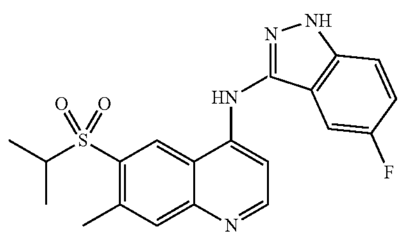 | N-(5-fluoro-1H-indazol-3-yl)-6-(isopropyl-sulfonyl)-7-methylquinolin-4-amine | 399 | 1H NMR (DMSO-d6) Shift: 9.51 (s, 1H), 9.06 (d, J = 6.1 Hz, 1H), 8.18 (s, 1H), 7.91 (d, J = 5.8 Hz, 1H), 7.83-7.90 (m, 2H), 7.49 (td, J = 9.1, 2.5 Hz, 1H), 3.63 (quin, J = 6.8 Hz, 1H), 2.85 (s, 3H), 1.21 (d, J = 6.8 Hz, 6H) | A |
| 42 | 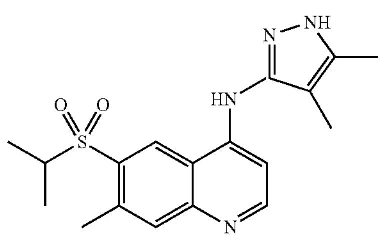 | N-(4,5-dimethyl-1H-pyrazol-3-yl)-6-(isopropyl-sulfonyl)-7-methylquinolin-4-amine | 359 | 1H NMR (DMSO-d6) Shift: 12.40 (br. s., 1H), 9.09 (s, 1H), 8.49 (d, J = 6.1 Hz, 1H), 7.86 (s, 1H), 6.52-6.68 (m, 1H), 3.59 (quin, J = 6.8 Hz, 1H), 2.77 (s, 3H), 2.21 (s, 3H), 1.81 (s, 3H), 1.23 (d, J = 6.8 Hz, 6H) | A |
| 43 | 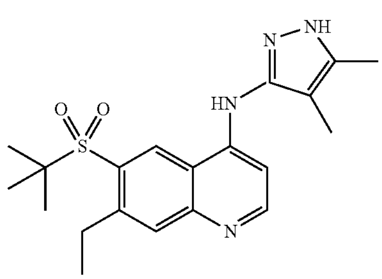 | 6-(tert-butylsulfonyl)-N-(4,5-dimethyl-1H-pyrazol-3-yl)-7-ethylquinolin-4-amine | 387 | 1H NMR (DMSO-d6) Shift: 12.45 (br. s., 1H), 9.08 (s, 1H), 8.50 (d, J = 6.0 Hz, 1H), 7.90 (s, 1H), 6.56 (d, J = 5.5 Hz, 1H), 3.18 (q, J = 7.3 Hz, 2H), 2.22 (s, 3H), 1.80 (s, 3H), 1.22-1.42 (m, 12H) | A |
| 44 | 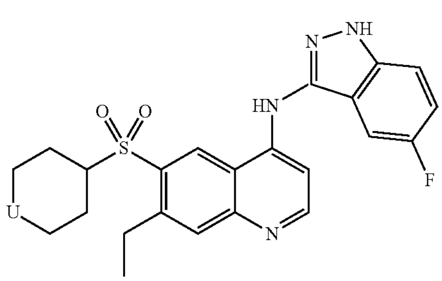 | 7-ethyl-N-(5-fluoro-1H-indazol-3-yl)-6-((tetrahydro-2H-pyran-4-yl)sulfonyl)quinolin-4-amine | 455 | 1H NMR (DMSO-d6) Shift: 9.29 (s, 1H), 8.63 (d, J = 6.6 Hz, 1H), 8.01 (s, 1H), 7.66 (dd, J = 9.0, 4.2 Hz, 1H), 7.56 (dd, J = 9.0, 2.0 Hz, 1H), 7.37 (td, J = 9.0, 2.2 Hz, 1H), 7.19 (d, J = 6.6 Hz, 1H), 3.89-3.99 (m, 2H), 3.64-3.77 (m, 1H), 3.30-3.40 (m, 2H), 3.24 (q, J = 7.2 Hz, 2H), 1.65-1.79 (m, 4H), 1.37 (t, 3H) | A |

-continued

The following examples were made in an analogous manner beginning with the appropriate quinoline from the above preparations and/or commercial sources:

| Ex | Structure | Name | MS (M + H)+ | NMR | Step 1 Method |
|---|---|---|---|---|---|
| 45 | 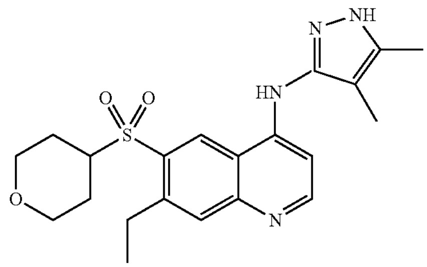 | N-(4,5-dimethyl-1H-pyrazol-3-yl)-7-ethyl-6-((tetrahydro-2H-pyran-4-yl)sulfonyl)quinolin-4-amine | 415 | $^1$H NMR (DMSO-d6) Shift: 12.29 (br. s., 1H), 9.33 (br. s., 1H), 8.99 (s, 1H), 8.48 (d, J = 5.3 Hz, 1H), 7.87 (s, 1H), 6.53 (d, J = 4.5 Hz, 1H), 3.86-4.01 (m, 2H), 3.54-3.68 (m, 1H), 3.28-3.34 (m, 2H), 3.15 (q, J = 7.3 Hz, 2H), 2.21 (s, 3H), 1.80 (s, 3H), 1.65-1.76 (m, 4H), 1.34 (t, 3H) | A |
| 46 | 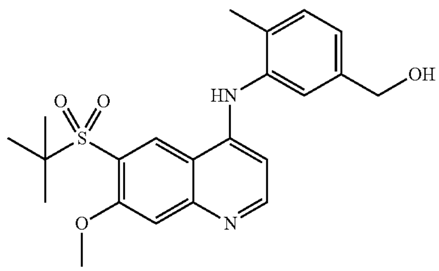 [SMILES: COc1cc2nccc(Nc3cc(CO)ccc3C)c2cc1S(=O)(=O)C(C)(C)C] | (3-((6-(tert-butylsulfonyl)-7-methoxyquinolin-4-yl)amino)-4-methylphenyl)methanol | 415 | $^1$H NMR (DMSO-d6) Shift: 9.38 (s, 1H), 8.95 (s, 1H), 8.37 (d, J = 5.3 Hz, 1H), 7.42 (s, 1H), 7.33 (d, J = 8.1 Hz, 1H), 7.18-7.23 (m, 2H), 6.00 (d, J = 5.6 Hz, 1H), 5.20 (t, J = 5.7 Hz, 1H), 4.50 (d, J = 5.6 Hz, 2H), 3.96 (s, 3H), 2.13 (s, 3H), 1.32 (s, 9H) | A |
| 47 | 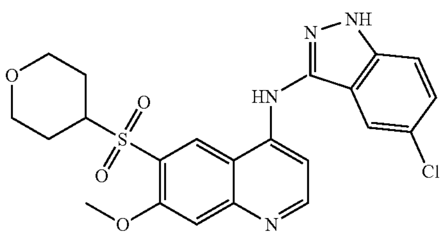 | N-(5-chloro-1H-indazol-3-yl)-7-methoxy-6-((tetrahydro-2H-pyran-4-yl)sulfonyl)quinolin-4-amine | 473 | $^1$H NMR (400 MHz, DMSO-d6) Shift: 13.04 (s, 1H), 9.14 (s, 1H), 8.56 (d, J = 5.56 Hz, 1H), 7.99 (d, J = 1.52 Hz, 1H), 7.59 (d, J = 8.84 Hz, 1H), 7.52 (s, 1H), 7.44 (d, J = 1.77 Hz, 1H), 7.42 (d, J = 2.02 Hz, 1H). 7.37 (d, J = 5.81 Hz, 1H), 4.09 (s, 3H), 3.92-3.97 (m, 2H), 3.81-3.90 (m, 1H), 3.30-3.41 (m, 2H), 1.64-1.79 (m, 4H) | B |
| 48 | 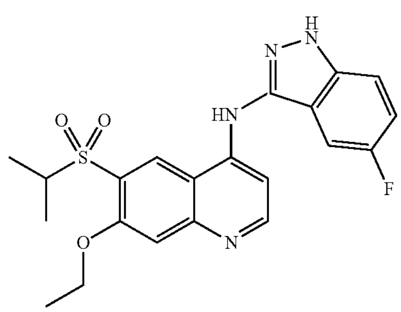 | 7-ethoxy-N-(5-fluoro-1H-indazol-3-yl)-6-(isopropyl-sulfonyl)quinolin-4-amine | 429 | $^1$H NMR (DMSO-d6) Shift: 12.86 (s, 1H), 9.86 (s, 1H), 9.05 (s, 1H), 8.49 (d, J = 5.3 Hz, 1H), 7.61 (dd, J = 11.9, 2.0 Hz, 1H), 7.53-7.58 (m, 1H), 7.31 (td, J = 9.1, 2.3 Hz, 1H), 7.20 (d, J = 5.6 Hz, 1H), 4.36 (q, J = 6.8 Hz, 2H), 3.83 (m, 1H), 1.45 (t, J = 6.8 Hz, 3H), 1.24 (d, J = 6.8 Hz, 6H) | B |
| 49 | 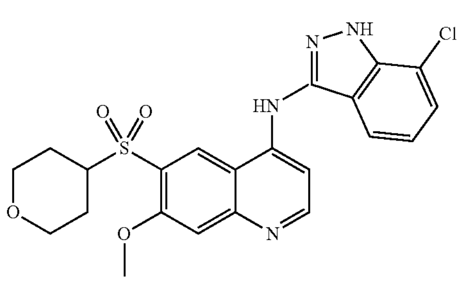 | N-(7-Chloro-1H-indazol-3-yl)-7-methoxy-6-((tetrahydro-2H-pyran-4-yl)sulfonyl)quinolin-4-amine | 473 | $^1$H NMR (400 MHz, DMSO-d$_6$) δ 1.67-1.75 (m, 4H) 3.34-3.42 (m, 2H) 3.79-3.89 (m, 1H) 3.90-3.98 (m, 2H) 4.07 (s, 3H), 7.14 (t, J = 7.83 Hz, 1H) 7.29 (d, J = 5.56 Hz, 1H) 7.51 (s, 1H) 7.53 (s, 1H) 7.83 (d, J = 8.08 Hz, 1H) 8.56 (d, J = 5.31 Hz, 1H) 9.10 (s, 1H) 10.02 (s, 1H) 13.30 (s, 1H) | B |

-continued

The following examples were made in an analogous manner beginning with the appropriate quinoline from the above preparations and/or commercial sources:

| Ex | Structure | Name | MS (M + H)+ | NMR | Step 1 Method |
|---|---|---|---|---|---|
| 50 | 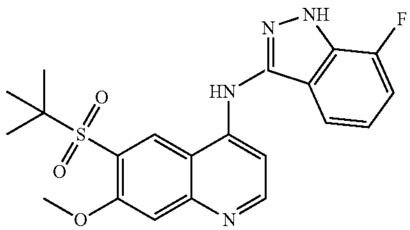 | 6-(tert-butylsulfonyl)-N-(7-fluoro-1H-indazol-3-yl)-7-methoxyquinolin-4-amine | 429 | $^1$H NMR (400 MHz, DMSO-d6) Shift: 13.47 (br. s., 1H), 10.05 (br. s., 1H), 9.07 (s, 1H), 8.43-8.56 (m, 1H), 7.56 (d, J = 8.08 Hz, 1H), 7.46 (br. s., 1H), 7.25 (dd, J = 7.71, 11.49 Hz, 1H), 7.01-7.14 (m, 2H), 3.98 (s, 3H), 1.33 (s, 9H) | A |
| 51 | 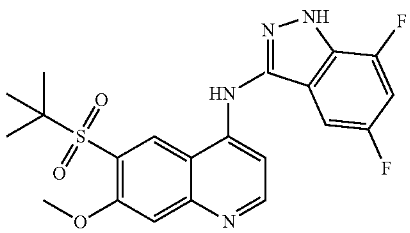 | 6-(tert-butylsulfonyl)-N-(5,7-difluoro-1H-indazol-3-yl)-7-methoxyquinolin-4-amine | 447 | $^1$H NMR (400 MHz, DMSO-d6) Shift: 13.08-13.89 (m, 1H), 9.96 (br. s., 1H), 9.04 (s, 1H), 8.52 (br. s., 1H), 7.47 (br. s., 1H), 7.31-7.43 (m, 2H), 7.07 (d, J = 4.55 Hz, 1H), 3.98 (s, 3H), 1.33 (s, 9H) | A |
| 52 | 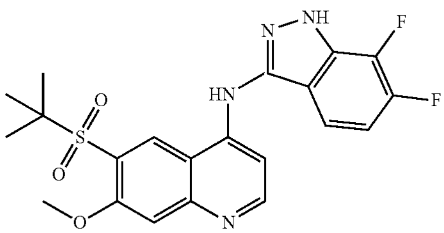 | 6-(tert-butylsulfonyl)-N-(6,7-difluoro-1H-indazol-3-yl)-7-methoxyquinolin-4-amine | 447 | $^1$H NMR (400 MHz, DMSO-d6) Shift: 13.50 (s, 1H), 10.02 (s, 1H), 9.06 (s, 1H), 8.57 (d, J = 5.56 Hz, 1H), 7.64 (dd, J = 3.92, 8.72 Hz, 1H), 7.50 (s, 1H), 7.09-7.32 (m, 2H), 3.99 (s, 3H), 1.33 (s, 9H) | A |
| 53 | 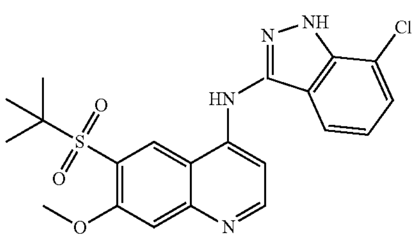 | 6-(tert-butylsulfonyl)-N-(7-chloro-1H-indazol-3-yl)-7-methoxyquinolin-4-amine | 445 | $^1$H NMR (400 MHz, DMSO-d6) Shift: 13.35 (s, 1H), 10.04 (s, 1H), 9.07 (s, 1H), 8.54 (d, J = 5.31 Hz, 1H), 7.75 (d, J = 8.08 Hz, 1H), 7.41-7.58 (m, 2H), 7.07-7.20 (m, 2H), 3.99 (s, 3H), 1.33 (s, 9H) | A |
| 54 | 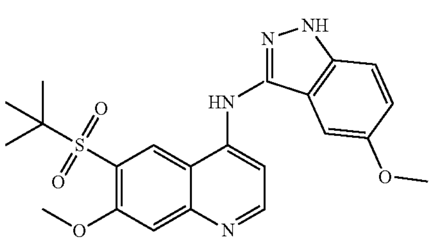 | 6-(tert-butylsulfonyl)-7-methoxy-N-(5-methoxy-1H-indazol-3-yl)quinolin-4-amine | 441 | $^1$H NMR (400 MHz, DMSO-d6) Shift: 12.75 (s, 1H), 9.97 (br. s., 1H), 9.07 (s, 1H), 8.47 (br. s., 1H), 7.42-7.50 (m, 2H), 6.99-7.11 (m, 2H), 6.83 (d, J = 5.56 Hz, 1H), 3.98 (s, 3H), 3.74 (s, 3H), 1.34 (s, 9H) | A |
| 55 | 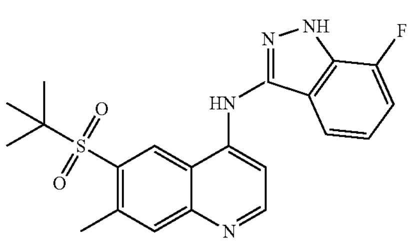 | 6-(tert-butylsulfonyl)-N-(7-fluoro-1H-indazol-3-yl)-7-methylquinolin-4-amine | 413 | $^1$H NMR (400 MHz, DMSO-d6) Shift: 13.43 (s, 1H), 10.08 (s, 1H), 9.13 (s, 1H), 8.59 (d, J = 5.56 Hz, 1H), 7.91 (s, 1H), 7.55 (d, J = 8.08 Hz, 1H), 7.27 (dd, J = 7.58, 11.37 Hz, 1H), 7.17 (d, J = 5.56 Hz, 1H), 7.10 (td, J = 4.55, 7.83 Hz, 1H), 2.79 (s, 3H), 1.34 (s, 9H) | A |

-continued

The following examples were made in an analogous manner beginning with the appropriate quinoline from the above preparations and/or commercial sources:

| Ex | Structure | Name | MS (M + H)+ | NMR | Step 1 Method |
|---|---|---|---|---|---|
| 56 | 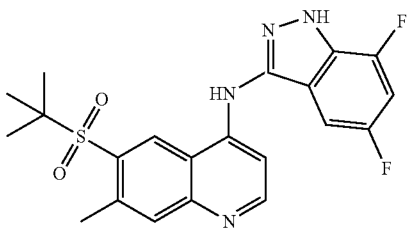 | 6-(tert-butylsulfonyl)-N-(5,7-difluoro-1H-indazol-3-yl)-7-methylquinolin-4-amine | 431 | $^1$H NMR (400 MHz, DMSO-d6) Shift: 13.58 (br. s., 1H), 10.00 (s, 1H), 9.11 (s, 1H), 8.60 (d, J = 5.31 Hz, 1H), 7.91 (s, 1H), 7.40 (d, J = 7.83 Hz, 2H), 7.15 (d, J = 5.05 Hz, 1H), 2.79 (s, 3H), 1.34 (s, 9H) | A |
| 57 | 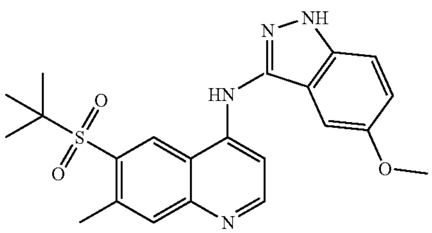 | 6-(tert-butylsulfonyl)-N-(5-methoxy-1H-indazol-3-yl)-7-methylquinolin-4-amine | 425 | $^1$H NMR (400 MHz, DMSO-d6) Shift: 12.78 (s, 1H), 9.96 (s, 1H), 9.13 (s, 1H), 8.53 (d, J = 5.56 Hz, 1H), 7.88 (s, 1H), 7.48 (d, J = 9.09 Hz, 1H), 7.08 (dd, J = 2.40, 8.97 Hz, 1H), 6.99 (d, J = 2.02 Hz, 1H), 6.89 (d, J = 5.56 Hz, 1H), 3.73 (s, 3H), 2.79 (s, 3H), 1.35 (s, 9H) | A |
| 58 | 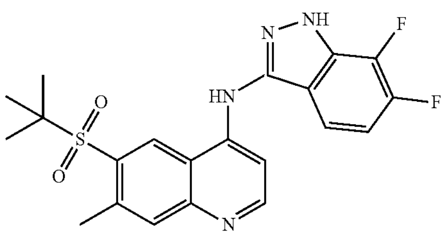 | 6-(tert-butylsulfonyl)-N-(6,7-difluoro-1H-indazol-3-yl)-7-methylquinolin-4-amine | 431 | $^1$H NMR (400 MHz, DMSO-d6) Shift: 9.12 (s, 1H), 8.52 (br. s., 1H), 7.85 (br. s., 1H), 7.58 (dd, J = 3.92, 8.72 Hz, 1H), 7.27 (d, J = 5.56 Hz, 1H), 7.16 (ddd, J = 6.69, 8.91, 10.67 Hz, 1H), 2.78 (s, 3H), 1.33 (s, 9H) | A |
| 59 | 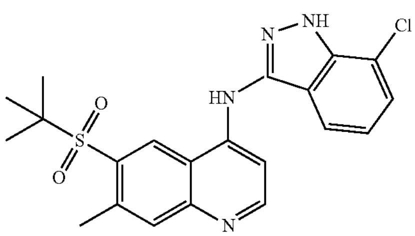 | 6-(tert-butylsulfonyl)-N-(7-chloro-1H-indazol-3-yl)-7-methylquinolin-4-amine | 429 | $^1$H NMR (400 MHz, DMSO-d6) Shift: 9.13 (s, 1H), 8.54 (br. s., 1H), 7.87 (br. s., 1H), 7.70 (d, J = 8.08 Hz, 1H), 7.50 (d, J = 7.07 Hz, 1H), 7.19 (d, J = 5.31 Hz, 1H), 7.12 (t, J = 7.83 Hz, 1H), 2.78 (s, 3H), 1.34 (s, 9H) | A |
| 60 | 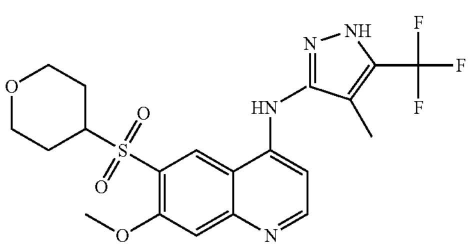 | 7-methoxy-N-(4-methyl-5-(trifluoromethyl)-1H-pyrazol-3-yl)-6-((tetrahydro-2H-pyran-4-yl)sulfonyl)quinolin-4-amine | 471 | $^1$H NMR (400 MHz, DMSO-d6) Shift: 13.70 (br. s., 1H), 8.98 (br. s., 1H), 8.46 (br. s., 1H), 7.39-7.57 (m, 1H), 6.19 (br. s., 1H), 4.07 (s, 3H), 3.90-3.99 (M, 2H), 3.79-3.90 (m, 1H), 3.36 (m, 2H), 1.95 (s, 3H), 1.61-1.77 (m, 4H) | B |
| 61 | 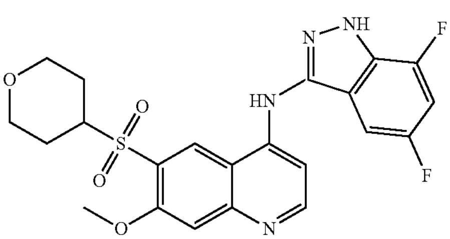 | N-(5,7-difluoro-1H-indazol-3-yl)-7-methoxy-6-((tetrahydro-2H-pyran-4-yl)sulfonyl)quinolin-4-amine | 475 | $^1$H NMR (400 MHz, DMSO-d6) Shift: 13.40 (br. s., 1H), 9.97 (br. s., 1H), 9.07 (s, 1H), 8.52 (br. s., 1H), 7.45-7.55 (m, 2H), 7.33-7.43 (m, 1H), 7.21 (d, J = 5.31 Hz, 1H), 4.07 (s, 3H), 3.89-4.00 (m, 2H), 3.77-3.89 (m, 1H), 3.28-3.43 (m, 2H), 1.65-1.76 (m, 4H) | B |

The following examples were made in an analogous manner beginning with the appropriate quinoline from the above preparations and/or commercial sources:

| Ex | Structure | Name | MS (M + H)+ | NMR | Step 1 Method |
|----|-----------|------|-------------|-----|---------------|
| 62 | 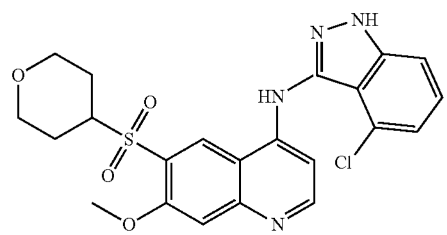 | N-(4-chloro-1H-indazol-3-yl)-7-methoxy-6-((tetrahydro-2H-pyran-4-yl)sulfonyl)quinolin-1-amine | 473 | $^1$H NMR (400 MHz, DMSO-d6) Shift: 13.26 (br. s., 1H), 9.72 (br. s., 1H), 9.01 (s, 1H), 8.42 (br. s., 1H), 7.55 (d, J = 8.34 Hz, 1H), 7.49 (br. s., 1H), 7.38 (t, J = 7.96 Hz, 1H), 7.16 (d, J = 7.33 Hz, 1H), 6.40 (d, J = 5.05 Hz, 1H), 4.06 (s, 3H), 3.89-3.98 (m, 2H), 3.75-3.88 (m, 1H), 3.37 (d, J = 3.03 Hz, 2H), 1.63-1.77 (m, 4H) | B |
| 63 | 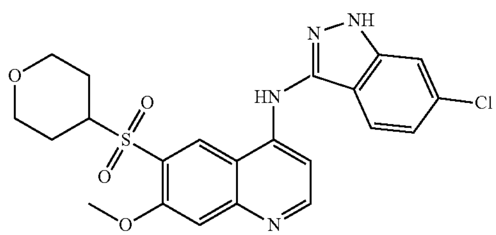 | N-(6-chloro-1H-indazol-3-yl)-7-methoxy-6-((tetrahydro-2H-pyran-4-yl)sulfonyl)quinolin-4-amine | 473 | $^1$H NMR (400 MHz, DMSO-d6) Shift: 12.89 (br. s., 1H), 10.00 (br. s., 1H), 9.09 (s, 1H), 8.55 (br. s., 1H), 7.88 (d, J = 8.84 Hz, 1H), 7.59-7.61 (m, 1H), 7.52 (br. s., 1H), 7.35 (d, J = 4.80 Hz, 1H), 7.15 (dd, J = 1.64, 8.72 Hz, 1H), 4.07 (s, 3H), 3.90-3.97 (m, 2H), 3.79-3.88 (m, 1H), 3.33-3.41 (m, 2H), 1.62-1.75 (m, 4H) | B |
| 64 | 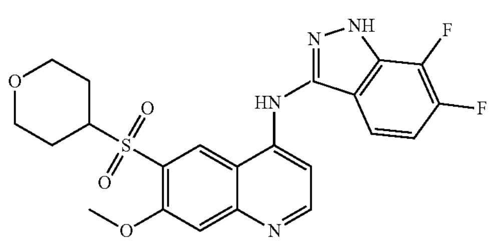 | N-(6,7-difluoro-1H-indazol-3-yl)-7-methoxy-6-((tetrahydro-2H-pyran-4-yl)sulfonyl)quinolin-4-amine | 475 | $^1$H NMR (400 MHz, DMSO-d6) Shift: 12.79-13.69 (m, 1H), 9.92 (br. s., 1H), 9.08 (s, 1H), 8.55 (br. s., 1H), 7.61-7.75 (m, 1H), 7.45-7.55 (m, 1H), 7.28-7.39 (m, 1H), 7.05-7.23 (m, 1H), 4.07 (s, 3H), 3.94 (d, J = 10.86 Hz, 2H), 3.77-3.89 (m, 1H), 3.29-3.40 (m, 2H), 1.62-1.76 (m, 4H) | B |
| 65 | 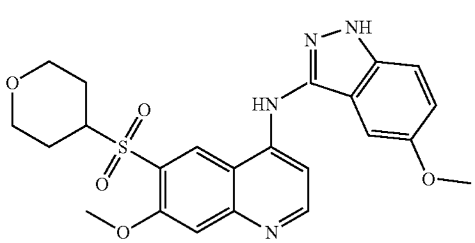 | 7-methoxy-N-(5-methoxy-1H-indazol-3-yl)-6-((tetrahydro-2H-pyran-4-yl)sulfonyl)quinolin-4-amine | 469 | NA | B |

Example 66

N-1,3-benzothiazol-5-yl-6-(methylsulfonyl)-4-quinolinamine

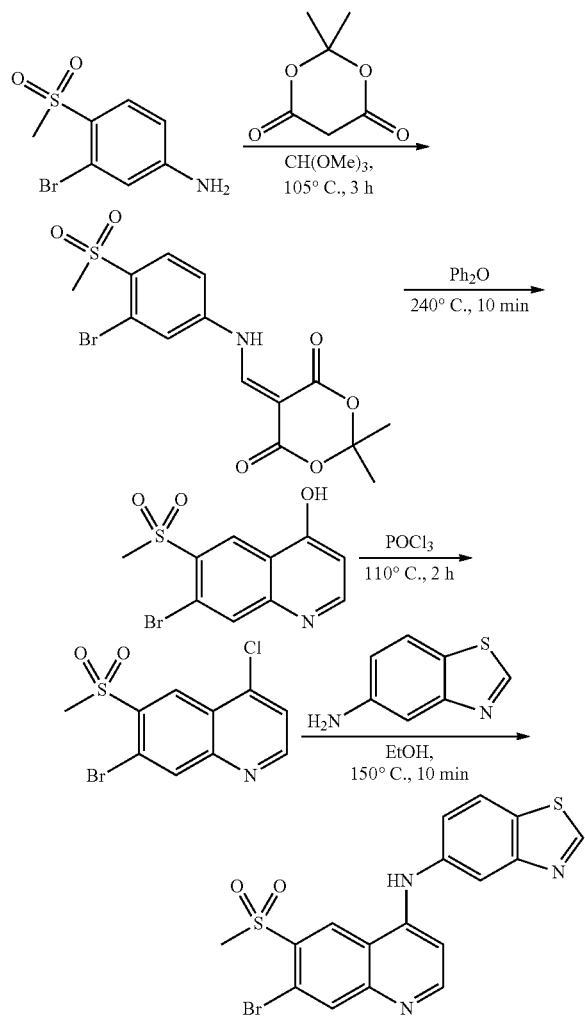

Step 1: 5-({[3-bromo-4-(methylsulfonyl)phenyl]amino}methylidene)-2,2-dimethyl-1,3-dioxane-4,6-dione: A mixture of 2,2-dimethyl-1,3-dioxane-4,6-dione (1.7 g, 12 mmol) and trimethyl orthoformate (24 mL) was heated at reflux for 2 h at which time 3-bromo-4-(methylsulfonyl) aniline (3 g, 12 mmol) was added. The reaction was stirred at 105° C. for 1 hour, cooled to room temperature and filtered. The filter cake was washed with MeOH and dried to provide 5-({[3-bromo-4-(methylsulfonyl)phenyl]amino}methylidene)-2,2-dimethyl-1,3-dioxane-4,6-dione (3.5 g, 8.66 mmol, 72.2% yield). $^1$H NMR (400 MHz, DMSO-$d_6$) δ ppm 11.31 (s, 1 H), 8.68 (s, 1 H), 8.25 (d, J=2.3 Hz, 1 H), 8.05 (d, J=8.8 Hz, 1 H), 7.85 (dd, J=8.8, 2.3 Hz, 1 H), 3.38 (s, 3 H), 1.69 (s, 6 H). MS (m/z) 404, 406 (M+H)

Step 2: 7-bromo-6-(methylsulfonyl)-4-quinolinol: To a 3-neck flask containing diphenylether (17 mL) at 240° C. was added 5-({[3-bromo-4-(methylsulfonyl)phenyl]amino}methylidene)-2,2-dimethyl-1,3-dioxane-4,6-dione (3.5g, 8.6mmol). After the addition was complete, the reaction was allowed to cool to rt, diluted with hexanes and filtered. The crude product was dissolved in DCM, dry loaded onto silica, and purified via column chromatography (Biotage, 0-20% MeOH, EtOAc). The desired fractions were concentrated to yield 7-bromo-6-(methylsulfonyl)-4-quinolinol (800 mg, 2.7 mmol, 31% yield). $^1$H NMR (400 MHz, DMSO-$d_6$) δ ppm 12.09 (br. s., 1 H), 8.73 (s, 1 H), 7.92-8.10(m, 2 H), 6.18 (d, J=7.6 Hz, 1 H), 3.40 (s, 3 H). MS (m/z) 302, 304 (M+H)

Step 3: 7-bromo-4-chloro-6-(methylsulfonyl)quinoline: A mixture of 7-bromo-6-(methylsulfonyl)-4-quinolinol (800 mg, 2.65 mmol) and phosphorus oxychloride (12.300 mL, 132 mmol) was heated at 110° C. After 2 h, the reaction was cooled to rt and concentrated to dryness. The residue was carefully treated with saturated sodium bicarbonate solution until all of the residual $POCl_3$ was neutralized. The mixture was filtered and the precipitate was dried and isolated to provide 7-bromo-4-chloro-6-(methylsulfonyl)quinoline (690 mg, 2.1mmol, 81% yield). $^1$H NMR (400 MHz, DMSO-$d_6$) δ ppm 9.07 (d, J=4.8 Hz, 1 H), 8.91 (s, 1 H), 8.66 (s, 1 H), 8.02 (d, J=4.8 Hz, 1 H), 3.53 (s, 3 H). MS (m/z) 320, 322 (M+H)

Step 4: N-1,3-benzothiazol-5-yl-7-bromo-6-(methylsulfonyl)-4-quinolinamine: 7-bromo-4-chloro-6-(methylsulfonyl)quinoline (500 mg, 1.6 mmol), 1,3-benzothiazol-5-amine (234 mg, 1.56 mmol), and EtOH (3.1 mL) were combined and heated in the microwave at 150° C. for 10 min. The reaction was concentrated to dryness to provide N-1,3-benzothiazol-5-yl-7-bromo-6-(methylsulfonyl)-4-quinolinamine as the HCl salt in quantitative yield. $^1$H NMR (400 MHz, DMSO-$d_6$) δ ppm 11.69 (br. s., 1 H), 9.55 (s, 1 H), 9.48 (s, 1 H), 8.54-8.63 (m, 2 H), 8.40 (d, J=8.6 Hz, 1 H), 8.21 (d, J=2.0 Hz, 1 H), 7.61 (dd, J=8.6, 2.0 Hz, 1 H), 6.97 (d, J=6.8 Hz, 1 H), 3.54 (s, 3 H). MS (m/z) 434, 436 (M+H)

The following examples were synthesized in the same manner as the above example using the appropriate quinoline from the above preparations and/or commercially available materials.

| Ex. | Structure | Name | MS (M + H)$^+$ | NMR |
|---|---|---|---|---|
| 67 | (structure) | 7-bromo-N-(4,5-dimethyl-1H-pyrazol-3-yl)-6-((tetrahydro-2H-pyran-4-yl)sulfonyl)quinolin-4-amine, 2 Trifluoroacetic acid salt | 465 | $^1$H NMR (400 MHz, DMSO-$d_6$) δ ppm 12.73 (br. s., 1H), 11.43 (br. s., 1H), 9.39 (br. s., 1H), 8.62 (d, J = 7.1 Hz, 1H), 8.40 (s, 1H), 6.85 (d, J = 7.1 Hz, 1H), 3.82-4.05 (m, 3H), 3.23-3.45 (m, 2H), 2.25 (s, 3H), 1.86 (s, 3H), 1.67-1.81 (m, 4H) |

| Ex. | Structure | Name | MS (M + H)+ | NMR |
|---|---|---|---|---|
| 68 | 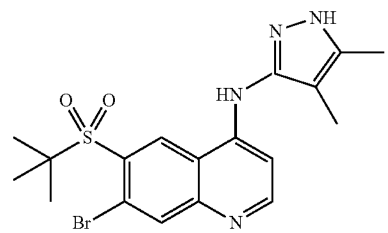 | 7-bromo-6-(tert-butylsulfonyl)-N-(4,5-dimethyl-1H-pyrazol-3-yl)quinolin-4-amine, (2 Trifluoroacetic acid salt) | 437 | $^1$H NMR (400 MHz, DMSO-d$_6$) δ ppm 12.58-12.89 (m, 1H), 11.50 (br. s., 1H), 9.40 (br. s., 1H), 8.61 (d, J = 7.1 Hz, 1H), 8.37 (s, 1H), 6.80 (d, J = 7.1 Hz, 1H), 2.25 (s, 3H), 1.85 (s, 3H), 1.40 (s, 9H) |
| 69 | 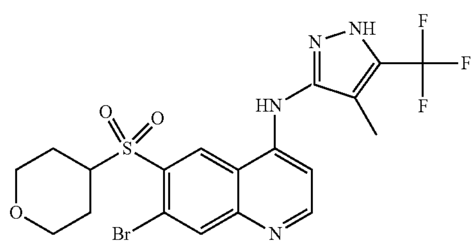 | 7-bromo-N-(4-methyl-5-(trifluoromethyl)-1H-pyrazol-3-yl)-6-((tetrahydro-2H-pyran-4-yl)sulfonyl)quinolin-4-amine | 519, 521 | $^1$H NMR (400 MHz, DMSO-d$_6$) δ ppm 13.75 (br. s., 1H), 9.66-10.04 (m, 1H), 8.99-9.37 (m, 1H), 8.49-8.85 (m, 1H), 8.27-8.45 (m, 1H), 6.36 (br. s., 1H), 3.84-4.13 (m, 4H), 3.22-3.52 (m, 1H), 1.96 (s, 3H), 1.74 (d, J = 2.78 Hz, 1H) |
| 70 | 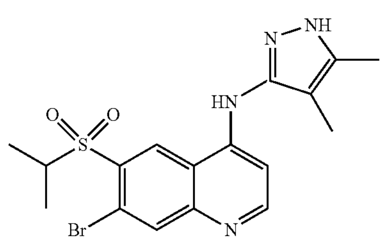 | 7-bromo-N-(4,5-dimethyl-1H-pyrazol-3-yl)-6-(isopropylsulfonyl)quinolin-4-amine | 423 | $^1$H NMR (DMSO-d6) Shift: 12.25 (br. s., 1H), 9.53 (br. s., 1H), 9.15 (br. s., 1H), 8.41-8.62 (m, 1H), 8.15-8.37 (m, 1H), 6.50-6.77 (m, 1H), 3.81-3.97 (m, 1H), 2.18 (br. s., 3H), 1.78 (br. s., 3H), 1.25 (d, J = 6.8 Hz, 6H) |
| 71 | 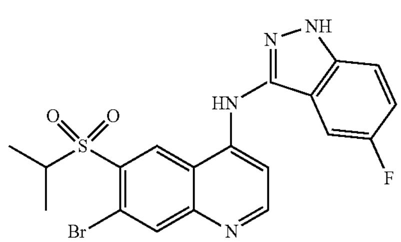 | 7-bromo-N-(5-fluoro-1H-indazol-3-yl)-6-(isopropylsulfonyl)quinolin-4-amine | 463 | $^1$H NMR (DMSO-d6) Shift: 9.29 (s, 1H), 8.45 (s, 1H), 8.20 (br. s., 1H), 7.43-7.61 (m, 2H), 7.19-7.35 (m, 2H), 3.86-4.00 (m, 1H), 1.27 (d, J = 6.8 Hz, 6H) |
| 72 | 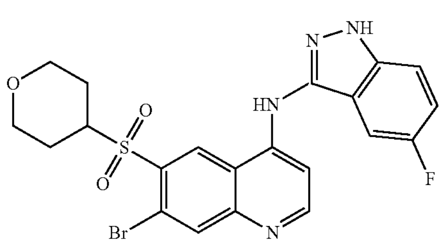 | 7-bromo-N-(5-fluoro-1H-indazol-3-yl)-6-((tetrahydro-2H-pyran-4-yl)sulfonyl)quinolin-4-amine | 505 | NA |

Example 73

N-1,3-benzothiazol-5-yl-6-[(1,1-dimethylethyl)sulfonyl]-7-(methyloxy)-4-quinolinamine

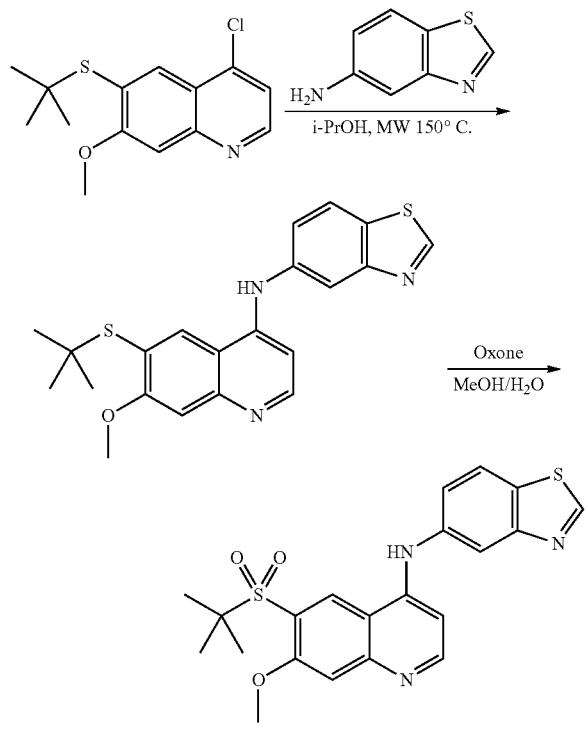

Step 1. N-1,3-benzothiazol-5-yl-6-[(1,1-dimethylethyl)thio]-7-(methyloxy)-4-quinolinamine: 4-chloro-6-[(1,1-dimethylethyl)thio]-7-(methyloxy)quinoline (0.20 g, 0.66 mmol) and 1,3-benzothiazol-5-amine (0.10 g, 0.66 mmol) in isopropanol (2 mL) were irradiated by microwave at 150° C. for 15 mins. The reaction mixture was concentrated, purified via flash chromatography (0-50% EtOAc/Hexane, 0-5% MeOH/DCM) to yield N-1,3-benzothiazol-5-yl-6-[(1,1-dimethylethyl)thio]-7-(methyloxy)-4-quinolinamine (0.26 g, 0.67 mmol, 94% yield). $^1$H NMR (400 MHz, DMSO-d) δ ppm 1.28 (s, 9H), 3.93 (s, 3H), 6.90 (d, J=5.3 Hz, 1H), 7.32 (s, 1H), 7.54 (dd, J=8.6 Hz, 2 Hz, 1H), 8.02 (d, J=2 Hz, 1H), 8.18 (d, J=8.6 Hz, 1H), 8.42 (d, J=5.3 Hz, 1H), 8.60 (s, 1H), 9.27 (s, 1H), 9.42 (s, 1H). MS (m/z) 396 (M+H$^+$).

Step 2. N-1,3-benzothiazol-5-yl-6-[(1,1-dimethylethyl)sulfonyl]-7-(methyloxy)-4-quinolinamine: N-1,3-benzothiazol-5-yl-6-[(1,1-dimethylethyl)thio]-7-(methyloxy)-4-quinolinamine (0.14 g, 0.34 mmol) and oxone (0.32 g, 0.52 mmol) in MeOH (2 mL) and water (2 mL) were stirred at room temperature. The reaction mixture was filtered, and the cake was washed with MeOH. The filtrate was concentrated, dissolved in dimethyl sulfoxide, purified via reverse phase HPLC (Waters SunFire Prep C18 OBD 5 μm, 30×100 mm column, 20-30% acetonitrile/water 0.1% TFA, 40 mL/min, 10 min) to yield the trifluoroacetic acid salt. The salt was basified with saturated sodium carbonate and extracted with EtOAc. The EtOAc layer was dried over sodium sulfate, filtered, concentrated and vacuum dried to yield N-1,3-benzothiazol-5-yl-6-[(1,1-dimethylethyl)sulfonyl]-7-(methyloxy)-4-quinolinamine (0.040 g, 0.091 mmol, 26.6% yield). $^1$H NMR (400 MHz, DMSO-d) δ ppm 1.32 (s, 9H), 3.98 (s, 3H), 6.90 (d, J=5.3 Hz, 1H), 7.47 (s, 1H), 7.54 (dd, J=8.6 Hz, 2 Hz, 1H), 8.03 (d, J=2 Hz, 1H), 8.20 (d, J=8.6 Hz, 1H), 8.50 (d, J=5.6 Hz, 1H), 8.94 (s, 1H), 9.43 (s, 1H), 9.69 (s, 1H). MS (m/z) 428 (M+H$^+$).

Example 74

2-((6-(tert-butylsulfonyl)-4-((4,5-dimethyl-1H-pyrazol-3-yl)amino)quinolin-7-yl)oxy)ethanol

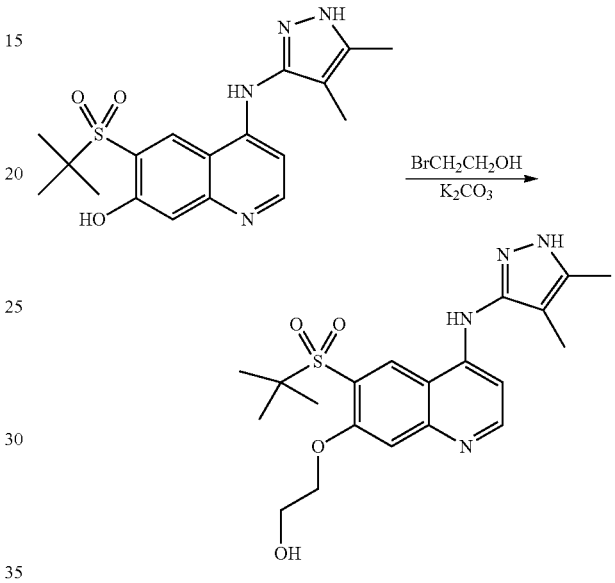

A suspension of 6-(tert-butylsulfonyl)-4-((4,5-dimethyl-1H-pyrazol-3-yl)amino)quinolin-7-ol (50.0 mg, 0.134 mmol) and potassium carbonate (55.4 mg, 0.401mmol) in DMF (0.65 mL) was stirred 2 min before 2-bromoethanol (47.3 μA, 0.668 mmol) was added. The reaction mixture was stirred at room temperature for 3 d. The crude reaction mixture was filtered and the residue was purified via Gilson reverse phase chromatography (6% to 75% 0.1% TFA in MeCN in 0.1% TFA in water; Sum 30×150 mm Waters SunFire column). The collected fractions were evaporated to dryness to provide 2-(6-(tert-butylsulfonyl)-4-((4,5-dimethyl-1H-pyrazol-3-yl)amino)quinolin-7-yl)oxy)ethanol (15.6 mg, 22% yield) as a colorless oil. $^1$H NMR (METHANOL-d$_4$) δ ppm 9.23 (br. s., 1H), 8.38 (d, J=7.3 Hz, 1H), 7.50 (s, 1H), 6.76 (d, J=7.3 Hz, 1H), 4.39 (t, J=4.5 Hz, 2H), 4.04 (dd, J=5.1, 4.3 Hz, 2H), 2.33 (s, 3H), 1.96 (s, 3H), 1.47 (s, 9H). MS (m/z) 418, 419 (M+H$^+$).

Example 75

6-(tert-butylsulfonyl)-7-(difluoromethoxy)-N-(4,5-dimethyl-1H-pyrazol-3-yl) quinolin-4-amine

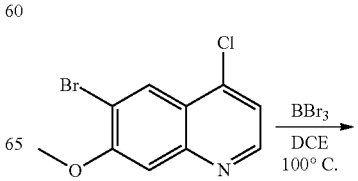

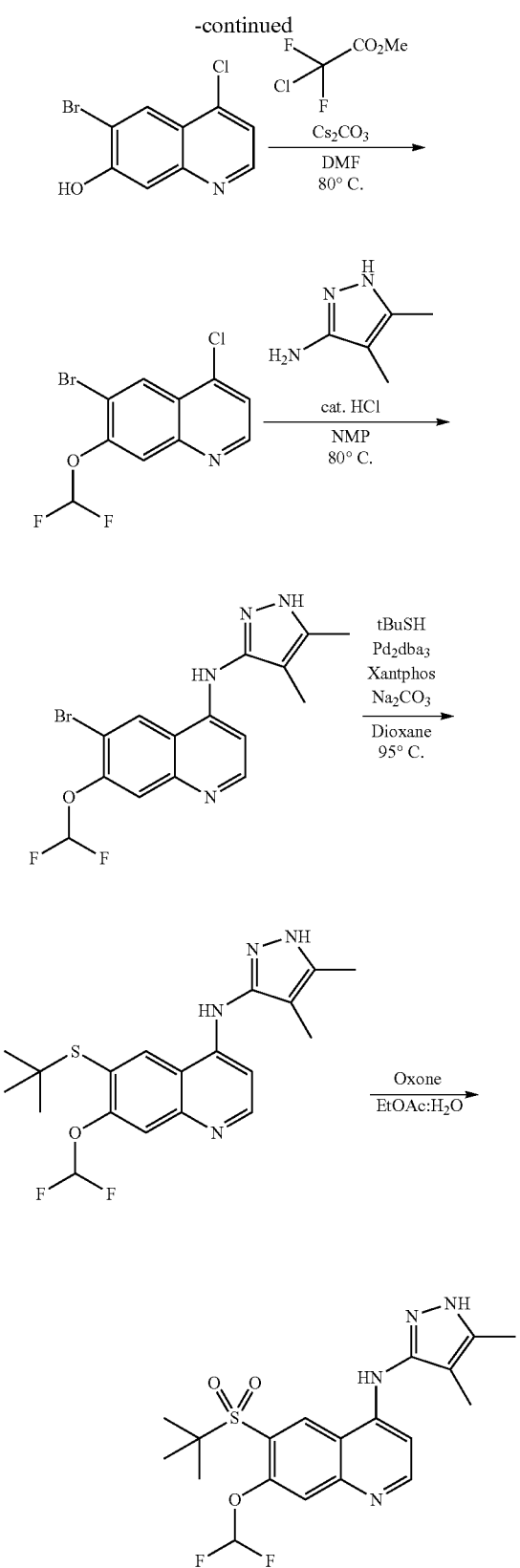

Step 1. 6-bromo-4-chloroquinolin-7-ol: 6-Bromo-4-chloro-7-methoxyquinoline (5 g, 18.4 mmol) was taken up in DCE (15 mL) before BBr$_3$ (5.20 mL, 55.0 mmol) was added dropwise. Reaction was then heated to 100° C. via microwave for 2 hours. The reaction was carefully pipetted into stirred MeOH. The suspension was then concentrated. It was then taken up in 50 mL of MeOH and filtered. The cake was rinsed with MeOH once and dried under vacuum to afford the title compound (4.82 g, 99%). MS (m/z): 258, 260 (M+H$^+$).

Step 2. 6-bromo-4-chloro-7-(difluoromethoxy)quinoline: To a DMF (15 mL) solution of 6-bromo-4-chloroquinolin-7-ol (3 g, 11.6 mmol) was added cesium carbonate (11.34 g, 34.8 mmol). After 30 min, methyl 2-chloro-2,2-difluoroacetate (2.5 mL, 23.2 mmol) was added and the reaction was heated to 80° C. overnight. It was cooled to rt and concentrated. The residue was suspended in DCM and filtered. The filtrate was concentrated. The resulting crude was purified by flash chromatography to afford the product as a light brown solid (750 mg, 20%). MS (m/z): 308, 310 (M+H$^+$).

Step 3. 6-bromo-7-(difluoromethoxy)-N-(4,5-dimethyl-1H-pyrazol-3-yl)quinolin-4-amine: 6-Bromo-4-chloro-7-(difluoromethoxy)quinoline (750 mg, 2.4 mmol) and 4,5-dimethyl-1H-pyrazol-3-amine (270 mg, 2.4 mmol) were taken up in NMP (5 mL) before 2drops of conc HCl was added. The reaction was heated to 80° C. overnight before being concentrated. The residue was then suspended in 5 mL of DCM, sonicated, and filtered. The solid was washed with DCM and the desired product was obtained as a yellow solid (820 mg, 84%). MS (m/z): 383, 385 (M+H$^+$).

Step 4. 6-(tert-butylthio)-7-(difluoromethoxy)-N-(4,5-dimethyl-1H-pyrazol-3-yl)quinolin-4-amine: To a vial was added 6-bromo-7-(difluoromethoxy)-N-(4,5-dimethyl-1H-pyrazol-3-yl)quinolin-4-amine (410 mg, 1.07 mmol), Pd$_2$dba$_3$ (98 mg, 0.11 mmol), Xantphos (61.9 mg, 0.11 mmol), and sodium carbonate (284 mg, 2.67 mmol) before evacuating and backfilling the vial with nitrogen. 1,4-Dioxane (5000 µl) was then added followed by t-butylthiol (133 µl, 1.18 mmol). The reaction was then heated to 95° C. overnight. Additional heating in the microwave for 30 min at 120° C. allowed the reaction to go to completion. The reaction mixture was purified by flash chromatography to afford the product as yellow-brown solid (430 mg, 97%). MS (m/z): 393 (M+H$^+$).

Step 5. 6-(tert-butylsulfonyl)-7-(difluoromethoxy)-N-(4,5-dimethyl-1H-pyrazol-3-yl)quinolin-4-amine: 6-(tert-Butylthio)-7-(difluoromethoxy)-N-(4,5-dimethyl-1H-pyrazol-3-yl)quinolin-4-amine (430 mg, 1.10 mmol) was taken up in EtOAc (6 mL) and water (6 mL) before oxone (775 mg, 1.26 mmol) was added and the reaction was stirred at rt over the weekend. The reaction was concentrated. The residue was then dissolved in DMSO:MeOH (5 mL), filtered through a syringe filter, and purified by reverse phase HPLC. Purified material was dissolved in MeOH and free based using a MP-carbonate resin. After allowing the mixture to sit on the resin overnight, the resin was filtered off, and rinsed with MeOH. The filtrate was then concentrated to afford the title product as a yellow solid (164 mg, 32%). $^1$H NMR (DMSO-d$_6$) δ 12.51 (br. s., 1H), 10.44 (br. s., 1H), 9.21 (s, 1H), 8.55 (d, J=6.3 Hz, 1H), 7.72 (s, 1H), 7.49 (t, J=73 Hz, 1H), 6.64 (d, J=6.1 Hz, 1H), 2.23 (s, 3H), 1.82 (s, 3H), 1.36 (s, 9H); MS (m/z): 425 (M+H$^+$).

The following examples were synthesized in the same manner as the above example.

| Ex. | Structure | Name | MS (M + H)+ | NMR |
|---|---|---|---|---|
| 76 | 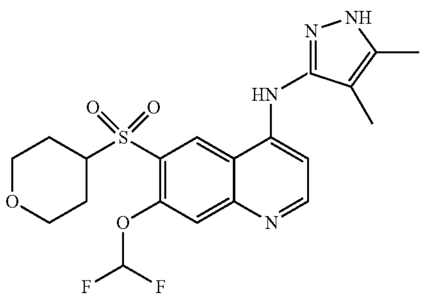 | 7-(difluoromethoxy)-N-(4,5-dimethyl-1H-pyrazol-3-yl)-6-((tetrahydro-2H-pyran-4-yl)sulfonyl)quinolin-4-amine | 453 | ¹H NMR (DMSO-d6) Shift: 12.30 (br. s., 1H), 9.53 (br. s., 1H), 9.10 (s, 1H), 8.50 (d, J = 5.6 Hz, 1H), 7.68 (s, 1H), 7.56 (t, J = 72.8 Hz, 1H), 6.59 (d, J = 4.8 Hz, 1H), 3.90-4.00 (m, 2H), 3.62-3.76 (m, 1H), 3.28-3.40 (m, 2H), 2.21 (s, 3H), 1.80 (s, 3H), 1.66-1.78 (m, 4H) |

Example 77

2-((4-(benzo[d]thiazol-5-ylamino)-6-(tert-butylsulfonyl)quinolin-7-yl)oxy)ethanol

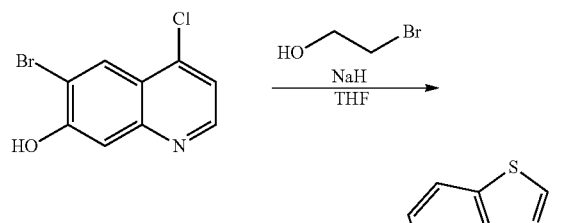

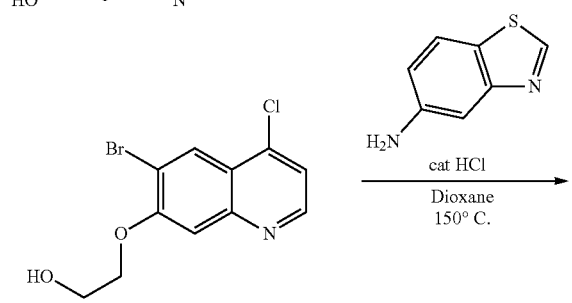

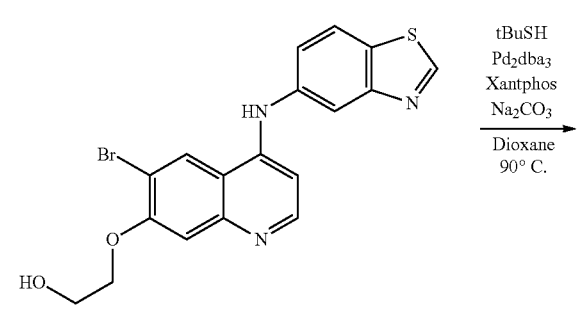

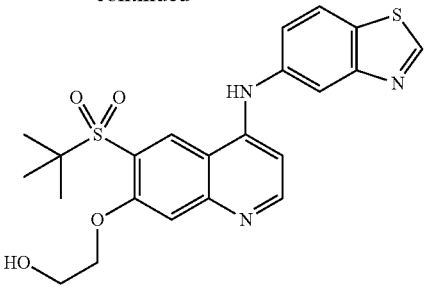

Step 1. 2-((6-bromo-4-chloroquinolin-7-yl)oxy)ethanol: To a THF (20 mL) solution of 6-bromo-4-chloroquinolin-7-ol (1000 mg, 3.87 mmol) was added NaH (232 mg, 5.80mmol, 60% in mineral oil) at rt. The mixture was stirred for 30 min before 2-bromoethanol (0.33 mL, 4.64 mmol) was added and the reaction was heated to 80° C. overnight. It was then cooled to rt and concentrated. The crude was purified by flash chromatography to afford the product as a yellow solid (970 mg, 83%). MS (m/z): 302, 304 (M+H+).

Step 2. 2-((4-(benzo[d]thiazol-5-ylamino)-6-bromoquinolin-7-yl)oxy)ethanol: 2-((6-bromo-4-chloroquinolin-7-yl)oxy)ethanol (0.97 g, 3.21 mmol), benzo[d]thiazol-5-amine (0.58 g, 3.85 mmol), 1,4-dioxane (5 mL), and 2 drops of conc. HCl were combined and heated to 150° C. for 30 min via microwave. It was concentrated onto silica gel and purified by flash chromatography. The title compound was obtained as a yellow solid (560 mg, 40%). MS (m/z): 416, 418 (M+H+).

Step 3. 2-((4-(benzo[d]thiazol-5-ylamino)-6-(tert-butylthio)quinolin-7-yl)oxy)ethanol: To a vial was added 2-((4-(benzo[d]thiazol-5-ylamino)-6-bromoquinolin-7-yl)oxy)ethanol (100 mg, 0.24 mmol), Pd₂ dba₃ (22 mg, 0.02 mmol), Xantphos (14 mg, 0.02mmol), and sodium carbonate (64 mg, 0.60 mmol). The vial was evacuated and backfilled with nitrogen three times before 1,4-dioxane (1 mL) and then tert-butylthiol (30 μl, 0.26mmol) were added. The reaction was heated to 90° C. overnight. It was cooled to rt and quenched with 2 mL of sat aq NH₄Cl. The mixture was extracted using EtOAc (3×5 mL) and the combined organics were dried over sodium sulfate, filtered, and concentrated. The crude was then purified by flash chromatography which afforded the product as a yellow film (90 mg, 84). MS (m/z): 426.1 (M+H+).

Step 4. 2-((4-(benzo[d]thiazol-5-ylamino)-6-(tert-butylsulfonyl)quinolin-7-yl)oxy)ethanol: 2-((4-(benzo[d]thiazol-5-ylamino)-6-(tert-butylthio)quinolin-7-yl)oxy)ethanol (90 mg, 0.21 mmol) was dissolved in MeOH (3 mL) before water (3 mL) and then oxone (130 mg, 0.21 mmol) were added. The reaction mixture was stirred at rt overnight. It was concentrated and the residue was taken up in 2 mL of 1:1 DMSO:MeOH, filtered through a syringe filter, and purified by reverse phase HPLC to afford the title compound (42 mg, 43%). $^1$H NMR (DMSO-$d_6$) δ 9.83 (br. s., 1H), 9.45 (s, 1H), 8.97 (s, 1H), 8.49 (d, J=5.5 Hz, 1H), 8.22 (d, J=8.8 Hz, 1H), 8.05 (d, J=1.8 Hz, 1H), 7.55 (dd, J=8.7, 1.6 Hz, 1H), 7.48 (s, 1H), 6.89 (d, J=5.5 Hz, 1H), 4.80 (br. s., 1H), 4.25 (t, J=5.0 Hz, 2H), 3.82 (d, J=4.5 Hz, 2H), 1.35 (s, 9H); MS (m/z): 458 (M+H$^+$).

Example 78

(3-((6-(tert-Butylsulfonyl)-7-methoxyquinolin-4-yl)amino)-4-methyl-1H-pyrazol-5-yl)methanol

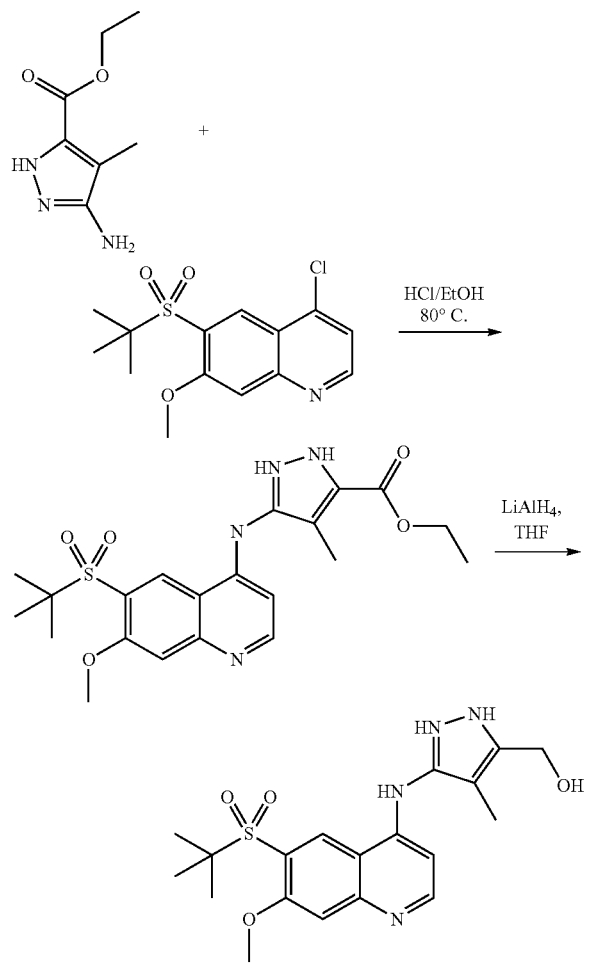

Step 1: Ethyl 3-{[6-[(1,1-dimethylethyl)sulfonyl]-7-(methyloxy)-4-quinolinyl]amino}-4-methyl-1H-pyrazole-5-carboxylate, Hydrochloride: 6-(tert-Butylsulfonyl)-4-chloro-7-methoxyquinoline (420 mg, 1.338 mmol) and ethyl 3-amino-4-methyl-1H-pyrazole-5-carboxylate (249 mg, 1.472 mmol) were dissolved in EtOH with two drops of HCl (4M in dioxane) added, and the reaction mixture was heated at 80° C. for 5 h followed by then cooling to room temperature. The precipitate was filtered, washed with EtOH, and air dried to give ethyl 3-((6-(tert-butylsulfonyl)-7-methoxyquinolin-4-yl)amino)-4-methyl-1H-pyrazole-5-carboxylate, Hydrochloride (586 mg, 1.213 mmol, 91% yield) as a yellow solid. $^1$H NMR (DMSO-$d_6$) δ: 1.31-1.38 (m, 12 H) 2.13 (s, 3 H) 4.04 (s, 3 H) 4.37 (q, J=7.07 Hz, 2 H) 6.62 (d, J=6.82 Hz, 1 H) 7.71 (s, 1 H) 8.55 (d, J=7.07 Hz, 1 H) 9.24 (br. s., 1 H) 11.33 (br. s., 1 H) 14.10 (br. s., 1 H) 14.76 (br. s., 1 H)); MS (m/z) 447 (M+H$^+$).

Step 2: (3-((6-(tert-Butylsulfonyl)-7-methoxyquinolin-4-yl)amino)-4-methyl-1H-pyrazol-5-yl)methanol: Ethyl 3-((6-(tert-butylsulfonyl)-7-methoxyquinolin-4-yl)amino)-4-methyl-1H-pyrazole-5-carboxylate, Hydrochloride (100 mg, 0.207 mmol) was suspended in THF (2 mL) and lithium aluminum hydride (1.0 M in THF, 0.518 mL, 0.518 mmol) was added dropwise. The reaction mixture was stirred at room temperature for 4 h before quenching with water (0.1 mL), NaOH (2N, 0.1 mL), and NH$_4$Cl (sat'd, 0.4 mL) sequentially. The mixture was extracted with DCM (2×50 mL). The combined organics were dried over MgSO$_4$, filtered, and concentrated before and purifying on an ISCO (silica gel column, 10 g) using 10-20% of (10% ammonium hydroxide in IPA) in EtOAc to afford the desired product (3-((6-(tert-butylsulfonyl)-7-methoxyquinolin-4-yl)amino)-4-methyl-1H-pyrazol-5-yl)methanol as off-white solid (16 mg, 0.040 mmol, 19.11% yield). $^1$H NMR (400 MHz, DMSO-$d_6$) δ 1.32 (s, 9 H) 1.84 (s, 3 H) 3.96 (s, 3 H) 4.48 (d, J=5.31 Hz, 2 H) 5.21 (t, J=5.56Hz, 1 H) 6.41 (d, J=5.56 Hz, 1 H) 7.41 (s, 1 H) 8.41 (d, J=5.56 Hz, 1 H) 8.95 (s, 1 H) 9.36(br. s., 1 H) 12.48 (br. s., 1 H); MS (m/z) 405 (M+H$^+$).

Example 79

N-(4,5-dimethyl-1H-pyrazol-3-yl)-7-methyl-6-((4-methyltetrahydro-2H-pyran-4-yl)sulfonyl)quinolin-4-amine

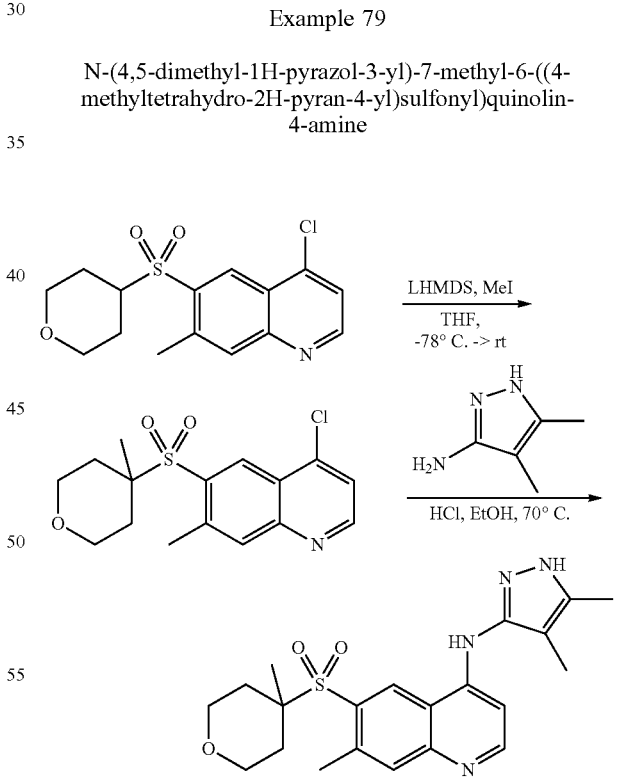

Step 1: 4-chloro-7-methyl-6-((tetrahydro-2H-pyran-4-yl)sulfonyl)quinoline: To an oven dried RBF was added 4-chloro-7-methyl-6-((tetrahydro-2H-pyran-4-yl)sulfonyl)quinoline (450 mg, 1.381 mmol) and THF (18 mL). The solution was cooled to −78° C. and LHMDS (4.14 mL, 4.14 mmol) was added. After 15 min, methyl iodide (0.345mL, 5.52 mmol) was added and the reaction was allowed to warm to rt over 2 h. Saturated ammonium chloride was added and the reaction was extracted with DCM (2×), washed with brine (1×) and dry-loaded onto silica gel. The crude product was purified via column chromatography (Biotage SP-1 0-15% MeOH/EtOAc, 50 g column) to afford 4-chloro-7-methyl-6-((4-methyltetrahydro-2H-pyran-4-yl)sulfonyl)quinoline (125 mg, 0.305 mmol, 22.10% yield) which was only 83% pure, but carried on as is to the next step. $^1$H NMR (400MHz, DMSO-$d_6$) δ ppm 9.02 (d, J=4.5 Hz, 1 H), 8.66 (s, 1 H), 8.20 (s, 1 H), 7.91 (d, J=4.8Hz, 1 H), 3.72-3.86 (m, 2 H), 3.45 (td, J=11.9, 1.8 Hz, 2 H), 2.77-2.91 (m, 3 H), 1.90-2.11 (m, 2 H), 1.51 (d, J=13.6 Hz, 2 H), 1.43 (s, 3 H). MS (m/z) 340.

Step 2: N-(4,5-dimethyl-1H-pyrazol-3-yl)-7-methyl-6-((4-methyltetrahydro-2H-pyran-4-yl)sulfonyl)quinolin-4-amine: A mixture of 4-chloro-7-methyl-6-((4-methyltetrahydro-2H-pyran-4-yl)sulfonyl)quinoline (50 mg, 0.122 mmol) and 4,5-dimethyl-1H-pyrazol-3-amine (16.29 mg, 0.147 mmol) in EtOH (1221 µl) was treated with 1 drop of conc. HCl (0.122 mmol) and heated to 70° C. for 3 d. The reaction was diluted with water and DMSO, filtered, and the filtrate was concentrated and purified via reverse phase HPLC (10-60% acetonitrile/water w/0.1% TFA). The product-containing fractions were concentrated to dryness and the resulting oil was treated with EtOAc/hexane and concentrated to dryness to afford N-(4,5-dimethyl-1H-pyrazol-3-yl)-7-methyl-6-((4-methyltetrahydro-2H-pyran-4-yl)sulfonyl)quinolin-4-amine, 2 Trifluoroacetic acid salt (10mg, 0.016 mmol, 12.74% yield) as a solid. NMR: $^1$H NMR (400 MHz, DMSO-$d_6$) δ ppm 14.25 (br. s., 1 H), 12.71 (br. s., 1 H), 11.28 (br. s., 1 H), 9.23 (br. s., 1 H), 8.56 (d, J=7.1 Hz, 1 H), 7.91 (s, 1 H), 6.74 (d, J=7.1 Hz, 1 H), 3.84 (dd, J=11.6, 4.3 Hz, 2 H), 3.44-3.53 (m, 2 H), 2.85 (s, 3 H), 2.25 (s, 3 H), 2.01-2.18 (m, 2 H), 1.85 (s, 3 H), 1.36-1.56 (m, 5 H). MS (m/z) 415.

The following examples were synthesized in the same manner as the above example.

| Ex. | Structure | Name | MS (M + H)+ | NMR |
| --- | --- | --- | --- | --- |
| 80 | 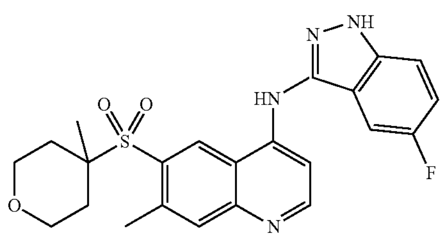 | N-(5-fluoro-1H-indazol-3-yl)-7-methyl-6-((4-methyltetrahydro-2H-pyran-4-yl)sulfonyl)quinolin-4-amine | 455 | $^1$H NMR (400 MHz, DMSO-d6) Shift: 13.00 (s, 1H), 9.97 (s, 1H), 9.09 (s, 1H), 8.58 (d, J = 5.6 Hz, 1H), 7.91 (s, 1H), 7.60 (dd, J = 9.2, 4.2 Hz, 1H), 7.48 (dd, J = 9.1, 2.0 Hz, 1H), 7.32 (td, J = 9.1, 2.3 Hz, 1H), 7.11 (d, J = 5.3 Hz, 1H), 3.84 (dd, J = 11.5, 4.2 Hz, 2H), 3.39-3.53 (m, 2H), 2.80 (s, 3H), 2.12 (br. s., 2H), 1.38-1.55 (m, 5H) |
| 81 | 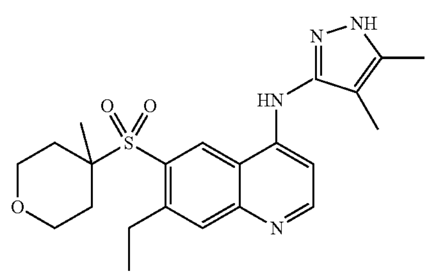 | N-(4,5-dimethyl-1H-pyrazol-3-yl)-7-ethyl-6-((4-methyltetrahydro-2H-pyran-4-yl)sulfonyl)quinolin-4-amine | 429 | $^1$H NMR (400 MHz, DMSO-d6) Shift: 12.30 (s, 1H), 9.41 (s, 1H), 8.96 (s, 1H), 8.47 (d, J = 5.3 Hz, 1H), 7.86 (s, 1H), 6.50 (d, J = 5.6 Hz, 1H), 3.82 (dd, J = 11.7, 4.4 Hz, 2H), 3.44 (t, J = 11.4 Hz, 2H), 3.15 (q, J = 7.3 Hz, 2H), 2.21 (s, 3H), 2.08 (td, J = 12.7, 4.9 Hz, 2H), 1.78 (s, 3H), 1.38-1.50 (m, 5H), 1.30 (t, J = 7.3 Hz, 3H) |
| 82 | 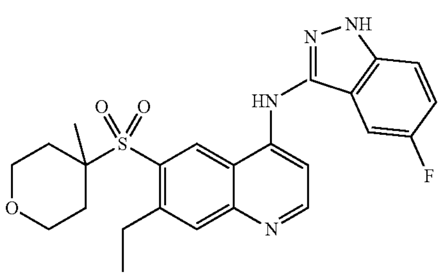 | 7-ethyl-N-(5-fluoro-1H-indazol-3-yl)-6-((4-methyltetrahydro-2H-pyran-4-yl)sulfonyl)quinolin-4-amine | 469 | $^1$H NMR (400 MHz, DMSO-d6) Shift: 13.00 (s, 1H), 9.98 (s, 1H), 9.09 (s, 1H), 8.58 (d, J = 5.6 Hz, 1H), 7.94 (s, 1H), 7.60 (dd, J = 9.1, 4.0 Hz, 1H), 7.48 (d, J = 9.1 Hz, 1H), 7.28-7.37 (m, 1H), 7.11 (d, J = 5.3 Hz, 1H), 3.83 (d, J = 12.1 Hz, 2H), 3.39-3.51 (m, 2H), 3.19 (d, J = 7.3 Hz, 2H), 2.08 (br. s., 2H), 1.43 (s, 5H), 1.32 (t, J = 7.3 Hz, 3H) |
| 83 | 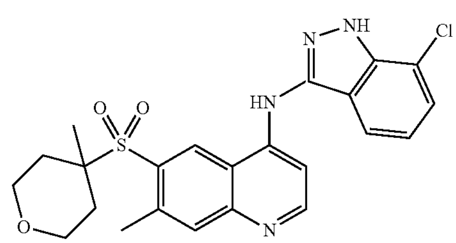 | N-(7-chloro-1H-indazol-3-yl)-7-methyl-6-((4-methyltetrahydro-2H-pyran-4-yl)sulfonyl)quinolin-4-amine | 471 | $^1$H NMR (400 MHz, DMSO-d6) Shift: 13.40 (br. s., 1H), 10.13 (br. s., 1H), 9.10 (s, 1H), 8.60 (br. s., 1H), 7.92 (br. s., 1H), 7.73 (s, 1H), 7.52 (s, 1H), 7.08-7.26 (m, 2H), 3.77-3.91 (m, 2H), 3.40-3.53 (m, 2H), 2.80 (s, 3H), 2.08-2.17 (m, 2H), 1.39-1.53 (m, 5H) |

Pharmaceutical Compositions

Example A

Tablets are prepared using conventional methods and are formulated as follows:

| Ingredient | Amount per tablet |
|---|---|
| Compound of Example 1 | 5 mg |
| Microcrystalline cellulose | 100 mg |
| Lactose | 100 mg |
| Sodium starch glycollate | 30 mg |
| Magnesium stearate | 2 mg |
| Total | 237 mg |

Example B

Capsules are prepared using conventional methods and are formulated as follows:

| Ingredient | Amount per tablet |
|---|---|
| Compound of Example 3 | 15 mg |
| Dried starch | 178 mg |
| Magnesium stearate | 2 mg |
| Total | 195 mg |

Biological Assay:

A fluorescent polarization based binding assay was developed to quantitate interaction of novel test compounds at the ATP binding pocket of RIPK2, by competition with a fluorescently labeled ATP competitive ligand. Full length FLAG His tagged RIPK2was purified from a Baculovirus expression system and was used at a final assay concentration of twice the KDapparent. A fluorescent labeled ligand (5-({[2-({[3-({4-[(5-hydroxy-2-methylphenyl)amino]-2-pyrimidinyl}amino)phenyl]carbonyl}amino)ethyl]amino}carbonyl)-2-(6-hydroxy-3-oxo-3H-xanthen-9-yl) benzoic acid, prepared as described in WO2011/120025) was used at a final assay concentration of 5 nM. Both the enzyme and ligand were prepared in solutions in 50 mM HEPES pH7.5, 150 mM NaCl, 10 mM MgCl2, 1 mM DTT, and 1 mM CHAPS. Test compounds were prepared in 100% DMSO and 100 mL was dispensed to individual wells of a multiwell plate. Next, 5ul RIPK2 was added to the test compounds at twice the final assay concentration, and incubated at rt for 10 minutes. Following the incubation, 5 ul of the fluorescent labeled ligand solution, was added to each reaction, at twice the final assay concentration, and incubated at rt for at least 10 minutes. Finally, samples were read on an instrument capable of measuring fluorescent polarization. Test compound inhibition was expressed as percent (%) inhibition of internal assay controls.

For concentration/dose response experiments, normalized data were fit and pIC$_{50}$s determined using conventional techniques. The pIC$_{50}$s are averaged to determine a mean value, for a minimum of 2 experiments.

As determined using the above method, the compounds of Examples 1-83 exhibited a pIC$_{50}$ between 5.0 and 9.0 e.g., for example, the compounds of Example 1 and Example 74 inhibited RIP2 kinase in the above method with a mean pIC$_{50}$ of 8.2 and 8.6, respectively.

FLAG his Tagged RIPK2 Preparation:

Full-length human RIPK2 (receptor-interacting serine-threonine kinase 2) cDNA was purchased from Invitrogen (Carlsbad, Calif., USA, Clone ID:IOH6368, RIPK2-pENTR 221). Gateway® LR cloning was used to site-specifically recombine RIPK2 downstream to an N-terminal FLAG-6His contained within the destination vector pDEST8-FLAG-His6 according to the protocol described by Invitrogen. Transfection into Spodoptera frugiperda (Sf9) insect cells was performed using Cellfectin® (Invitrogen), according to the manufacturer's protocol.

Sf9 cells were grown in Excell 420 (SAFC Biosciences, Lenexa, Kans., US; Andover, Hampshire UK) growth media at 27° C., 80 rpm in shake flask until of a sufficient volume to inoculate a bioreactor. The cells were grown in a 50 litre working volume bioreactor (Applikon, Foster City, Calif., US; Schiedam, Netherlands) at 27° C., 30% dissolved oxygen and an agitation rate of 60-140 rpm until the required volume was achieved with a cell concentration of approximately 3.7×e6 cells/mL. The insect cells were infected with Baculovirus at a multiplicity of infection (MOI) of 12.7. The cultivation was continued for a 43 hour expression phase. The infected cells were removed from the growth media by centrifugation at 2500 g using a Viafuge (Carr) continuous centrifuge at a flow rate of 80 litres/hour. The cell pellet was immediately frozen and subsequently supplied for purification.

Purification Procedure I: $9.83 \times 10^{10}$ Insect cells were re-suspended in 1.4 L lysis buffer (50 mM Tris (pH 8.0), 150 mM NaCl, 0.5 mM NaF, 0.1% Triton X-100, 1 mL/litre Protease Inhibitor Cocktail Set III (available from EMD Group; CalBiochem/Merck Biosciences, Gibbstown, N.J., US; Damstadt, Germany) and processed by dounce homogenization on ice. The suspension was then clarified by centrifugation at 47,900 g for 2 hours, at 4° C. The lysate was decanted from the insoluble pellet and loaded at a linear flow rate of 16 cm/h onto a 55 mL FLAG-M2 affinity column (2.6×10.4 cm) that had been pre-equilibrated with 10 column volumes buffer A (50 mM Tris (pH 8.0), 150 mM NaCl, 0.5 mM NaF, 1 mL/litre Protease Inhibitor Cocktail Set III). The column was then washed with 15 column volumes buffer A, and eluted with 6 column volumes buffer B (buffer A+150 µg/mL 3×FLAG peptide) at a linear flow rate of 57 cm/h. Fractions identified by SDS-PAGE as containing protein of interest were dialyzed to remove the 3×FLAG peptide from the preparation against 5 L of Buffer A (not containing the Protease Inhibitor Cocktail) overnight, using 10 kDa MWCO SnakeSkin Pleated Dialysis Tubing. The purification process yielded 11.3 mg of total protein, with the RIPK2 present at 40% purity by gel densitometry scanning, and identity confirmed by peptide mass fingerprinting. The main contaminating proteins in the preparation were identified as lower molecular weight degraded species of RIPK2.

Purification Procedure II: 100 g cells (10 liter scale fermentation) were frozen, thawed, and re-suspended in 1 L lysis buffer (50 mM Tris HCL pH7.5, 250 mM NaCl, 0.1 mM TCEP, 3 ml Protease inhibitor cocktail) and lysed by high pressure homogenization at 10,000 psi once (Avestin). The suspension was then clarified by centrifugation at 35,000 g for 45 minutes at 4° C. The supernatant was collected by centrifugation and incubated with 5 ml anti-FLAG-M2 resin which was pre-equilibrated with buffer A (50 mM Tris HCL pH7.5, 250 mM NaCl, 0.1 mM TCEP). After protein binding at 4 C degree for 1 hour, the resin was packed into two 25 ml disposable columns. Each column was washed with 25 ml buffer A and eluted with 10 ml (buffer A+200 ug/ml Flag peptide). The elution pool was concentrated to 1 ml and applied to a superdex 200 (16/60) sizing column. Fractions containing full length RIPK2 were collected according to SDS-PAGE analysis results. The purification process yielded 1.36 mg/L 80% pure RIPK2 protein and identity was confirmed by peptide mass fingerprinting.

Biological In Vivo Assay

The efficacy of RIP2 inhibitors may also be evaluated in vivo in rodents. Intraperitoneal (i.p.) or intravenous (i.v.) administration of L18-MDP in mice has been shown to induce an inflammatory response through activation of the NOD2 signaling pathway (Rosenweig, H. L., et al. 2008. Journal of Leukocyte Biology 84:529-536). The level of the inflammatory response in the L18-MDP treated mice/rats is monitored using conventional techniques by measuring increases in cytokine levels (IL8, TNFα, IL6 and IL-1β) in serum and/or peritoneal lavage fluid and by measuring neutrophil influx into the peritoneal space (when L18-MDP is dosed i.p.). Inhibition of the L18-MDP induced inflammatory response in treated rodents may be shown by orally pre-dosing with selected compounds of this invention, then measuring and comparing cytokine levels (IL8, TNFα, IL6 and IL-1β) in serum and/or peritoneal lavage fluid and neutrophil influx into the peritoneal space (when L18-MDP is dosed i.p.) using conventional techniques.

Figure 2:
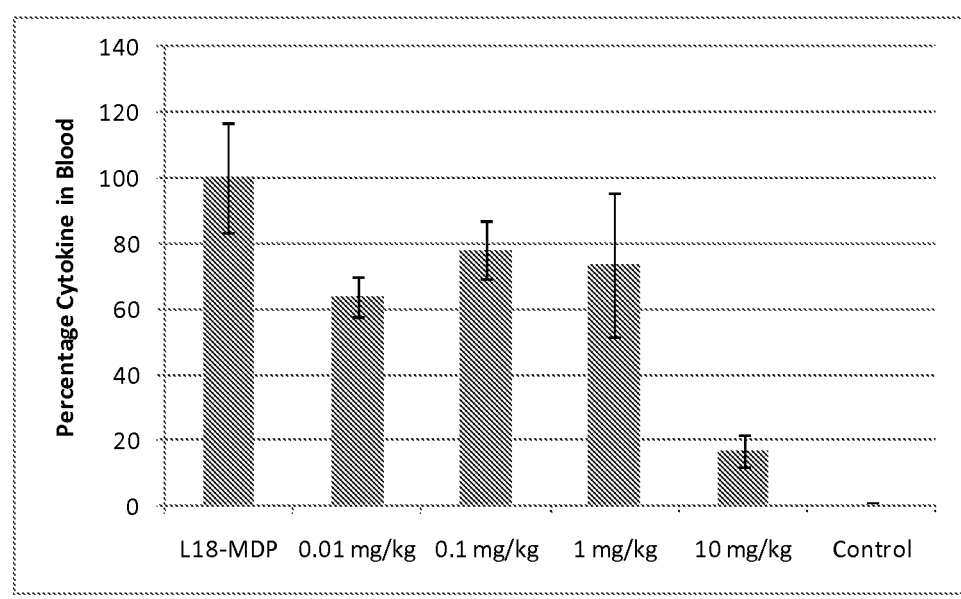
FIG. 2 shows the combined cytokine response in rat whole blood samples obtained after pre-dosing rats with the compound of Example 5, followed by dosing with L18-MDP.

For example, rats (8 rats/dose group for each test or control compound) were orally pre-dosed with the compound of Example 1 at 0.01 to 30 mg/kg, the compound of Example 5 at 0.01 to 10 mg/kg and a compound used as a positive control (prednisolone and a reference compound, for Example 1 and Example 5, respectively), followed by dosing with L18-MDP (50 µg/rat) 0.25 hours after pre-dosing. Combined cytokine levels (IL8, TNFα, IL6 and IL-1β) in whole blood samples taken from the rats in this study were measured using an antibody based detection (Meso-Scale Discovery platform). The combined cytokine response was calculated as the averaged response for the 4 cytokines measured relative to the response observed in the vehicle (L18-MDP) treated mice, and is depicted in FIGS. 1 and 2 as the mean±standard error of the mean (n=8 rats/group).

Figure 3:
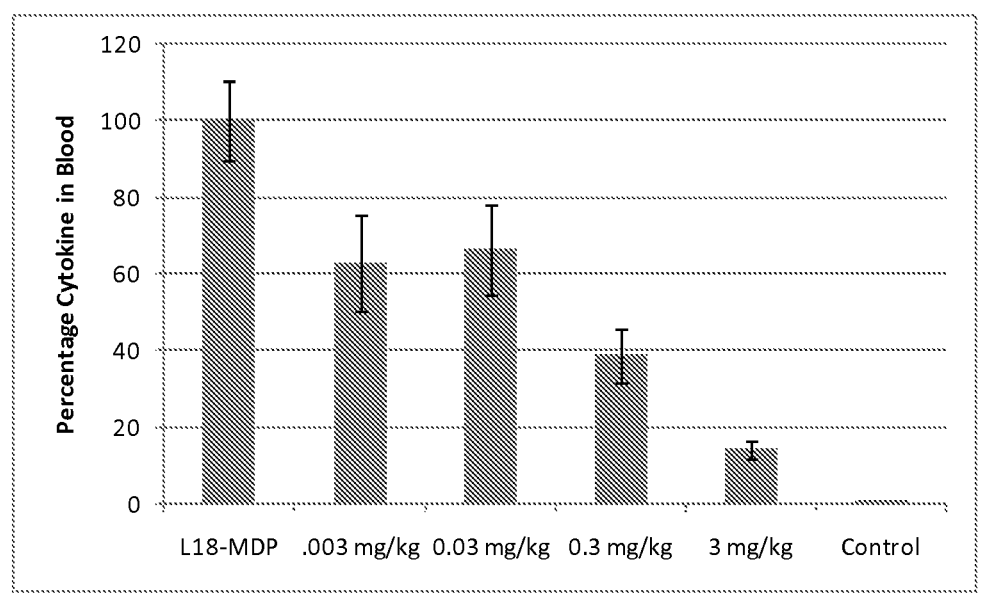
FIG. 3 shows the IL-8 cytokine response in rat whole blood samples obtained after pre-dosing rats with the compound of Example 23, followed by dosing with L18-MDP.
Figure 4:
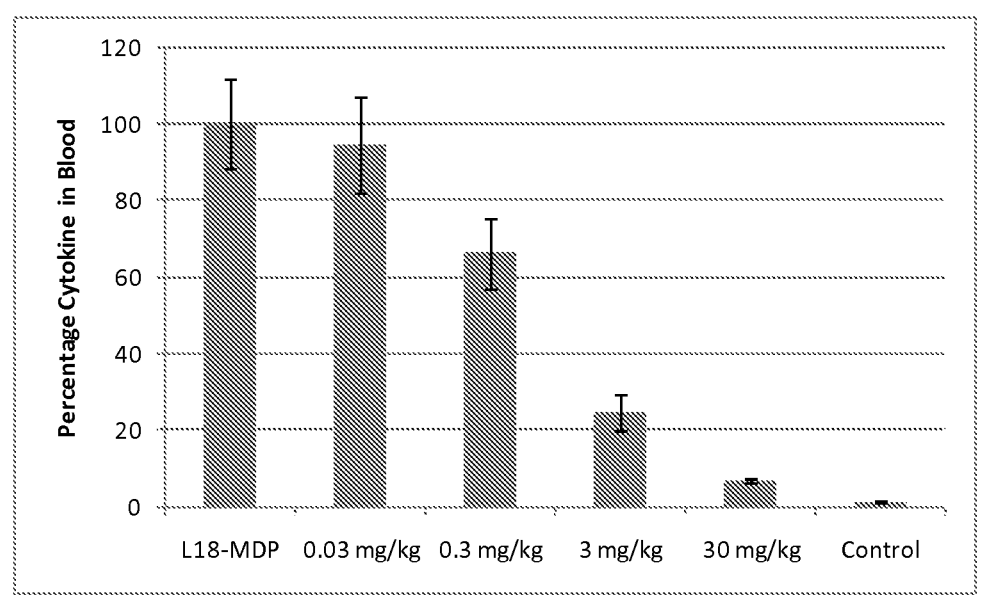
FIG. 4 shows the IL-8 cytokine response in rat whole blood samples obtained after pre-dosing rats with the compound of Example 31, followed by dosing with L18-MDP.

Additionally, the compound of Example 23 at 0.003 to 3 mg/kg, the compound Example 31 at 0.03 to 30 mg/kg, and a reference compound used as a positive control were orally pre-dosed in rats (8 rats/dose group for each test or control compound), followed by dosing with L18-MDP (50 µg/rat) or vehicle 0.25 hours after pre-dosing. Cytokine levels (IL8) in whole blood samples taken from the rats in this study were measured using an antibody based detection (Meso-Scale Discovery platform). The cytokine response was calculated as a percentage relative to the response observed in the vehicle treated mice, and is depicted in FIGS. 3 and 4 as the mean±standard error of the mean (n=8 rats/group).

What is claimed is:

1. A compound according to Formula (I):

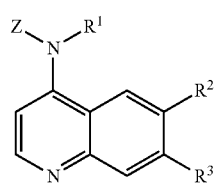

(I)

wherein:

$R^1$ is H, —$SO_2(C_1-C_4$alkyl), —$CO(C_1-C_4$alkyl), or ($C_1$-$C_4$alkyl);

$R^2$ is —$SOR^a$ or —$SO_2R^a$, wherein $R^a$ is an optionally substituted ($C_1$-$C_6$)alkyl, ($C_3$-$C_7$)cycloalkyl, 4-7membered heterocycloalkyl, aryl, or heteroaryl group, wherein:

said ($C_1$-$C_6$)alkyl is optionally substituted by one or two groups each independently selected from the group consisting of cyano, hydroxyl, ($C_1$—$C_6$)alkoxy, ($C_1$-$C_6$)alkoxy($C_2$-$C_6$)alkoxy, —$CO_2H$, —$CO_2(C_1$-$C_4$) alkyl, —$SO_2(C_1$-$C_4$ alkyl), —$CONH_2$, —$CONH(C_1$-$C_4$ alkyl), —$CON(C_1$-$C_4$ alkyl)($C_1$-$C_4$ alkyl), —$SO_2NH_2$, —$SO_2NH(C_1$-$C_4$ alkyl), —$SO_2N(C_1$-$C_4$ alkyl)($C_1$-$C_4$ alkyl), amino, ($C_1$-$C_4$ alkyl)amino-, ($C_1$-$C_4$ alkyl)($C_1$-$C_4$ alkyl)amino-, $C_3$-$C_7$cycloalkyl, phenyl, 5-6membered heteroaryl, 9-10membered heteroaryl, 4-7membered heterocycloalkyl and (phenyl)($C_1$-$C_4$ alkyl)amino-, wherein said $C_3$-$C_7$cycloalkyl, phenyl, (phenyl)($C_1$-$C_4$ alkyl)amino-, 5-6membered heteroaryl, 9-10membered heteroaryl or 4-7membered heterocycloalkyl is optionally substituted by 1-3groups each independently selected from the group consisting of halogen, —$CF_3$, ($C_1$-$C_4$)alkyl, hydroxy($C_1$-$C_4$)alkyl and ($C_1$-$C_4$)alkoxy, said ($C_3$-$C_7$)cycloalkyl or 4-7membered heterocycloalkyl is optionally substituted by 1-3groups each independently selected from the group consisting of halogen, —$CF_3$, hydroxyl, amino, ($C_1$-$C_4$)alkyl, phenyl($C_1$-$C_4$) alkyl-, hydroxy($C_1$-$C_4$)alkyl-, oxo, and ($C_1$-$C_4$)alkoxy, and said aryl or heteroaryl is optionally substituted by 1-3 groups each independently selected from the group consisting of halogen, —$CF_3$, hydroxyl, amino, ($C_1$-$C_4$)alkyl, phenyl($C_1$-$C_4$)alkyl-, hydroxy($C_1$-$C_4$)alkyl- and ($C_1$-$C_4$)alkoxy, and wherein said heteroaryl is a 5-6 membered heteroaryl or a 9-10 membered heteroaryl, and any of said 4-7 membered heterocycloalkyl contains one heteroatom selected from the group consisting of N, O and S, any of said 5-6 membered heteroaryl contains one heteroatom selected from the group consisting of N, O and S and optionally further containing one or two nitrogen atoms, and any of said 9-10 membered heteroaryl contains one heteroatom selected from the group consisting of N, O and S and optionally further containing 1, 2 or 3 nitrogen atoms;

$R^3$ is halogen, hydroxy, ($C_1$-$C_4$)alkoxy-, halo($C_1$-$C_4$) alkyl-, halo($C_1$-$C_4$)alkoxy-, ($C_1$-$C_4$)alkoxy($C_1$-$C_6$) alkyl-, halo($C_1$-$C_4$)alkoxy($C_1$-$C_6$)alkyl-, ($C_1$-$C_4$) alkoxy($C_2$-$C_6$)alkoxy-, halo($C_1$-$C_4$)alkoxy($C_2$-$C_6$) alkoxy-, hydroxy($C_1$-$C_4$)alkyl-, hydroxy($C_2$-$C_6$) alkoxy-, cyano($C_1$-$C_4$)alkyl-, cyano($C_2$-$C_6$)alkoxy-, or ($C_3$-$C_6$)cycloalkoxy-, wherein the halo($C_1$-$C_4$)alkyl-, halo($C_1$-$C_4$)alkoxy-, halo($C_1$-$C_4$)alkoxy($C_1$-$C_6$)alkyl-, or halo($C_1$-$C_4$)alkoxy($C_2$-$C_6$)alkoxy- contains 2 or 3 halo atoms and wherein the ($C_3$-$C_6$)cycloalkyl moiety of the ($C_3$-$C_6$)cycloalkoxy- group, is optionally substituted by a group selected from the group consisting of cyano, halo, hydroxyl, ($C_1$-$C_6$)alkoxy and ($C_1$-$C_4$) alkoxy($C_2$-$C_6$)alkoxy;

Z is pyrazolyl, having the formula:

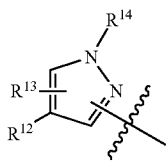

wherein:
$R^{12}$ is methyl or trifluoromethyl;
$R^{13}$ is H, methyl, or trifluoromethyl;
$R^{14}$ is H or $(C_1\text{-}C_3)$alkyl; or
$R^{12}$ and $R^{13}$, taken together with the atoms to which they are attached, form a 6membered carbocyclic ring or heterocyclic ring substituted by $R^{15}$ and $R^{16}$, wherein the heterocyclic ring contains 1 nitrogen atom;
wherein $R^{15}$ and $R^{16}$ are each independently selected from the group consisting of H, halogen, cyano, $(C_1\text{-}C_4)$alkyl, halo$(C_1\text{-}C_4)$alkyl, $(C_1\text{-}C_4)$alkoxy, phenoxy, phenyl$(C_1\text{-}C_4)$alkoxy, hydroxyl, hydroxy$(C_1\text{-}C_4)$alkyl-, and aminocarbonyl, wherein the phenyl moiety of said phenoxy or phenyl$(C_1\text{-}C_4)$alkoxy is optionally substituted by 1-3 substituents each independently selected from the group consisting of halogen, —$CF_3$, $(C_1\text{-}C_4)$alkyl and $(C_1\text{-}C_4)$alkoxy;
or a salt thereof.

2. The compound or salt according to claim 1, wherein $R^1$ is H.

3. The compound or salt according to claim 1, wherein $R^2$ is -$SO_2R^a$.

4. The compound, or salt thereof, according to claim 1, wherein the salt is a pharmaceutically acceptable salt of said compound.

5. A compound which is:

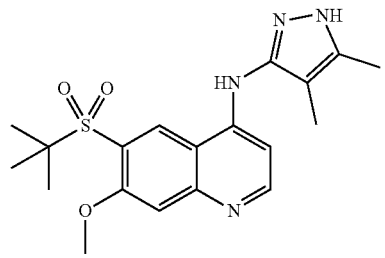 [SMILES: COc1cc2nccc(Nc3n[nH]c(C)c3C)c2cc1S(=O)(=O)C(C)(C)C]

or a pharmaceutically acceptable salt thereof.

6. A pharmaceutical composition comprising the compound, or pharmaceutically acceptable salt thereof, according to claim 4, and a pharmaceutically acceptable excipient.

7. A pharmaceutical composition comprising the compound, or pharmaceutically acceptable salt thereof, according to claim 5, and a pharmaceutically acceptable excipient.

* * * * *